United States Patent
Ashibe et al.

[11] Patent Number: 5,772,606
[45] Date of Patent: Jun. 30, 1998

[54] METHOD OF AND APPARATUS FOR MEASURING URIC COMPONENTS

[75] Inventors: Emi Ashibe; Takeshi Sakura; Harumi Uenoyama; Xu Kexin; Hiroko Kubo, all of Kyoto, Japan

[73] Assignee: Kyoto Dai-Ichi Kagaku Co., Ltd., Kyoto, Japan

[21] Appl. No.: 397,953

[22] Filed: Mar. 3, 1995

[30] Foreign Application Priority Data

| Mar. 4, 1994 | [JP] | Japan | 6-060014 |
| Mar. 4, 1994 | [JP] | Japan | 6-060015 |
| Mar. 7, 1994 | [JP] | Japan | 6-064505 |

[51] Int. Cl.⁶ ............................................. A61B 5/00
[52] U.S. Cl. ................................. 600/573; 600/584
[58] Field of Search ........................ 128/760, 771; 356/73

[56] References Cited

U.S. PATENT DOCUMENTS

| 4,427,889 | 1/1984 | Müller | 250/338 |
| 4,665,571 | 5/1987 | Muccione | 4/144 |
| 4,860,767 | 8/1989 | Maekawa | 128/760 |
| 4,935,875 | 6/1990 | Shah et al. | 364/497 |
| 4,961,431 | 10/1990 | Ikenaga et al. | 128/760 |
| 4,961,931 | 10/1990 | Ikenaga et al. | 128/760 |
| 5,073,500 | 12/1991 | Saito et al. | 128/760 |
| 5,370,114 | 12/1994 | Wang et al. | 128/633 |
| 5,422,712 | 6/1995 | Ogino | 356/73 |

FOREIGN PATENT DOCUMENTS

| 0 210 869 A1 | 2/1987 | European Pat. Off. . |
| 0 285 251 A1 | 10/1988 | European Pat. Off. . |
| WO 81/00622 | 3/1981 | WIPO . |

OTHER PUBLICATIONS

Patent Abstracts of Japan, 2027264, Publication Date: Jan. 30, 1990 Title: Optical Urine Component Measuring Toilet Stool.

Patent Abstracts of Japan, 3084127, Publication Date: Apr. 9, 1991 Title: Stool for Analyzing Urinary Data.

*Primary Examiner*—Max Hindenburg
*Assistant Examiner*—Pamela L. Wingood
*Attorney, Agent, or Firm*—Nikaido Marmelstein Murray & Oram, LLP

[57] ABSTRACT

A urinal is provided on its forward end with a cell, which internally communicates with the urinal to outwardly project from the same. A measuring part comprises a light source part for applying a measuring beam of the visible or near infrared wavelength region to the cell which is set in a cell setting part and a light receiving part for receiving and detecting the measuring beam transmitted through the cell, and measures absorbances of uric components to be measured at wavelengths selected therefor respectively. A sensor part is adapted to detect that the cell is set in the cell setting part, so that the measuring part starts a measuring operation on the basis of a signal indicating that the sensor detects the cell. It is possible to carry out a urine test on a person who lies on bed.

23 Claims, 42 Drawing Sheets

Fig. 22 CALIBRATION CURVE OF AQUEOUS GLUCOSE SOLUTION AT 4398 cm$^{-1}$

Fig. 35 CALIBRATION CURVE OF AQUEOUS ASCORBIC ACID SOLUTION AT 4404 cm$^{-1}$

Fig. 38 CALIBRATION CURVE OF AQUEOUS CREATININE SOLUTION AT 4370 cm$^{-1}$

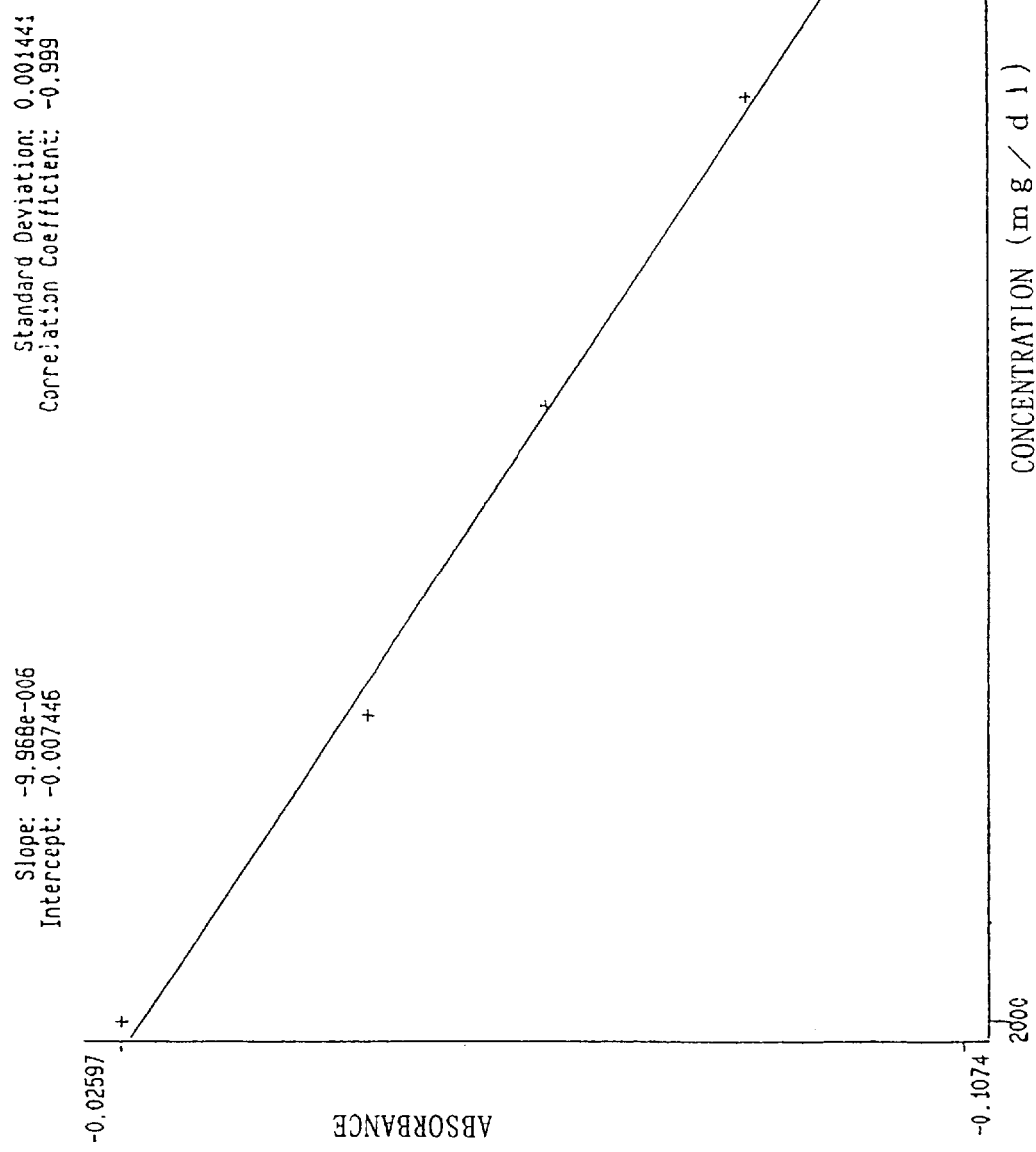
Fig. 44 CALIBRATION CURVE OF AQUEOUS SODIUM NITRITE SOLUTION AT 6766 cm$^{-1}$

METHOD OF AND APPARATUS FOR MEASURING URIC COMPONENTS

BACKGROUND OF THE INVENTION

1. Field of the Invention

The present invention relates to a method of simultaneously measuring concentrations of a plurality of uric components in the field of a clinical test, and a measuring apparatus and a stool to which the method is applied.

2. Description of the Background Art

It is important not only for an old person, a sick person and a baby but for an ordinary person to regularly test health. Diabetes is judged by testing a glucose concentration in the blood, while effectiveness/defectiveness of the renal function is judged by testing a bilirubin concentration in the blood. It is difficult for a general person to make such tests, which are generally made by a doctor in a special institution such as a hospital, at home or in an office.

A urine test is a non-invasive test which is easier in sampling as compared with measurement of hematic components. Through this urine test, it is possible to measure components such as glucose, protein, urobilinogen and occult blood for investigating possibilities of diabetes, nephrosis, a hepatic disease, an inflammation, a calculus or a tumor of the kidney, bladder or urethra, or prostatitis respectively, as well as the ketone body, bilirubin, nitrous acid and salt. It is possible to find various diseases in early stages for caring health by tracing concentrations of such uric components every day.

Methods of measuring uric components are a reagent method, a paper test, a chemiluminescence method, an immunoassay method, an enzyme method and chromatography.

The reagent method is adapted to measure glucose and protein with reagents.

A test paper employed in the paper test is generally prepared by fixing a reacting portion which is prepared by introducing reactive reagents into cellulose to a plastic support member with an adhesive or the like and drying the same. The reacting portion is generally reduced in sensitivity when the same is moistened due to reaction between the reagents or deterioration caused by a high temperature or light. Therefore, it is necessary to seal a container for storing the test paper to preserve the same at an ordinary temperature, and to use the same within the effective period. According to the paper test, it is possible to measure each of a pH value, protein, glucose, the ketone body, bilirubin, occult blood, urobilinogen, nitrate and microbism within 1 minute. However, the reaction between the reagents is influenced by endogenous promoting agents and inhibitors as well as by the reaction temperature and conditions of the test paper, and hence merely semi-quantitative analysis is available.

The enzyme method is employed for measuring glucose. There are carried out a method of forming a GOD-POD (glucose oxidase-peroxidase) pigment system on a test paper and measuring coloring following oxidation-reduction reaction with a reflectiometer, and a method of amperometrically measuring an anodizing current by a GOD immobilized enzyme electrode and converting the current value to concentration (biosensor or the like). While a method employing a glucose oxidizing enzyme is simple with high specificity for glucose, GOD reaction is oxidation-reduction reaction and may be suppressed by various endogenous and exogenous oxidizing and reducing substances, and there is also a probability for appearance of false-negative or false-positive reaction.

The reagent method, the paper test and the enzyme method require reagents, test papers and enzyme which are expendables, along with problems in relation to preservability of unused reagents and disposal after usage. Further, operations in these methods are so complicated that malfunctions are caused by erroneous operations as to the quantities of the reagents and samples, while interfering actions may be disadvantageously caused by other components such as ascorbic acid which is not the target of measurement. It is impossible to simultaneously measure a number of components by the reagent method and the enzyme method although quantitative analysis is available, while only semi-quantitative analysis is available in the paper test although a number of components can be measured at the same time.

The chromatography requires a high-priced apparatus, and it is necessary to exchange a column if its performance is deteriorated, leading to a high cost.

Exemplary apparatuses for measuring uric components are a generic apparatus for urine measurement which is employed in a hospital or the like, and a toilet apparatus provided with a measuring apparatus. The generic apparatus is mainly set only in a specific medical institution such as a hospital, and the patient collects his urine in a container such as a paper cup and carries this container to a laboratory for testing. However, a tester who tests a large volume of specimens in such a hospital or the like must transfer the urine collected by patients from paper cups to cells with a significant burden.

Although it is possible to individually test urine, such a test is not generally made due to complicatedness of the operation. A stool provided with a measuring apparatus has been developed as an apparatus for prompting an individual urine test. As to apparatuses for daily testing diabetes and the like, there have been proposed an apparatus for partially collecting urine in a prescribed portion of a stool and dipping a test paper therein for measuring glucose contained in the urine (Japanese Patent Publication No. 5-39552 (1993)), an apparatus having a urine collecting chamber which is provided in a stool for measuring glucose and bilirubin contained in the urine with reagents (Japanese Patent Publication No. 5-29266 (1993)), a method of adding a precipitant to urine collected from a stool and measuring the mass of the precipitate thereby quantitatively analyzing protein (Japanese Patent Laying-Open No. 4-233457 (1992)), a method of quantitatively analyzing occult blood by adding a reagent to urine collected from a stool (Japanese Patent Laying-Open No. 5-2017 (1993)), and a method of collecting urine in a container communicating with a stool for quantitatively analyzing glucose and uric acid through a biosensor (enzyme reaction) (Japanese Patent Publication No. 4-34445 (1992)).

In the apparatus having a measuring apparatus which is provided on a stool, it is possible for a person who can freely move to collect urine at the toilet for testing the collected urine by himself. However, it is difficult for a handicapped patient to go to the toilet. In recent years, the number of old persons is increased with increase in number of bed-ridden old persons. While it is important for such persons to check health every day, it is impossible for those having difficulty in going to the toilet to test urine.

Such stools employ expendables such as reagents, test papers and enzyme in common.

SUMMARY OF THE INVENTION

A first object of the present invention is to provide a method of quantitatively measuring a plurality of uric components at the same time while removing necessity for reagents, test papers and enzyme which are expendables and eliminating problems such as preservability of these expendables in unused states and disposal after usage as well as complicated operations causing malfunctions and interfering actions by other components.

A second object of the present invention is to provide an apparatus to which the aforementioned method is applied so that it is possible to test urine even if the user lies on a bed.

A third object of the present invention is to eliminate the necessity for reagents, test papers and enzyme which are expendables and to enable simultaneous quantitative analysis of a plurality of uric components by applying the aforementioned method to a stool comprising a uric component measuring apparatus.

A method of measuring uric components according to the present invention comprises the steps of irradiating a urine sample with visible or near infrared light, measuring absorbances of said uric components to be measured at measuring wavelengths being selected from wavelengths having absolute values of at least 0.5, preferably at least 0.9, of correlation coefficients between concentrations and absorbances of aqueous solutions containing respective single components in the visible or near infrared wavelength region as measuring wavelengths being specific to respective said urine components, and quantitatively analyzing said plurality of uric components at the same time from said absorbances being measured at said measuring wavelengths by multivariate regression analysis. Thus, it is possible to measure a plurality of components contained in a urine sample at the same time with neither requirement for expendables such as reagents and test papers nor problem of disposal of such expendables after usage.

A correlation coefficient $Rj$ of a component between an absorbance $A$ at a wavelength $\lambda j$ and a concentration $C$ is expressed in the following formula:

$$Rj = \frac{(m-1)\sum_{i=1}^{m}(Aij - \overline{Aj})(Ci - \overline{C})}{\sum_{i=1}^{m}(Aij - \overline{Aj}) \cdot \sum_{i=1}^{m}(Ci - \overline{C})}$$

$$\overline{Aj} = \frac{1}{m}\sum_{i=1}^{m}Aij$$

$$\overline{C} = \frac{1}{m}\sum_{i=1}^{m}Ci$$

where, m; the number of samples

Aij; absorbance of the component in i th sample at wavelength $\lambda j$

Ci; concentration of the component in i th sample

The measuring wavelengths for the respective uric components are selected from a wave number region of 25000 to 5280 cm$^{-1}$ or 4980 to 4000 cm$^{-1}$ having high transmittance with respect to water while avoiding a wavelength region having strong absorption with respect to water.

Preferable measuring wavelengths for the respective components, expressed in wavenumbers, are selected:

from 11380 to 9720 cm$^{-1}$, 9430 to 9400 cm$^{-1}$, 9340 to 9320 cm$^{-1}$, 9260 to 6560 cm$^{-1}$, 6510 to 5540 cm$^{-1}$, 5530 to 5280 cm$^{-1}$, 4980 to 4850 cm$^{-1}$, 4830 to 4480 cm$^{-1}$, 4440 to 4330 cm$^{-1}$ or 4300 to 4010 cm$^{-1}$ for glucose, from 25000 to 7250 cm$^{-1}$, 7220 to 6430 cm$^{-1}$, 6190 to 5690 cm$^{-1}$, 5660 to 5280 cm$^{-1}$ or 4900 to 4080 cm$^{-1}$ for hemoglobin, from 7280 to 6350 cm$^{-1}$, 5910 to 5880 cm$^{-1}$, 5790 to 5740 cm$^{-1}$, 5630 to 5300 cm$^{-1}$, 4900 to 4720 cm$^{-1}$, 4670 to 4280 cm$^{-1}$ or 4230 to 4070 cm$^{-1}$ for albumin, from 8490 to 6360 cm$^{-1}$, 6040 to 5610 cm$^{-1}$, 5430 to 5300 cm$^{-1}$, 4900 to 4760 cm$^{-1}$, 4680 to 4510 cm$^{-1}$ or 4470 to 4320 cm$^{-1}$ for lithium acetoacetate, from 7270 to 6520 cm$^{-1}$, 6430 to 5290 cm$^{-1}$, 4950 to 4860 cm$^{-1}$ or 4810 to 4090 cm$^{-1}$ for ascorbic acid, from 9370 to 5870 cm$^{-1}$, 5810 to 5280 cm$^{-1}$, 4980 to 4730 cm$^{-1}$, 4690 to 4320 cm$^{-1}$ or 4290 to 4090 cm$^{-1}$ for creatinine, from 7640 to 5280 cm$^{-1}$ or 4980 to 4080 cm$^{-1}$ for sodium chloride, and from 8680 to 5300 cm$^{-1}$, 4980 to 4210 cm$^{-1}$ or 4160 to 4100 cm$^{-1}$ for sodium nitrite.

When a sample is irradiated with light for measurement of the absorbance, transmitted light intensity Itj at a wavelength $\lambda j$ is expressed as follows, along the Lambert-Beer's law:

$$\begin{aligned} Itj &= Ioj \exp(-\Sigma \alpha kj\, Ck\, L) \\ &= Ioj\, Tj \end{aligned} \quad (1)$$

where

Itj; transmitted light intensity at the wavelength $\lambda j$

Ioj; intensity of incident light at the wavelength $\lambda j$ $\alpha kj$; an absorption coefficient of k th component at the wavelength $\lambda j$ Ck; the concentration of k th component in the solution k=1, 2, . . . , K, K represents the number of components contained in the solution.

Tj; the transmittance at the wavelength $\lambda j$

L; the cell length

Ignoring reflection at the interface between the cell and the solution, the absorbance Aj at the wavelength $\lambda j$ is expressed as follows:

$$\begin{aligned} Aj &= -\log Tj \\ &= -\log(Itj/Ioj) \\ &= L\,\Sigma(\alpha kj\, Ck) \end{aligned} \quad (2)$$

From the expression (2), the unknown variable is Ck (k=1, 2, . . . , K), and hence it is possible to calculate the concentrations of the respective components by measuring absorbances at K independent wavelengths and solving simultaneous equations. When multivariate regression analysis such as principle component regression analysis (PCR) or partial least square analysis (PLS) is employed to analyze the data, it is possible to obtain the concentrations in higher accuracy.

According to the multivariate regression analysis which can make regression analysis by simultaneously employing a number of absorbance data, it is possible to make quantitative analysis in higher accuracy as compared with single regression analysis. While multiple linear regression analysis is most generally employed, a number of samples are required and quantitative analytical accuracy thereof is extremely reduced when absorbances at respective wavelengths are highly correlated with each other. According to the principal component regression analysis which is the multivariate regression analysis, on the other hand, it is possible to intensify absorbance data of multiple wavelengths to principal components which are not correlated with each other as well as to eliminate unnecessary noise data, whereby high quantitative analytical accuracy can be attained. Further, the partial least square analysis can also utilize data of sample concentrations in extraction of principal components, whereby high quantitative analytical accuracy can be attained similarly to the principal component regression analysis.

The inventive uric component measuring apparatus makes it possible to readily mount the measuring apparatus on a urine collecting part for collecting urine or to readily sample urine from such a urine collecting part, or mount a measuring cell on the urine collecting part itself.

Referring to FIG. 9 schematically showing the inventive uric component measuring apparatus, urine which is stored in a urine collecting part 101 is directly measured by a measuring part 102, measured by a cell which is mounted on the urine collecting part 101, or sampled from the urine collecting part 101 for measurement of absorbances of the urine. Uric component concentrations are calculated by an arithmetic processing part 103 from the absorbances measured in the measuring part 102, and displayed on a display part 104.

According to a first aspect of the present invention, the uric component measuring apparatus comprises a probe, a measuring part and an arithmetic processing unit. The probe is provided on its forward end with a light transmission end and a light receiving end which are opposed to each other at a prescribed space, and comprises a light transmission side guide path for guiding a measuring beam to the light transmission end and a light receiving side guide path for guiding a measuring beam incident upon the light receiving end to the measuring part. This probe is provided on a urine collecting part so that its forward end is dipped in urine which is stored in the urine collecting part and base end portions of the guide paths are located outside the urine collecting part. The measuring part comprises a light source part for introducing a measuring beam of the visible or near infrared wavelength region to the base end portion of the light transmission side guide path of the probe, and a light receiving part for receiving and detecting the measuring beam guided by the light receiving side guide path of the probe, and measures absorbances at measuring wavelengths which are selected for respective ones of uric components to be measured. The arithmetic processing part calculates a plurality of uric component concentrations on the basis of the absorbances measured at the plurality of measuring wavelengths in the measuring part.

According to a second aspect of the present invention, the uric component measuring apparatus comprises a urine collecting part, a measuring part and an arithmetic processing part which is identical to the above. The urine collecting part comprises a cell, which internally communicates with a urine collecting part body and projects from the urine collecting part body to have a prescribed optical path length. The measuring part has a cell setting part for setting the cell of the urine collecting part, and comprises a light source part for irradiating the cell which is set in the cell setting part with a measuring beam of the visible or near infrared wavelength region and a light receiving part for receiving and detecting the measuring beam transmitted through the cell, for measuring absorbances of respective uric components to be measured at wavelengths selected therefor respectively. According to the second aspect of the present invention, the measuring part preferably further comprises a sensor part for optically or mechanically detecting that the cell is set in the cell setting part, so that an operation of the measuring part is started on the basis of a signal indicating that the sensor part detects the cell.

According to a third aspect of the present invention, the uric component measuring apparatus comprises a urine collecting part, a measuring part and an arithmetic processing part which is identical to the above. The urine collecting part comprises an openable/closable urine discharge nozzle, which projects from a urine collecting part body. The measuring part comprises a cell which is arranged on a position for receiving the urine discharged from the nozzle of the urine collecting part, a light source part for irradiating the cell with a measuring beam of the visible or near infrared wavelength region, and a light receiving part for receiving and detecting the measuring beam transmitted through the cell, for measuring absorbances at measuring wavelengths which are selected for respective ones of uric components to be measured. According to the third aspect, the urine discharge nozzle of the urine collecting part is preferably formed by an electromagnetic nozzle which is opened/closed by an electromagnetic valve, and the measuring part preferably further comprises a sensor part for optically or mechanically detecting that the nozzle is set in a prescribed position of the measuring part. The electromagnetic valve of the nozzle is preferably formed to be opened for a constant time on the basis of a signal indicating that the sensor part of the measuring part detects the nozzle.

In the uric component measuring apparatus according to the present invention, absorbances of the urine stored in the urine collecting part are directly measured by the measuring part, measured by the cell which is mounted on the urine collecting part, or measured by sampling the urine from the nozzle provided on the urine collecting part so that uric component concentrations are arithmetically processed from the measured absorbances, whereby it is possible to readily test the urine in a state lying on bed.

There are a local analyzing system carrying out data analysis of uric components by an apparatus provided on a stool and a host analyzing system implementing data analysis by a host computer etc. provided in the exterior of a stool, for the stool according to the present invention.

The local analyzing system comprises a stool body, a urine collecting part which is provided in the stool body on a position for receiving urine, a measuring part having a cell receiving the urine collected in the urine collecting part, a light source part for irradiating the cell with a measuring beam of the visible or near infrared wavelength region, and a light receiving part for receiving and detecting the measuring beam transmitted through the cell for measuring absorbances of uric components to be measured at measuring wavelengths selected therefor respectively, a data analysis part for calculating a plurality of uric component concentrations on the basis of the absorbances measured at the plurality of measuring wavelengths in the measuring part, and an input/output part having a data input part for inputting data required for the measuring operation and a test result output part for outputting the results of the data analysis in the data analysis part.

The host analyzing system comprises a stool body, a urine collecting part which is provided in the stool body on a position for receiving urine, a measuring part having a cell for receiving the urine collected in the urine collecting part, a light source part for irradiating the cell with a measuring beam of the visible or near infrared wavelength region and a light receiving part for receiving and detecting the measuring beam transmitted through the cell for measuring absorbances of uric components to be measured at measuring wavelengths selected therefor respectively, a data transmission part for transmitting the absorbances measured at the plurality of measuring wavelengths in the measuring part to an external data analysis part for calculating a plurality of uric component concentrations on the basis thereof and receiving results of the data analysis from the data analysis part, and an input/output part having a data input part for inputting data required for the measuring operation and a test result output part for receiving the results of the data analysis from the data analysis part through the data transmission part and outputting the same.

Uric components adhering to the urine collecting part and the cell cause contamination and reduce transmittance of the cell, leading to reduction in measuring sensitivity. It is preferable to provide a washing mechanism for the urine collecting part and the cell, for washing the same before and after every measurement.

It is preferable to provide a sensor part for checking the degrees of soiling for the urine collecting part and the cell, to start the washing mechanism when the urine collecting part and the cell are decided as being soiled in excess of previously set levels. Thus, it is possible to readily maintain the urine collecting part and the cell in states suitable for measurement.

When individual data as well as measurement items are designated by the data input part and the measurement is started in the stool according to the present invention, the urine collected in the urine collecting part is transmitted to the cell of the measuring part, so that the cell is irradiated with the measuring beam from the light source part. The measuring beam transmitted through the cell is received by the light receiving part. The measuring part measures absorbances of uric components corresponding to the designated measurement items at the wavelengths selected therefor respectively. The data analysis part calculates a plurality of uric component concentrations on the basis of the absorbances measured at the plurality of measuring wavelengths, to output the results from the test result output part. Thus, no expendables such as high-priced reagents, test papers and enzyme are required but a plurality of components can be quantitatively measured at the same time. Further, an individual can readily test his urine.

In the local analyzing system, it is possible to carry out data analysis of uric components by the apparatus provided on the stool and output the results of the data analysis, whereby this system can be installed at home or the like with no restriction of the installation place, while the same is easy to move.

In the host analyzing system, on the other hand, the data analysis is implemented by the host computer etc. provided in the exterior of the stool, whereby a large quantity of data can be processed at a high speed to process a number of components in a short time.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 44 illustrates a calibration curve showing relation between concentrations and absorbances of an aqueous sodium nitrite solution at 6766 cm$^{-1}$.

DESCRIPTION OF THE PREFERRED EMBODIMENTS

Figure 1:
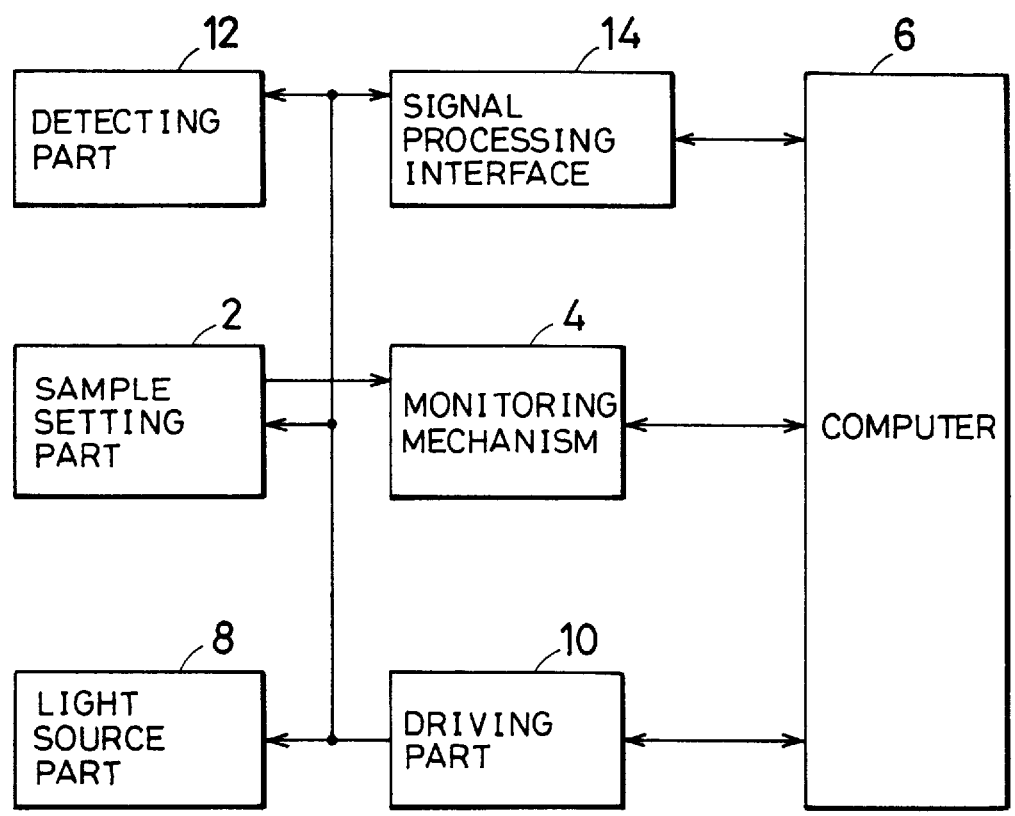
FIG. 1 is a block diagram schematically showing a measuring apparatus employed for the inventive measuring method.

FIG. 1 schematically shows a measuring apparatus which is employed for a method of measuring uric components according to the present invention.

A sample setting part 2 has a cell, which stores a urine sample. An optical monitoring mechanism 4 monitors whether or not the cell stores the sample. The monitoring mechanism 4 is controlled by a computer 6.

A light source part 8 comprises a laser diode array for emitting a laser beam having a wavelength for measurement, a laser unit having a variable oscillation wavelength, or a lamp source for emitting light of a continuous wavelength. A driving part 10 is adapted to switch the wavelength at the light source part 8. This driving part 10 is also controlled by the computer 6.

A detecting part 12 is provided for detecting the measuring beam which is transmitted through the sample in the sample setting part 2, and this detecting part 12 is provided with an array-type photoreceptor of CCD(charge coupled device), a photoreceptor array or a single photoreceptor as a detector. A detection signal from the detecting part 12 is converted to absorbance by a signal processing interface 14, and incorporated into the computer 6 as a digital signal.

Figure 2A:
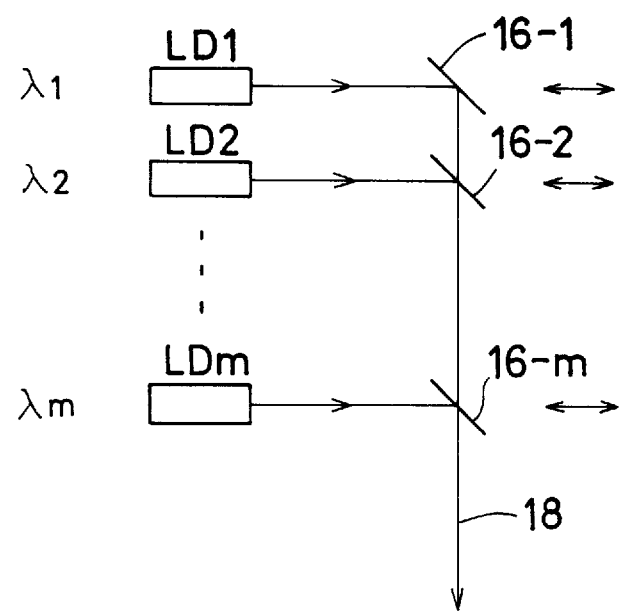
FIG. 2(A) is a schematic diagram showing a movable mirror type optical system for bringing a plurality of beams onto a single optical axis in a light source part.
Figure 2B:
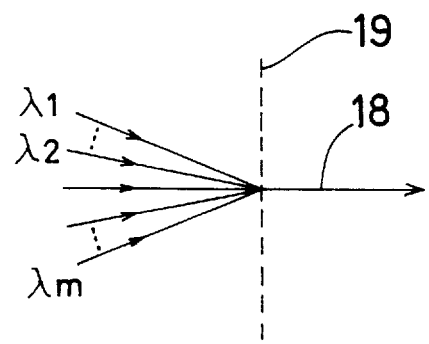
FIG. 2(B) is a schematic diagram showing an optical grating type optical system for bringing a plurality of beams onto a single optical axis in a light source part.

When a variable-wavelength laser unit or a lamp of a continuous wavelength is employed in the light source part 8 as a light source, no optical system is required for mixing beams since only a single optical path is derived from the light source. When a plurality of laser diodes are employed, however, an optical system shown in FIGS. 2(A) or 2(B) is required for the light source part 8, in order to arrange a measuring beam of a selected wavelength on a measuring optical path. FIG. 2(A) shows a movable mirror type optical system. Mirrors 16-1 to 16-m are arranged for reflecting laser beams of different wavelengths λ1 to λm which are emitted from a plurality of laser diodes LD1 to LDm and advancing the same onto a common optical axis 18. These mirrors 16-1 to 16-m are supported to be movable between positions on the optical axis 18 and those displaced from these positions. When only a mirror corresponding to a laser beam of a selected wavelength is placed on the optical axis 18 and the remaining mirrors are displaced from the optical axis 18, the selected laser beam is advanced onto the optical system 18.

FIG. 2(B) shows a diffraction grating 19 for advancing laser beams received from laser diodes of a plurality of wavelengths onto an optical axis 18. The laser beams of respective wavelengths λ1 to λm are incident upon the diffraction grating 19 at angles of incidence which are responsive to the respective wavelengths λ1 to λm so that diffraction beams thereof are guided onto the common optical axis 18.

Figure 3A:
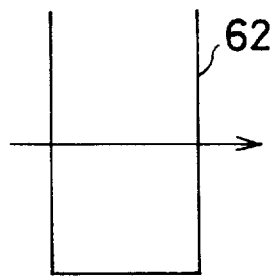
FIG. 3(A) is a schematic front elevational sectional view showing a cell having a single optical path length.
Figure 3B:
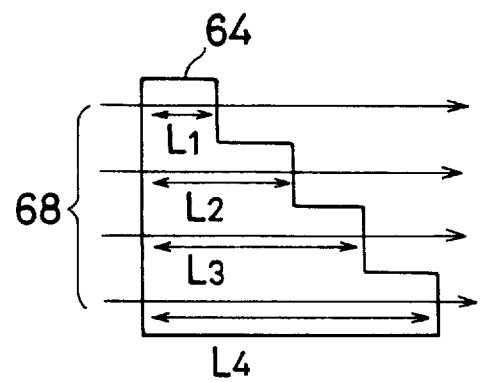
FIG. 3(B) is a schematic plan view showing a cell having four optical path lengths.
Figure 3C:
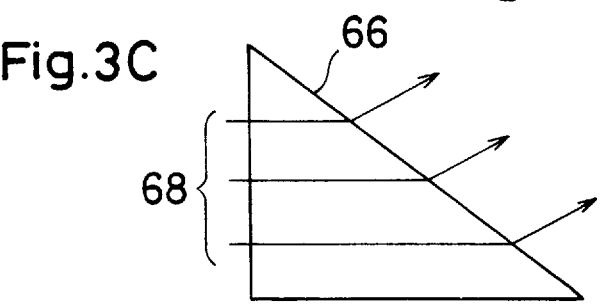
FIG. 3(C) is a schematic plan view showing a cell having a continuously changed optical path length.

The cell provided in the sample setting part 2 is not restricted to a cell 62 having a single optical length as shown in FIG. 3(A), but can be provided with continuously or stepwisely differing optical path lengths. FIGS. 3(B) and 3(C) show exemplary cells having plural optical path lengths. A cell 64 shown in FIG. 3(B) has four optical path lengths L1 to L4, while a cell 66 shown in FIG. 3(C) has continuously changed optical path lengths. Light quantity measurement sensitivity depends on optical path lengths and wavelengths. In order to measure a plurality of uric components, measuring wavelengths are selected in response to the respective components. When the cell shown in FIGS. 3(B) or 3(C) is employed, therefore, it is possible to select optical path lengths having the most excellent light quantity measurement sensitivity in response to the measuring wavelengths. In this case, beam sectional areas of measuring beams of selected wavelengths received from a light source may be enlarged by the optical system so that the beams are incident upon the cell as parallel beams 68 having wide sectional areas and the plurality of measuring beams transmitted through different optical path lengths are simultaneously detected by an array type detector such as a CCD array. It is possible to carry out measurement with large S-N(signal to noise) ratios by calculating component concentrations with detection signals having optical path lengths which are most suitable for measuring wavelengths responsive to the components to be measured.

Figure 4A:
FIG. 4(A) is a schematic plan view showing an array-type photoreceptor formed by a CCD.
Figure 4B:
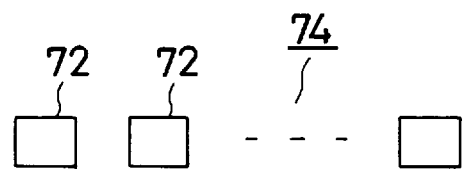
FIG. 4(B) is a schematic plan view showing a photoreceptor array formed by arraying photoreceptors such as photodiodes.
Figure 4C:
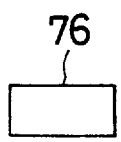
FIG. 4(C) is a schematic plan view showing a single photoreceptor.

The detector provided in the detecting part 12 may be selected from various detectors such as those shown in FIGS. 4(A) to 4(C), showing an array-type detecting element 70 consisting of CCD, a photoreceptor array 74 prepared by arraying photoreceptors 72 such as photodiodes, and a single photoreceptor 76 respectively.

Figure 5A:
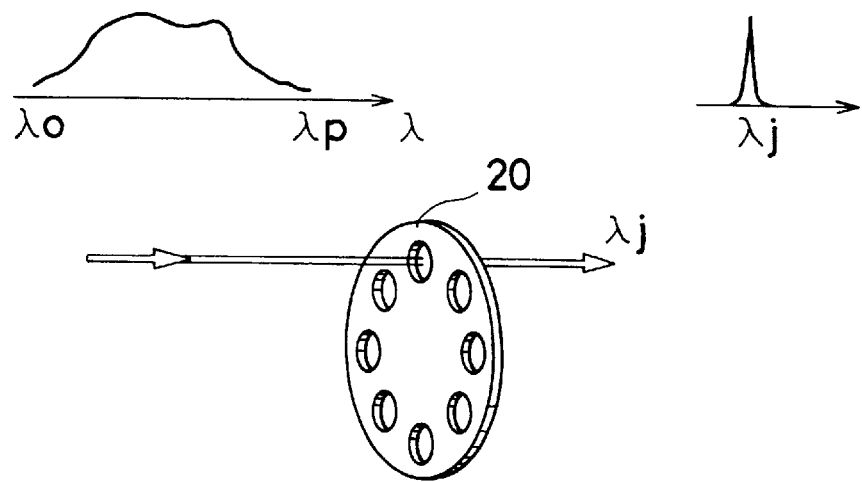
FIG. 5(A) is a schematic diagram showing a filter employed as a spectroscopic part.
Figure 5B:
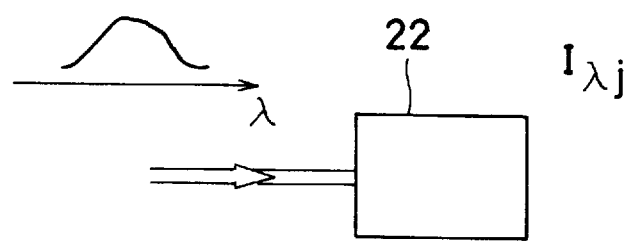
FIG. 5(B) is a schematic diagram showing a spectroscope employed as a spectroscopic part.

When a lamp source emitting light of a continuous wavelength is employed as the light source of the light source part 8, it is necessary to spectroscopically analyze the light every selected wavelength as to each uric component before incidence upon or after transmission through the sample. FIGS. 5(A) and 5(B) illustrate an exemplary spectroscopic part which comprises a filter switching mechanism 20 formed by arranging a plurality of filters on its circumference for selecting wavelengths by switching the filters, and another exemplary spectroscopic part which is adapted to select wavelengths by a spectroscope 22 respectively.

Figure 6:
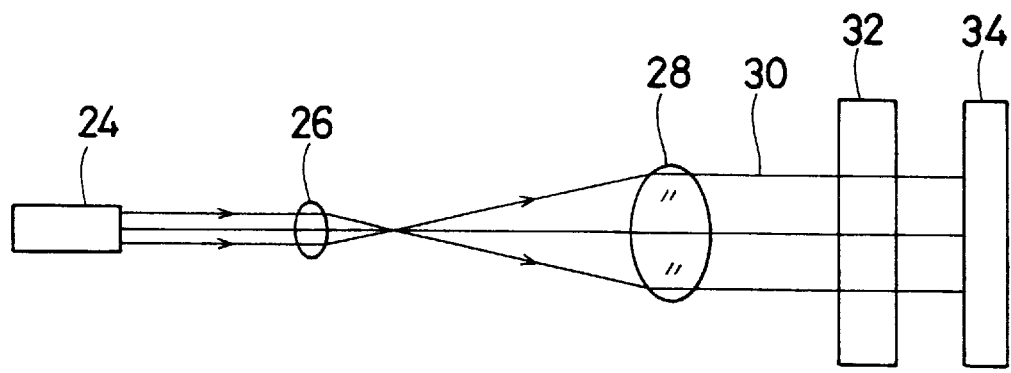
FIG. 6 is a schematic diagram showing a measuring apparatus employing a laser having a variable wavelength as a light source.

FIG. 6 shows an exemplary variable wavelength laser unit 24 which is employed as the light source. A laser beam emitted from the variable wavelength laser unit 24 is incident upon a cell 32 stored in the sample setting part 2 as a spatial parallel beam 30 through condenser lenses 26 and 28, so that the measuring beam transmitted through the cell 32 is detected by a single photoreceptor 34.

In order to carry out measurement with the measuring apparatus shown in FIG. 6, the wavelength of the laser beam which is emitted from the laser unit 24 is changed from j=1 to n while maintaining the cell 32 in a vacant state, so that transmitted light quantities Ioj (j=1, 2, ..., n) are measured.

Then, a urine sample is introduced into the cell 32 and the wavelength of the laser beam which is emitted from the laser unit 24 is changed from j=1 to n similarly to the above, so that transmitted light intensity values Itj (j=1, 2, ..., n) are measured at respective wavelengths through the cell 32.

Data analysis is made on the basis of the values Ioj and Itj, to obtain respective component concentrations Ck (k=1, 2, ..., K).

Figure 7:
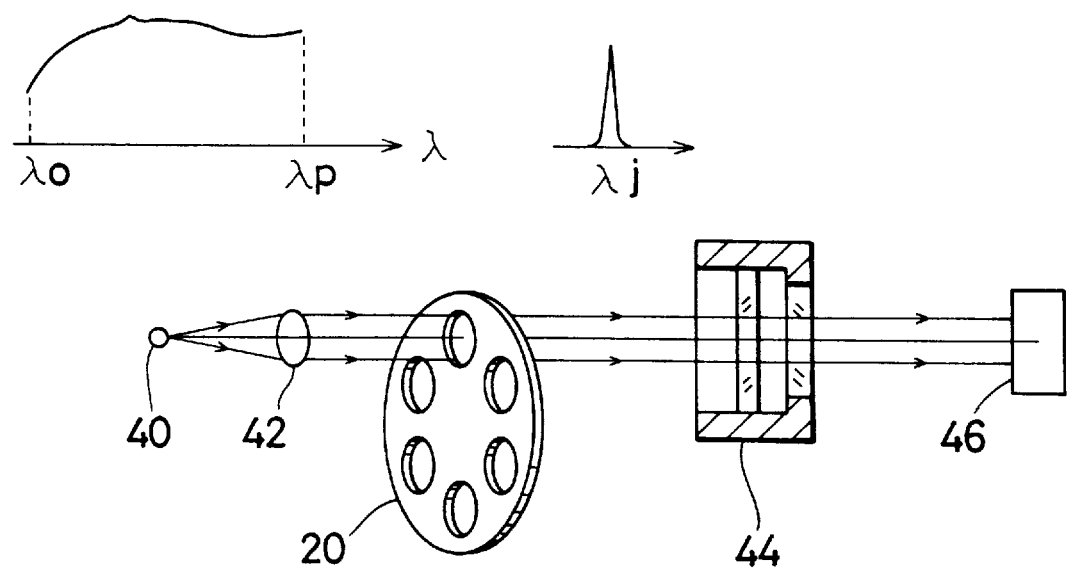
FIG. 7 is a schematic diagram showing a measuring apparatus employing a lamp emitting continuous wavelength light as a light source for previously performing spectroscopic analysis by a filter.

FIG. 7 shows a measuring apparatus employing a lamp source 40 emitting continuous light of a wide wavelength range. The light emitted from the lamp source 40 is converted to a spatial parallel beam by a lens 42 and transmitted through a filter of a wavelength selecting mechanism 20. The measuring beam which is wavelength-selected by transmission through the filter is incident upon a cell 44 which is stored in the sample setting part, so that the beam transmitted through the cell 44 is received by a single photoreceptor 46.

In the measuring apparatus shown in FIG. 7, the wavelength selecting mechanism 20 is first rotated while maintaining the cell 44 in a vacant state for changing the wavelength of the measuring beam which is incident upon the cell 44 from j=1 to n, for measurement of incident light intensity Ioj at each wavelength. Thereafter a urine sample is introduced into the cell 32 and the wavelength selecting mechanism 20 is rotated similarly to the above for changing the wavelength of the measuring beam from j=1 to n, for measurement of transmitted light intensity Itj at each wavelength through the cell 44. Data analysis is made on the basis of the values Ioj and Itj, to obtain respective component concentrations Ck (k=1, 2, ..., K).

Figure 8:
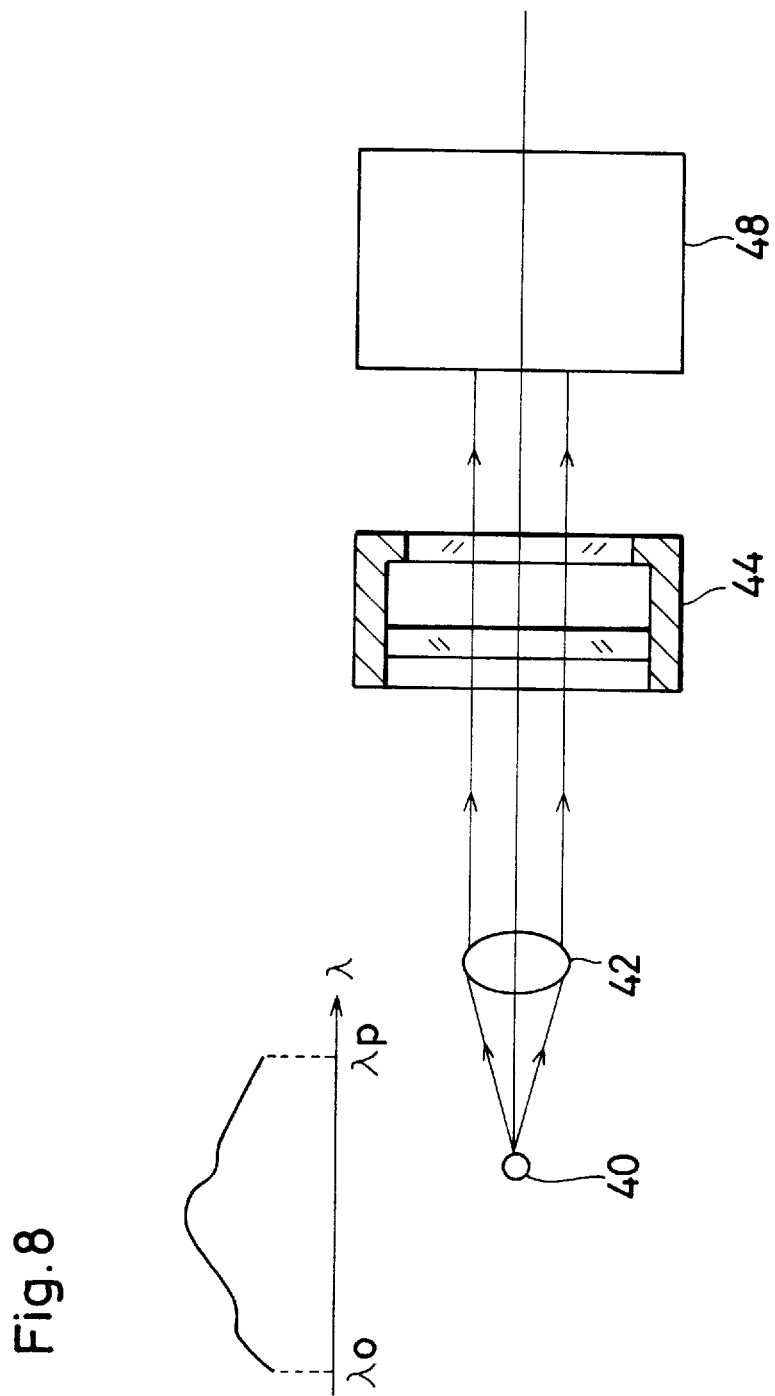
FIG. 8 is a schematic diagram showing a measuring apparatus employing a lamp emitting continuous wavelength light as a light source for subsequently performing spectroscopic analysis by a filter.

FIG. 8 shows an exemplary optical system employing a lamp source 40 emitting light of a wide wavelength region for spectroscopically analyzing the measuring beam after transmission through a cell 44. The measuring beam which is coverted to a spatial parallel beam by a lens 42 is incident upon the cell 44, so that the beam transmitted through the cell 44 is spectroscopically analyzed by a spectroscope 48 and thereafter guided to a photoreceptor.

Also in FIG. 8, the wavelength of the measuring beam is changed from j=1 to n by the spectroscope 48 while maintaining the cell 44 in a vacant state to measure values Ioj, and thereafter a urine sample is introduced into the cell 44 so that the wavelength is changed from j=1 to n by the spectroscope 48 similarly to the above, to measure values Itj. Data analysis is made on the basis of the values Ioj and Itj, to obtain respective component concentrations Ck (k=1, 2, ..., n).

Figure 9:
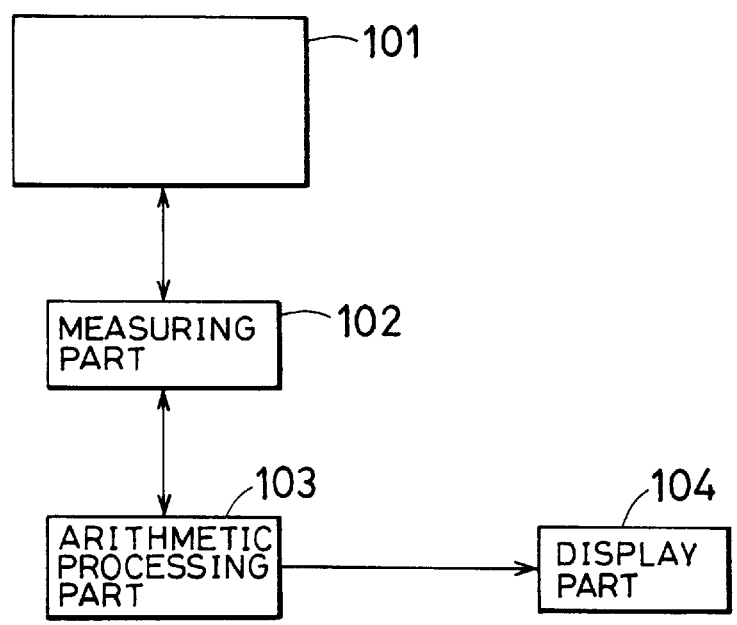
FIG. 9 is a block diagram showing the concept of a uric component measuring apparatus according to the present invention.
Figure 10:
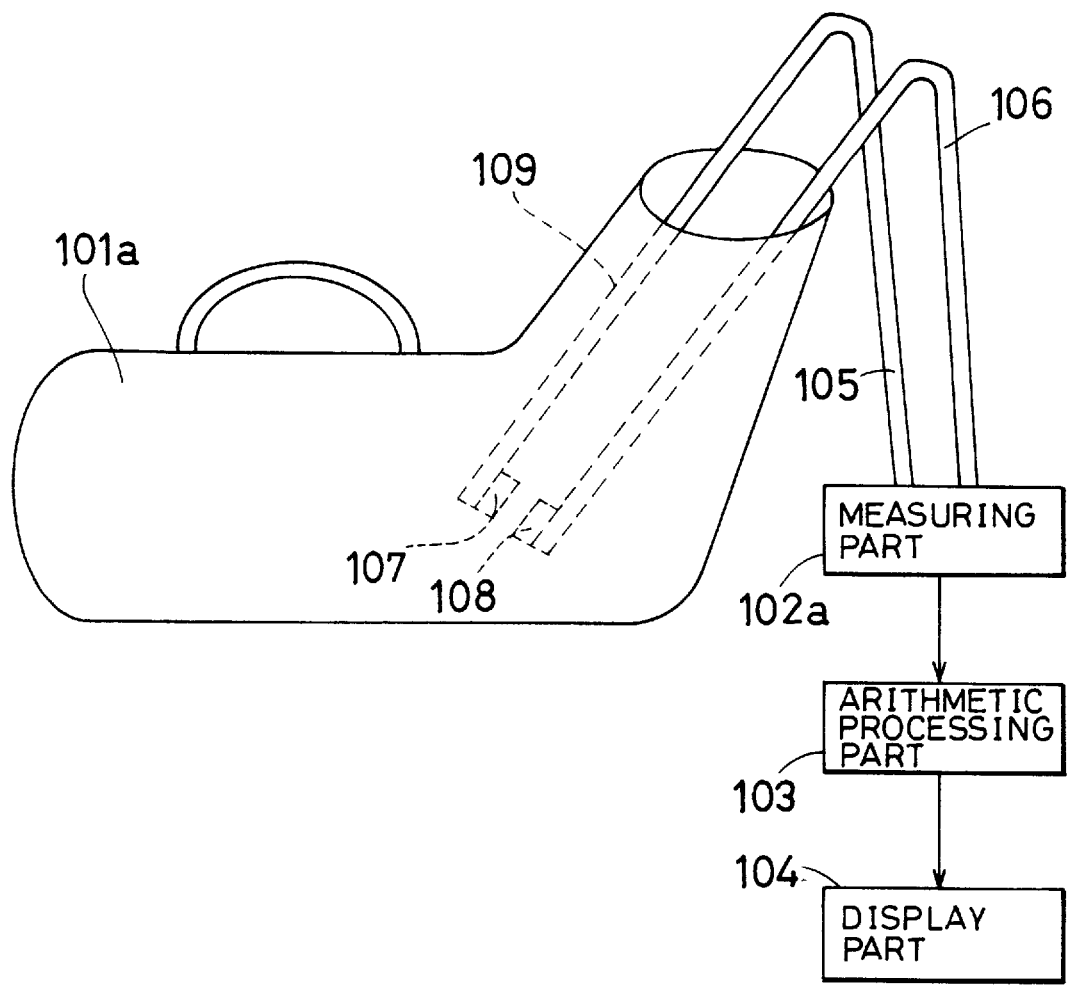
FIG. 10 is a block diagram showing a first embodiment of the uric component measuring apparatus.

FIG. 9 schematically illustrates the uric component measuring apparatus, and FIG. 10 illustrates a first embodiment thereof. Referring to FIG. 10, a bent probe 109 is so provided that the same can be inserted from a measuring part 102a, which is arranged in the exterior of a urinal 101a, into the urinal 101a. The probe 109 includes a light transmission guide path 105 and a light receiving guide path 106, and is provided on its forward end with light transmission and light receiving ends 107 and 108 on the sides of the light transmission and light receiving guide paths 105 and 106 respectively, so that the light transmission and light receiving ends 107 and 108 are dipped in urine which is stored in the urinal 101a. The guide paths 105 and 106 are made of optical fiber, for example, while the light transmission and light receiving ends 107 and 108 are formed by rectangular prisms, for example. The light transmission and light receiving ends 107 and 108 are maintained at a prescribed space, to define a measuring optical path length.

The measuring part 102a comprises a light source part for introducing a measuring beam of the visible or near infrared wavelength region into a base end portion of the light transmission guide path 105, and a light receiving part for receiving and detecting the measuring beam guided by the light receiving guide path 106. The measuring beam received from the light source part passes through the guide path 105, to be emitted from the light transmission end 107. The measuring beam emitted from the light transmission end 107 is incident upon the light receiving end 108, and guided to the light receiving part of the measuring part 102 through the guide path 106. The measuring part 102a measures absorbances of uric components to be measured at measuring wavelengths selected therefor respectively. An arithmetic processing part 103 is adapted to calculate a plurality of uric component concentrations on the basis of the absorbances measured by the measuring part 102a at the plurality of measuring wavelengths. A display part 104 is adapted to output results of the uric component concentrations calculated by the arithmetic processing part 103.

Figure 11:
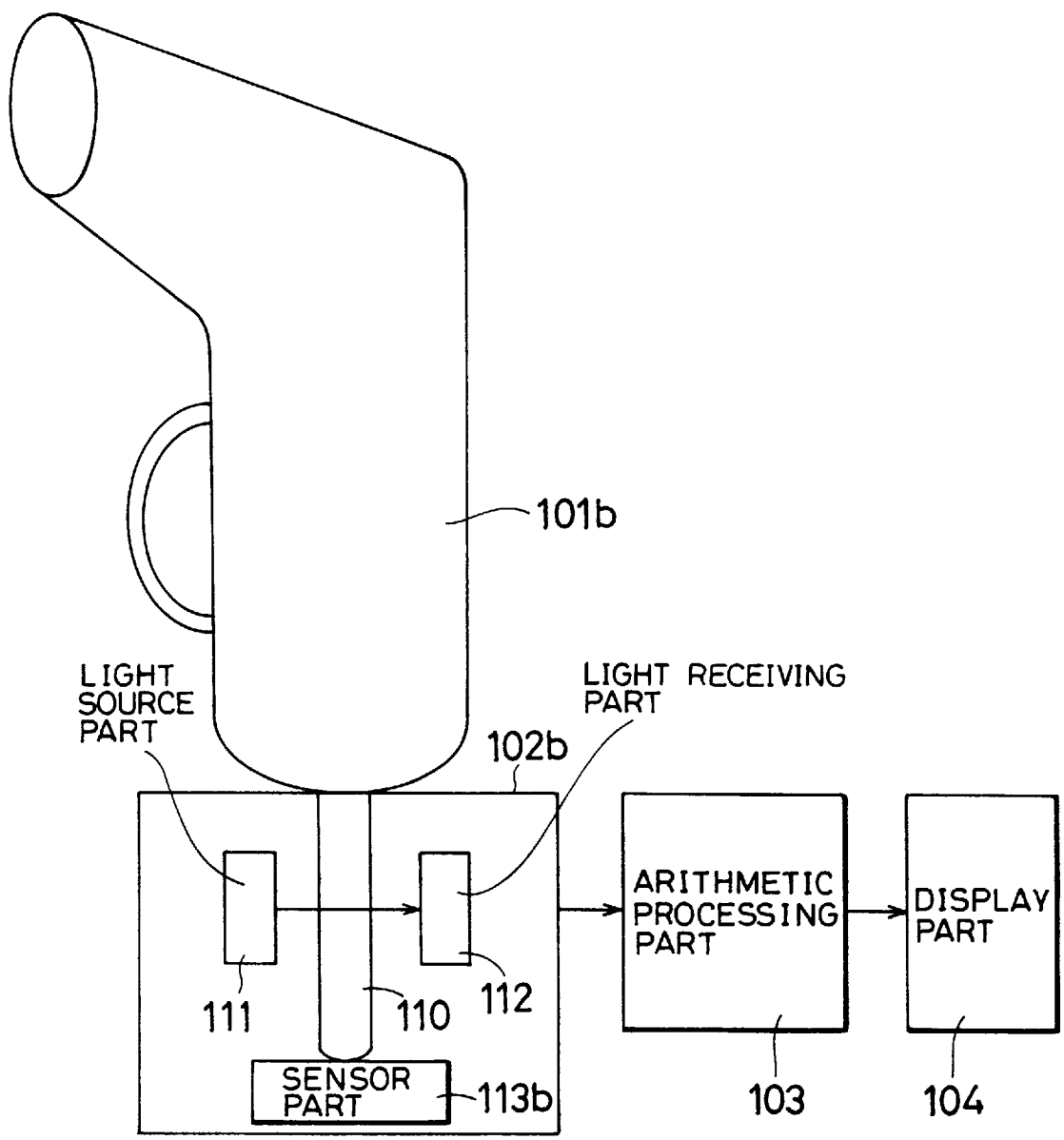
FIG. 11 is a block diagram showing a second embodiment of the uric component measuring apparatus.

FIG. 11 shows a uric component measuring apparatus according to a second embodiment of the present invention.

A urinal 101b comprises a cell 110 on its forward end. The cell 110 internally communicates with the urinal 101b, and outwardly projects from the urinal 101b. This cell 110 is made of a material such as quartz glass or BK7 glass, which transmits light of the visible and near infrared wavelength regions. The cell 110 is so mounted on the urinal 101b that the same is directed toward a forward end, which is opposite to a urine inlet, of the urinal 101b in a horizontal plane on this forward end when the urinal 101b is placed to upwardly direct the urine inlet.

A measuring part 102b has a cell setting part for setting the cell 110 and comprises a light source part 111 for irradiating the cell 110 which is set in the cell setting part with a measuring beam of the visible or near infrared wavelength region, and a light receiving part 112 for receiving and detecting the measuring beam transmitted through the cell 110, for measuring absorbances as to uric components to be measured at measuring wavelengths selected therefor respectively.

The measuring part 102b further comprises a sensor part 113b for optically or mechanically detecting that the cell 110 is set in the cell setting part of the measuring part 102b. The measuring part 102b is so structured as to start its operation on the basis of a signal indicating that the sensor part 113b detects the cell 110. The sensor part 113b can be formed by a pressure sensor, a tilt sensor or an optical sensor. An arithmetic processing part 103 and a display part 104 are identical to those shown in FIG. 10.

Figure 12:
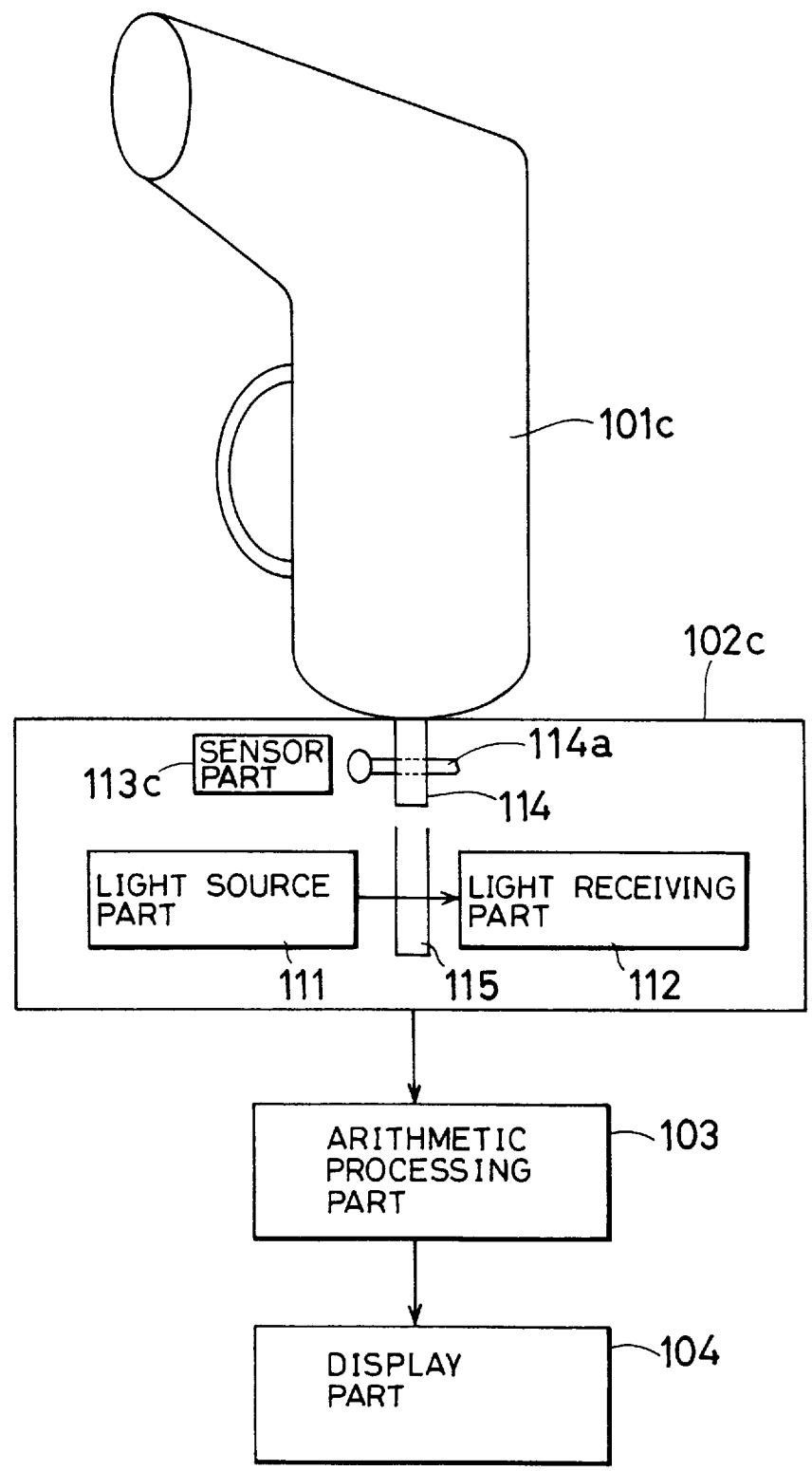
FIG. 12 is a block diagram showing a third embodiment of the uric component measuring apparatus.

FIG. 12 shows a uric component measuring apparatus according to a third embodiment of the present invention.

A urinal 101c has an openable/closable urine discharge nozzle 114, which projects from the body of the urinal 101c. This nozzle 114 is so mounted on the urinal 101c that the same is directed toward a forward end, which is opposite to a urine inlet, of the urinal body in a horizontal plane on the forward end portion when the urinal 101c is placed to upwardly direct the urine inlet. A measuring part 102c comprises a cell 115 in a position for receiving urine which is discharged from the nozzle 114 of the urinal 101c, a light source part 111 for irradiating the cell 115 with a measuring beam of the visible or near infrared wavelength region, and a light receiving part 112 for receiving and detecting the measuring beam transmitted through the cell 115, and measures absorbances as to respective ones of uric components at measuring wavelengths selected therefor respectively. The nozzle 114 is an electromagnetic nozzle which is opened/closed by an electromagnetic valve 114a. The measuring part 102c further comprises a sensor part 113c for optically or mechanically detecting that the nozzle 114 is set in a prescribed position of the measuring part 102c. The electromagnetic valve 114a is opened for a constant time on the basis of a signal indicating that the sensor part 113c detects the nozzle 114.

In each of the embodiments shown in FIGS. 10 to 12, the light source part 111 which is provided in the measuring part 102a, 102b or 102c comprises a laser diode array emitting laser beams of measuring wavelengths, a light emitting diode array emitting light beams of measuring wavelengths, a laser unit having a variable oscillation wavelength, or a lamp source emitting light of a continuous wavelength. The light receiving part 112 is provided with an array type photoreceptor of CCD, a photoreceptor array or a single photoreceptor as a detector. When a variable-wavelength laser unit or a lamp of a continuous wavelength is employed in the light source part 111 as a light source, no optical system is required for mixing beams since only a single optical path is derived from the light source. When a laser diode array or a light emitting diode array is employed, however, an optical system such as that shown in FIGS. 2(A) or 2(B) is required for the light source part 111, in order to arrange a measuring beam of a selected wavelength on a measuring optical path. The cell 110 or 115 can be formed by that shown in FIGS. 3(A), 3(B) or 3(C). The detector provided in the light receiving part 112 can be formed by that shown in FIGS. 4(A), 4(B) or 4(C). When a lamp source emitting continuous wavelength light is employed as the light source of the light source part 111, it is necessary to spectroscopically analyze the beam every wavelength selected for each uric component before incidence upon the sample or after transmission through the sample. The spectroscopic means therefor can be formed by that shown in FIGS. 5(A) or 5(B).

The operations of the embodiments shown in FIGS. 10 to 12 are now described.

In the measuring apparatus shown in FIG. 105 the measuring operation is first started in a state that the forward end of the probe 109 is in the air, so that the measuring beam is transmitted from the measuring part 102a and the measuring wavelength λj is changed from j=1 to n for measurement of current transmitted light quantities Ioj (j=1, 2, . . . , n).

Then, the probe 109 is inserted in the urinal 101a storing urine, to dip the light transmission and light receiving ends 107 and 108 in the urine. The measuring operation is started similarly to the above, so that the measuring beam is similarly transmitted from the measuring part 102a and the measuring wavelength λj is changed from j=1 to n for measurement of transmitted light quantities Itj (j=1, 2, . . . , n).

The arithmetic processing part 103 carries out data analysis on the basis of the values Ioj and Itj, obtains the respective component concentrations Ck (k=1, 2, . . . , K), and displays the same on the display part 104.

In the measuring apparatus shown in FIG. 11, the cell 110 is first set in the cell setting part of the measuring part 102b in a state that the urinal 101b as well as the cell 110 are vacant. When the cell 110 is thus set in the cell setting part, the sensor part 113b generates a detection signal so that the measuring part 102b starts its measuring operation, and the measuring beam is incident upon the cell 110 from the light source part 111 so that the measuring beam transmitted through the cell 110 is received by the light receiving part 112. At this time, the measuring wavelength λj is changed from j=1 to n, so that transmitted light quantities Ioj (j=1, 2, . . . , n) are measured.

Then, urine is introduced into the urinal 101b and the cell 110 is again set in the cell setting part of the measuring part 102b, so that the sensor part 113b similarly generates a detection signal and the measuring part 102b starts its measuring operation. Also at this time, the measuring beam is incident upon the cell 110 from the light source part 111, so that the measuring beam transmitted through the cell 110 is received by the light receiving part 112. Also at this time, the measuring wavelength λj is changed from j=1 to n, so that transmitted light quantities Itj (j=1, 2, . . . , n) are measured. The arithmetic processing part 103 carries out data analysis on the basis of the values Ioj and Itj, obtains respective component concentrations Ck (k=1, 2, . . . , K), and displays the same on the display part 104.

In the measuring apparatus shown in FIG. 12, the nozzle 114 is first set in a prescribed position of the measuring part 102c in a state that the urinal 101c is vacant. When the nozzle 114 is thus set in the prescribed position, the sensor part 113c generates a detection signal to open the electromagnetic valve 114a for a constant time, while no urine sample is injected into the cell 115 since the urinal 101c is vacant. Thereafter the measuring part 102c starts its measuring operation on the basis of the detection signal from the sensor part 113c, so that a measuring beam is incident upon the vacant cell 115 from the light source part 111 and the measuring beam transmitted through the cell 115 is received by the light receiving part 112. At this time, the measuring wavelength λj is changed from j=1 to n, so that transmitted light quantities Ioj (j=1, 2, . . . , n) are measured.

Then, urine is introduced into the urinal 101c and the nozzle 114 is again set in the prescribed position of the measuring part 102c, so that the sensor part 113c similarly generates a detection signal to open the electromagnetic valve 114a for a constant time and the urine sample is injected from the nozzle 114 into the cell 115. Thereafter the measuring part 102c starts its measuring operation on the basis of the detection signal from the sensor part 113c, so that the measuring beam is incident upon the cell 115 from the light source part 111 and the measuring beam transmitted through the cell 115 is received by the light receiving part 112. Also at this time, the measuring wavelength λj is changed from j=1 to n, so that transmitted light quantities Itj (j=1, 2, . . . , n) are measured. The arithmetic processing part 103 carries out data analysis on the basis of the values Ioj and Itj, obtains respective component concentrations Ck (k=1, 2, . . . , K), and displays the same on the display part 104.

A stool according to the present invention is roughly classified into a local analyzing system which comprises a data analysis part for calculating a plurality of uric component concentrations to be measured and displaying the same by units provided on the stool, and a host analyzing system implementing a data analysis part by a host computer etc. provided on the exterior of the stool, which in turn comprises a data transmission part for transmitting data measured in a measuring part to the data analysis part and receiving uric component concentrations calculated in the data analysis part.

Figure 13:
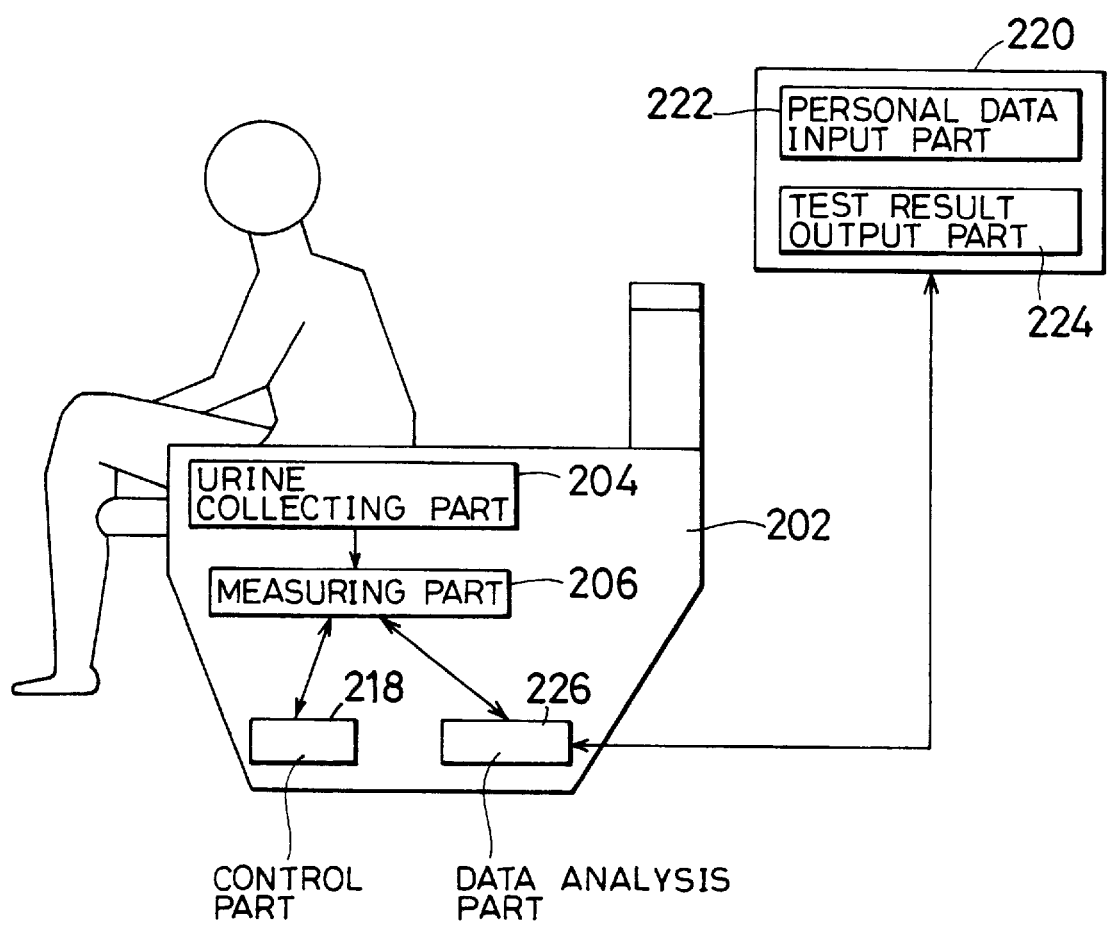
FIG. 13 is a block diagram schematically showing a first embodiment of a stool according to the present invention.
Figure 14:
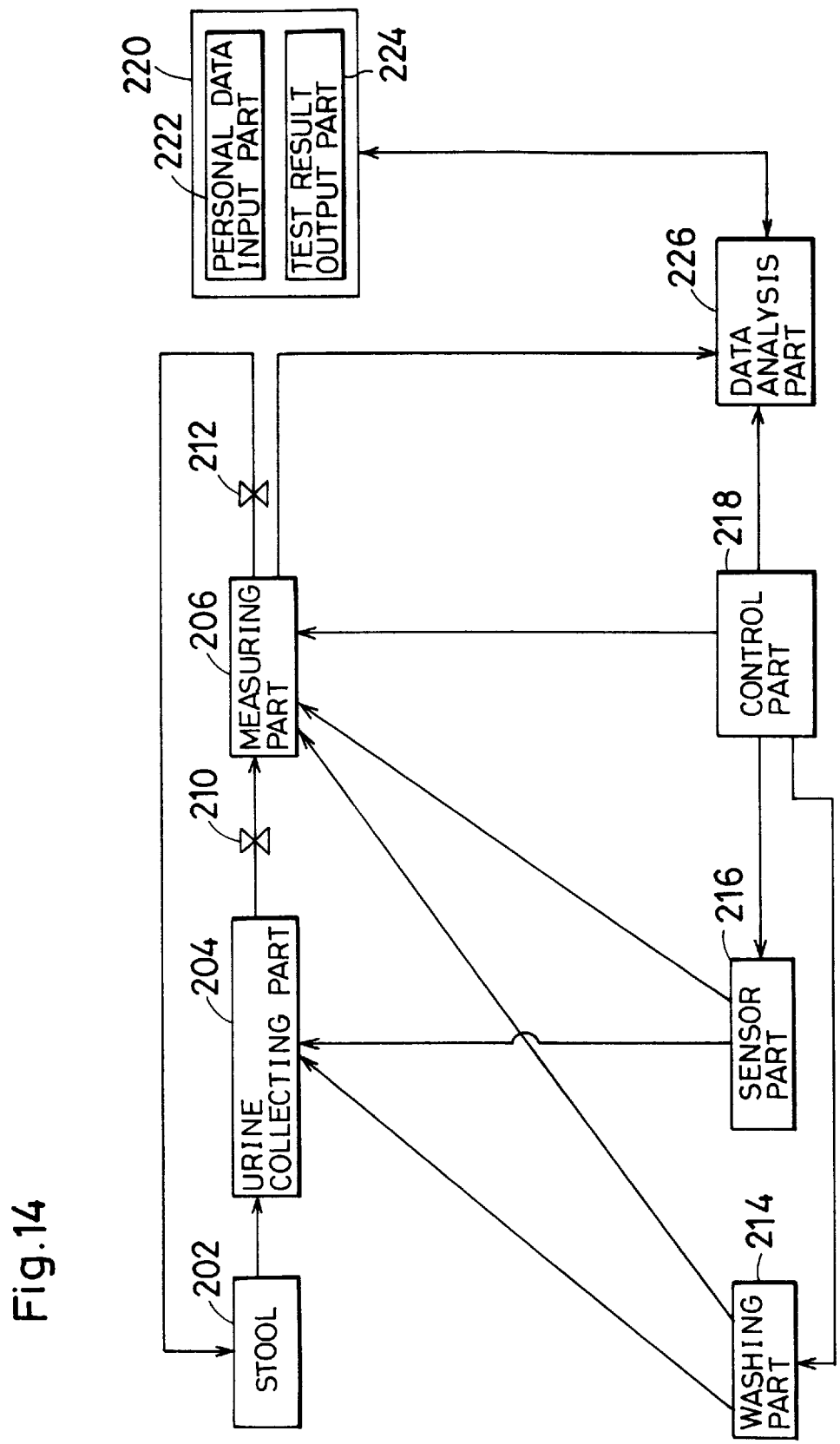
FIG. 14 is a block diagram showing the embodiment.

FIGS. 13 and 14 schematically illustrate an embodiment of the local analyzing system.

FIG. 13 illustrates a Western style stool body 202, which may alternatively be formed by a Japanese style stool or a urinal. The stool body 202 is provided on a position for receiving urine with a urine collecting part 204, so that urine collected by the urine collecting part 204 is transmitted to a cell of a measuring part 206 which is provided on the stool body 202. A valve 210 for intermitting supply of the urine to the cell is provided on a passage for supplying the urine to the cell of the measuring part 206. The measuring part 206 is provided with the cell for receiving the urine collected in the urine collecting part 204, a light source part for irradiating the cell with a measuring beam of the visible or near infrared wavelength region, and a light receiving part for receiving and detecting the measuring beam transmitted through the cell, for measuring absorbances as to uric components to be measured at measuring wavelengths selected therefor respectively. The urine transmitted to the measuring part 206 passes through the cell and is discharged into a discharge pipe 238 (see FIG. 17) through a valve 212.

A washing part 214 is provided for the urine collecting part 204 and the cell of the measuring part 206, and programmed to wash the urine collecting part 204 and the cell of the measuring part 206 at predetermined points of time such as before starting and after completion of measurement of each sample. The sensor part 216 is adapted to detect soiling of the urine collecting part 204 and the cell of the measuring part 206, and so programmed that the urine collecting part 204 and the cell are washed also when the sensor part 216 detects that soiling of the urine collecting part 204 or the cell is in excess of a previously set level. The urine collecting part 204 can be made of transparent glass, for example, while the sensor part 216 can comprise a light source part for emitting a measuring beam for detecting soiling of the urine collecting part 204 and a light receiving part for receiving and detecting the measuring beam transmitted through the urine collecting part 204 and measuring its absorbance, so that the degree of soiling of the urine collecting part 204 is decided from the absorbance. The sensor part 216 for the cell of the measuring part 206 may comprise a light source part and a light receiving part for detecting the degree of soiling similarly to the urine collecting part 204, or may utilize the light source part and the light receiving part for obtaining uric component concentrations in the measuring part 206, for measuring the absorbance of the cell itself and deciding the degree of soiling of the cell.

A control part 218 is adapted to control operations of the urine collecting part 204, the measuring part 206, the valves 210 and 212, the washing part 214 and the sensor part 216.

An input/output part 220 comprises a personal data input part 222 for inputting individual data such as identification data of a testee such as the name, age and sex and measurement items, and a test result output part 224 for displaying test results by data analysis in the data analysis part 226 as well as a measuring operation error.

The data analysis part 226, which is formed by a CPU, a ROM and a RAM, receives absorbances measured at a plurality of measuring wavelengths from the measuring part 206 as to uric components corresponding to the measurement items input from the personal data input part 222, and calculates concentrations of the respective uric components on the basis thereof. The uric component concentrations as calculated are transmitted to and output from the test result output part 224.

In the local analyzing system, the urine collecting part 204, the measuring part 206, the control part 218 and the data analysis part 226 are mounted on the stool body 202, while the washing part 214 and the sensor part 216 are provided on the urine collecting part 204 and the measuring part 206. The input/output part 220 is provided independently of the stool body 202.

Figure 15:
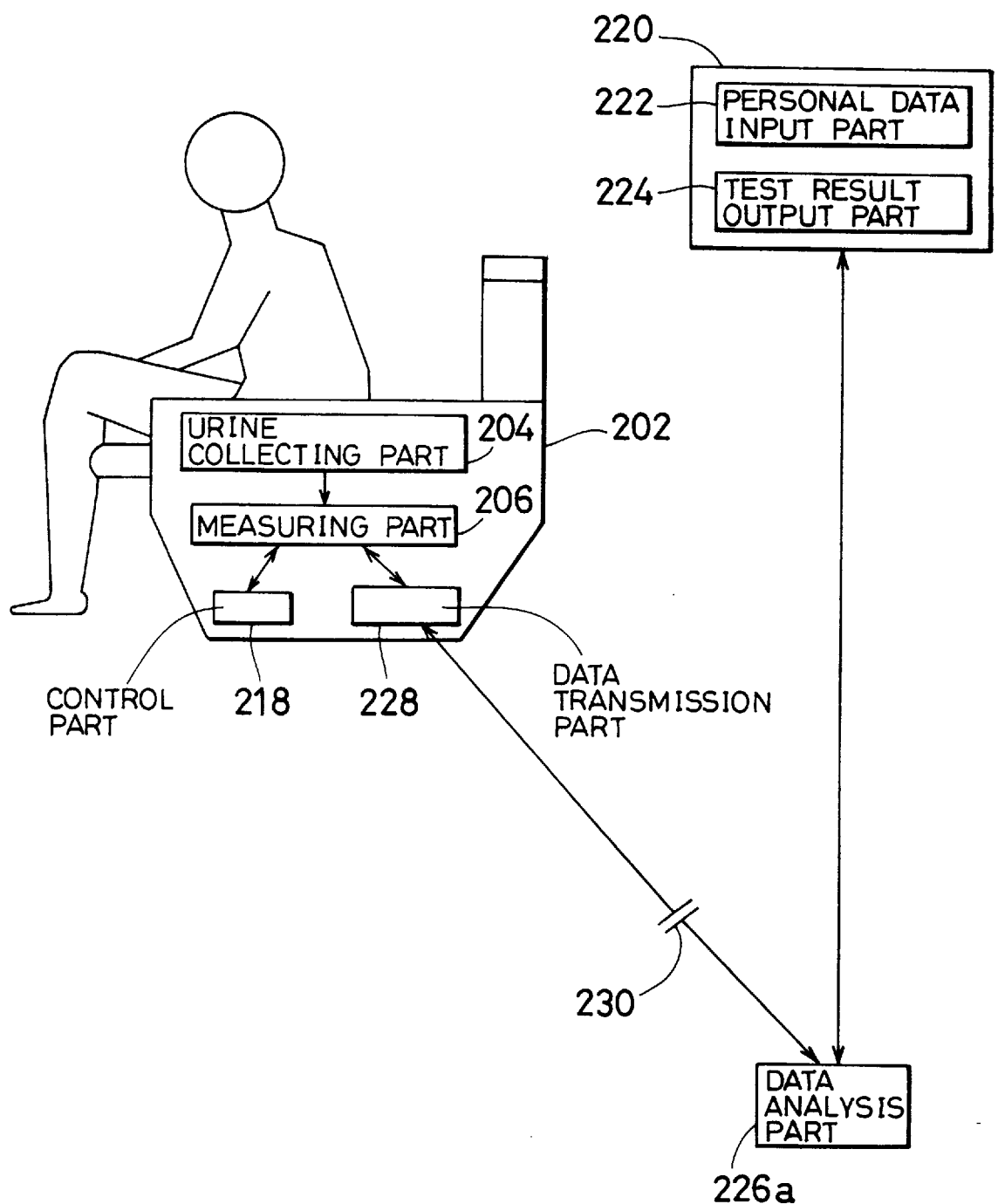
FIG. 15 is a block diagram schematically showing a second embodiment of the stool according to the present invention.
Figure 16:
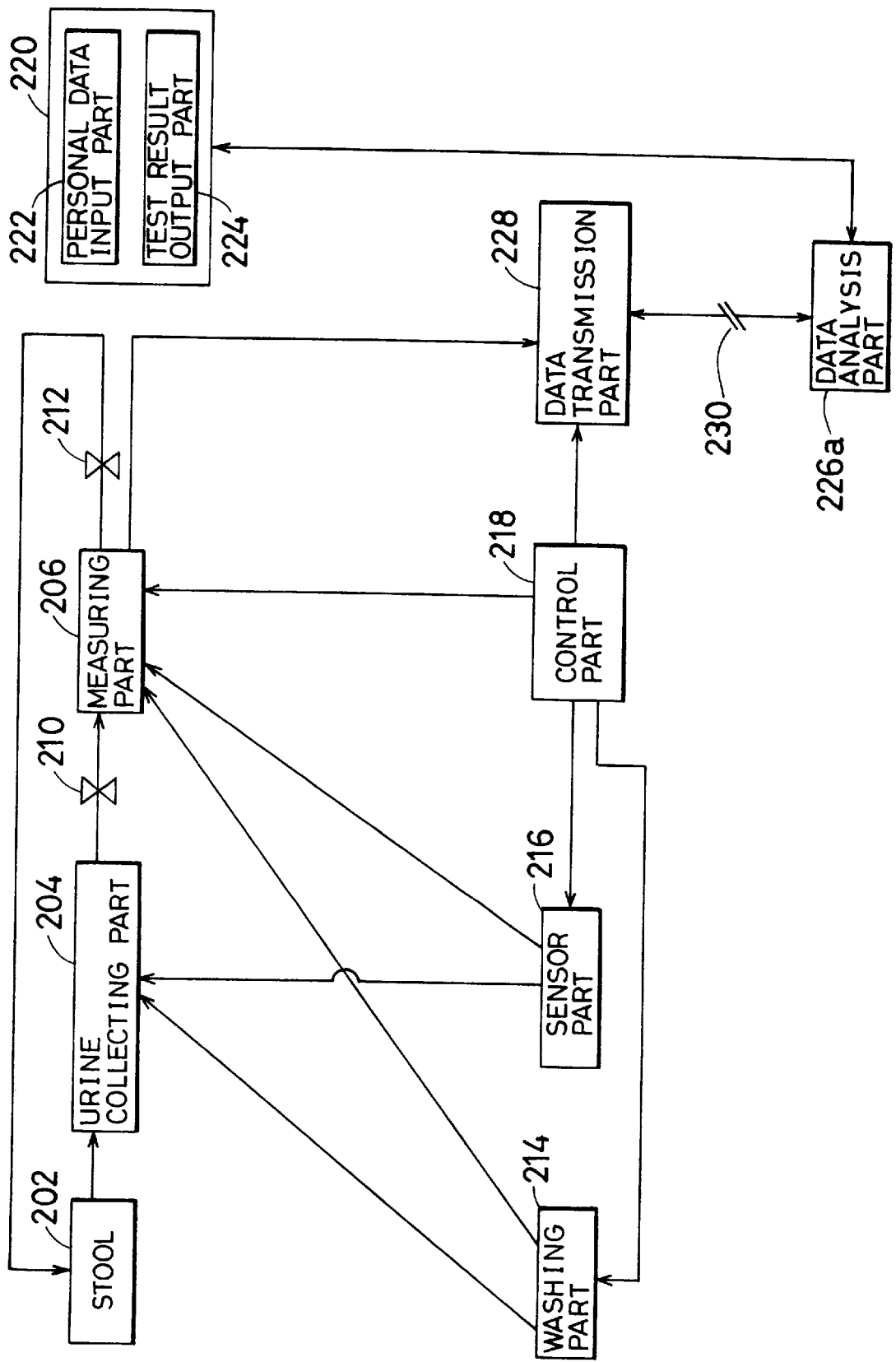
FIG. 16 is a block diagram showing the embodiment.

FIGS. 15 and 16 schematically illustrate an embodiment of the host analyzing system.

This embodiment is different from that shown in FIGS. 13 and 14 in a point that a data analysis part 226a is implemented by an external host computer. Absorbance data obtained in the measuring part 206 are transferred to the host computer serving as the data analysis part 226a by a data transmission part 228 through a communication line 230, while data such as measurement items input from the personal data input part 222 are also transferred to the host computer serving as the data analysis part 226a through the communication line 230. A plurality of uric component concentration data calculated by the data analysis part 226a through multivariate analysis or the like are transmitted to the test result output part 224 through the communication line 230 and output.

In the host analyzing system, the urine collecting part 204, the measuring part 206, the control part 218 and the data transmission part 228 are mounted on the stool body 202. Similarly to the local analyzing system, the washing part 214 and the sensor part 216 are provided on the urine collecting part 204 and the measuring part 206, while the input/output part 202 is provided independently of the stool body 202. The data analytical part 226a is the host computer which is independent of the stool body 202. The remaining structure of this embodiment is identical to that shown in FIGS. 13 and 14.

Figure 17:
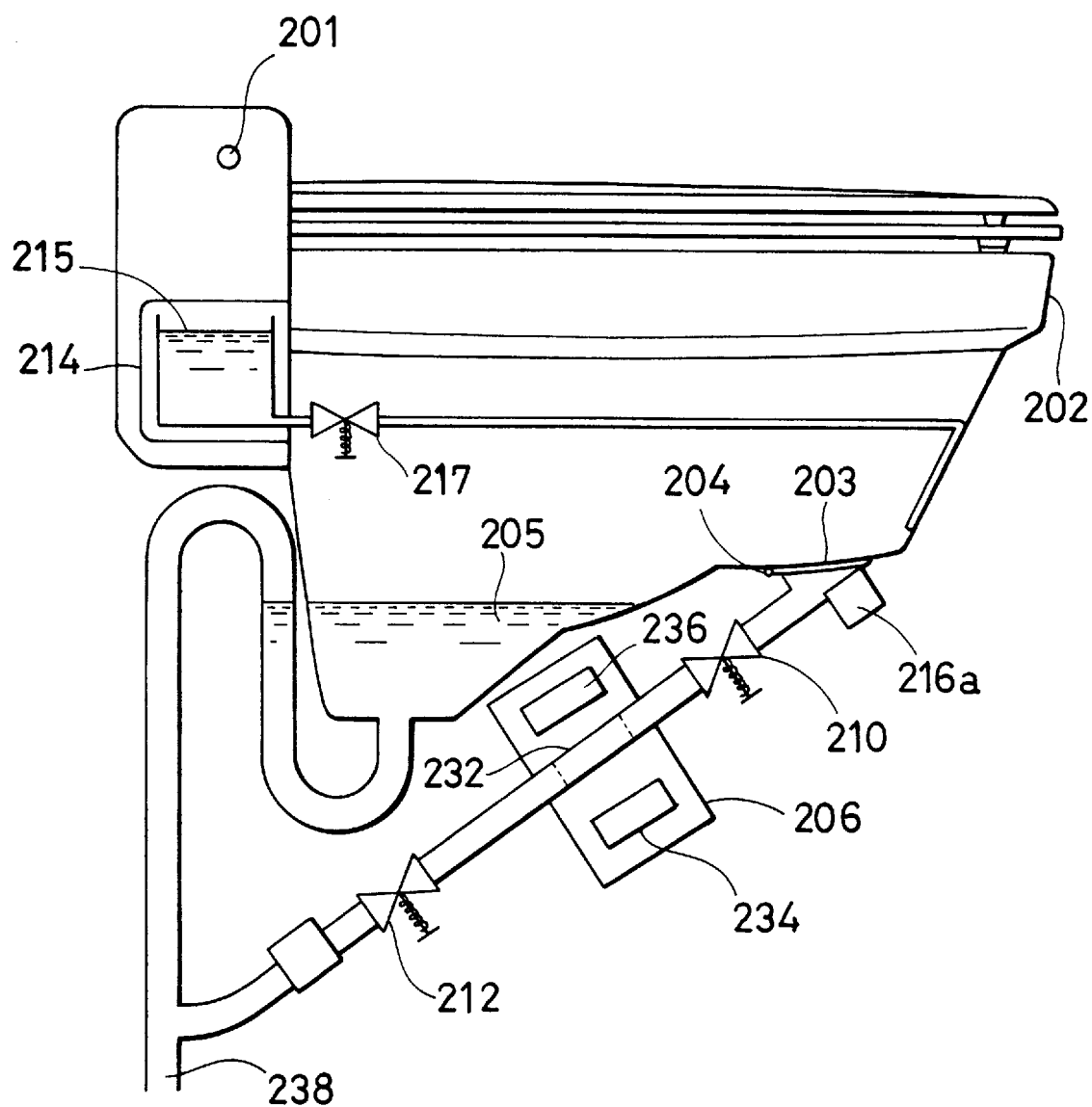
FIG. 17 is a sectional view showing a stool body, a urine collecting part and a measuring part in each embodiment of the stool.

FIG. 17 illustrates the stool body 202, the urine collecting part 204 and the measuring part 206 provided in each of the embodiments shown in FIGS. 13 to 16. The measuring part 206 which is mounted on the stool body 202 is provided with a flow cell 232, so that urine is transmitted from the urine collecting part 204 provided in the stool body 202 through a passage while the urine passed through the flow cell 232 is discharged to the discharge pipe 238. The urine collecting part 204 is provided with a cover 203, which is opened by a command from the control part 218 when urine is collected, the urine collecting part 204 is washed, and the flow cell 232 is washed. The urine collecting part 204 is provided with a sensor part 216a. Electromagnetic valves 210 and 212 are provided in passages from the urine collecting part 204 to the flow cell 232 and from the flow cell 232 to the discharge pipe 238 respectively.

A light source part 234 is provided for irradiating the flow cell 232 with a measuring beam, while a light receiving part 236 is provided for receiving and detecting the measuring beam transmitted through the flow cell 232. The light source part 234 and the light receiving part 236 serve both as means for measuring absorbances of a urine sample flowing through the flow cell 236 at the measuring part 206 and sensors for detecting soiling of the flow cell 236.

A washing solution 215 is stored in a washing solution vessel of the washing part 214 which is provided on a side portion of the stool body 202, while a washing solution discharge pipe is connected to a lower portion of the washing solution vessel through an electromagnetic valve 217. An outlet of the washing solution discharge pipe is arranged oppositely to the urine collecting part 204, so that the washing solution 215 which is discharged from the outlet of the washing solution discharge pipe flows into the urine collecting part 204 when the cover 203 thereof is opened. The cover 203 of the urine collecting part 204 is opened when the sensor part 216a detects soiling of the urine collecting part 204, the sensor part of the measuring part 206 detects soiling of the flow cell 232, and the urine collecting part 204 and the flow cell 232 are washed in other case, so that the electromagnetic valve 217 is opened and the washing solution 215 flows into the urine collecting part 204 and the flow cell 232.

A communicating tube meandering in a vertical plane to be capable of collecting discharge water 205 and communicating with the discharge pipe 238 is connected to a bottom portion of the stool body 202, so that the stool body 202 is used as an ordinary stool when the cover 203 of the urine collecting part 204 is closed.

A switch 201 which is provided on a side portion of the stool body 202 in proximity to the washing part 214 is a measuring switch for starting the measuring operation.

A mechanism for supplying the discharge water 205 is also provided independently of the washing part 214 for the washing solution 215.

The light source part 234 provided on the measuring part 206 comprises a laser diode array emitting laser beams of measuring wavelengths, a light emitting diode array, a laser unit having a variable oscillation wavelength, or a lamp source emitting light of a continuous wavelength. The light receiving part 236 is provided with an array type photoreceptor of CCD, a photoreceptor array or a single photoreceptor as a detector. When a variable-wavelength laser unit or a lamp of a continuous wavelength is employed in the light source part 234 as a light source, no optical system is required for mixing beams since only a single optical path is derived from the light source. When a laser diode array or a light emitting diode array is employed, however, an optical system such as that shown in FIGS. 2(A) or 2(B) is required for the light source part 234, in order to arrange a measuring beam of a selected wavelength on a measuring optical path. The flow cell 232 provided in the measuring part 206 is formed by that which can singularize or vary its optical path length, as shown in FIGS. 3(A), 3(B) or 3(C). The detector provided in the light receiving part 236 can be formed by that shown in FIG. 4(A), 4(B) or 4(C). When a lamp source emitting continuous wavelength light is employed as the light source of the light source part 234, it is necessary to spectroscopically analyze the beam every wavelength selected for each uric component before incidence upon the sample or after transmission through the sample. The spectroscopic means therefor can be formed by that shown in FIGS. 5(A) or 5(B).

Figure 18:
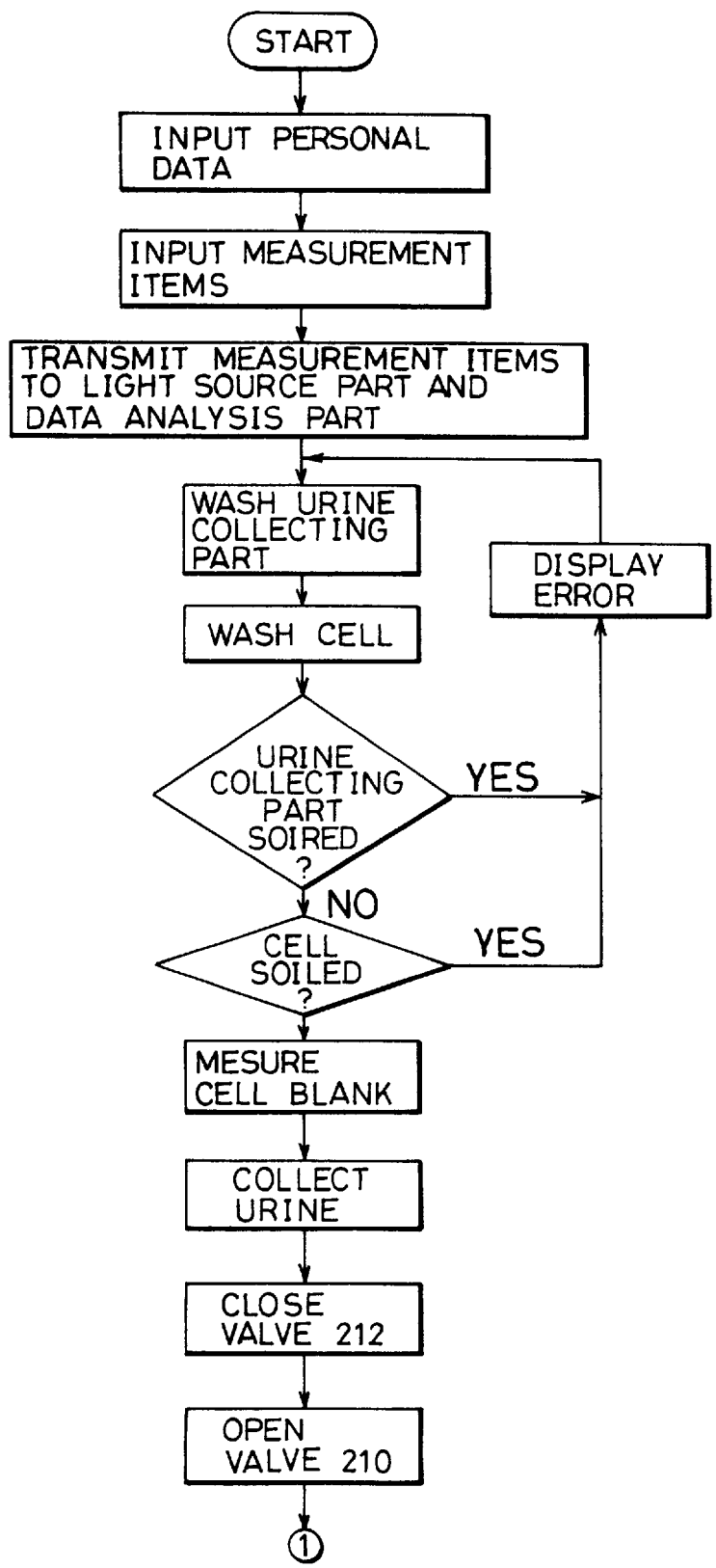
FIG. 18 is a flow chart showing a first half operation of the first embodiment of the stool.
Figure 19:
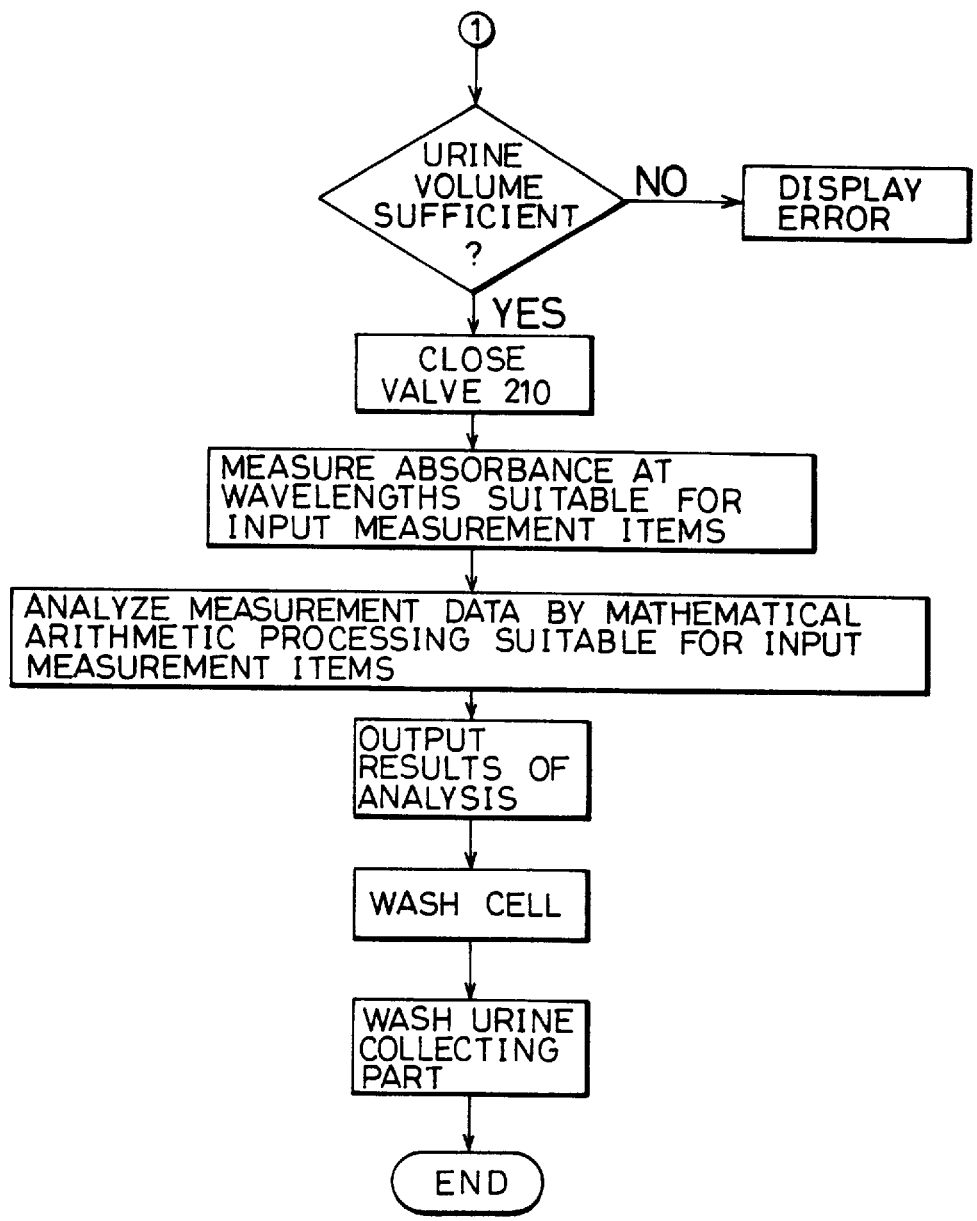
FIG. 19 is a flow chart showing a second half operation of the embodiment.

The operation of each of the embodiments shown in FIGS. 13 to 17 is now described with reference to FIGS. 18 and 19.

Personal data and measurement items are input from the personal data input part 222. Since measuring wavelengths are set by the measurement items, the measurement items are transmitted to the light source part of the measuring part 206 and the data analysis part 226 or 226a.

When the measuring switch 201 is pressed, the urine collecting part 204 and the cell 232 are washed first, degrees of soiling of the urine collecting part 204 and the cell 232 are checked by the sensor part 216 (the sensor part 216a of the urine collecting part 204 and the measuring part 206 serving for a cell sensor part) so that an error is displayed when a determination is made that the urine collecting part 204 is soiled in excess of a previously set level, and the urine collecting part 204 and the cell 232 are again washed. Such washing is repeated until the urine collecting part 204 enters a measurable state, and thereafter the degree of soiling of the cell 232 is checked by the sensor part 216 so that an error is displayed also when a determination is made that the cell 232 is soiled in excess of a previously set level, and the washing of the urine collecting part 204 and the cell 232 is repeated until the cell 232 enters a measurable state. When both of the urine collecting part 214 and the cell 232 enter measurable states, the measurable states are displayed in place of the errors.

When the measurable states are attained, cell blank measurement is carried out first. In this cell blank measurement, the measuring part 206 starts its measuring operation in such a state that the cell 232 is vacant or stores water. In this measurement, absorbances are measured at a plurality of measuring wavelengths which are selected to be suitable for uric components corresponding to the measurement items input from the personal data input part 222. The cell 232 is irradiated with a measuring beam emitted from the light source part 234, so that the measuring beam transmitted through the cell 232 is received by the light receiving part 236. At this time, the measuring wavelength $\lambda j$ is changed from j=1 to n, so that transmitted light quantities Ioj (j=1, 2, . . . , n) are measured.

Thereafter urine collection is started, to collect urine in the urine collecting part 204. The valve 212 is closed and the valve 210 is opened, to measure the urine volume. If the urine volume is insufficient for the measurement, an error is displayed and no measurement of uric components is performed.

If the urine volume is sufficient, on the other hand, the valve 210 is closed and thereafter absorbances are measured at the plurality of measuring wavelengths which are selected to be suitable for the uric components corresponding to the measurement items input from the personal data input part 222. Also at this time, the cell 232 is irradiated with the measuring beam from the light source part 234, so that the measuring beam transmitted through the cell 232 is received by the light receiving part 236. Also at this time, the measuring wavelength $\lambda j$ is changed from j=1 to n, so that transmitted light quantities Itj (j=1, 2, ..., n) are measured.

The data analysis part 226 or 226a analyzes measurement data by mathematical arithmetic processing such as multivariate analysis on the basis of the absorbances Ioj and Itj measured in the measuring part 206, to obtain the respective component concentrations Ck (k=1, 2, ..., K). The results of analysis are output at the test result output part 224. Thereafter the urine collecting part 204 and the cell 232 are washed to complete single measurement.

The difference between the operations of the embodiments shown in FIGS. 13 to 16 simply resides in whether the absorbance data are analyzed in the data analysis part 226 provided on the stool body 202 or transmitted to the external data analysis part 226a through the data transmission part 228 for data analysis, and the remaining parts of the operations of these embodiments are identical to each other.

Results of individual measurement as to some components contained in urine are now described.

Figure 20:
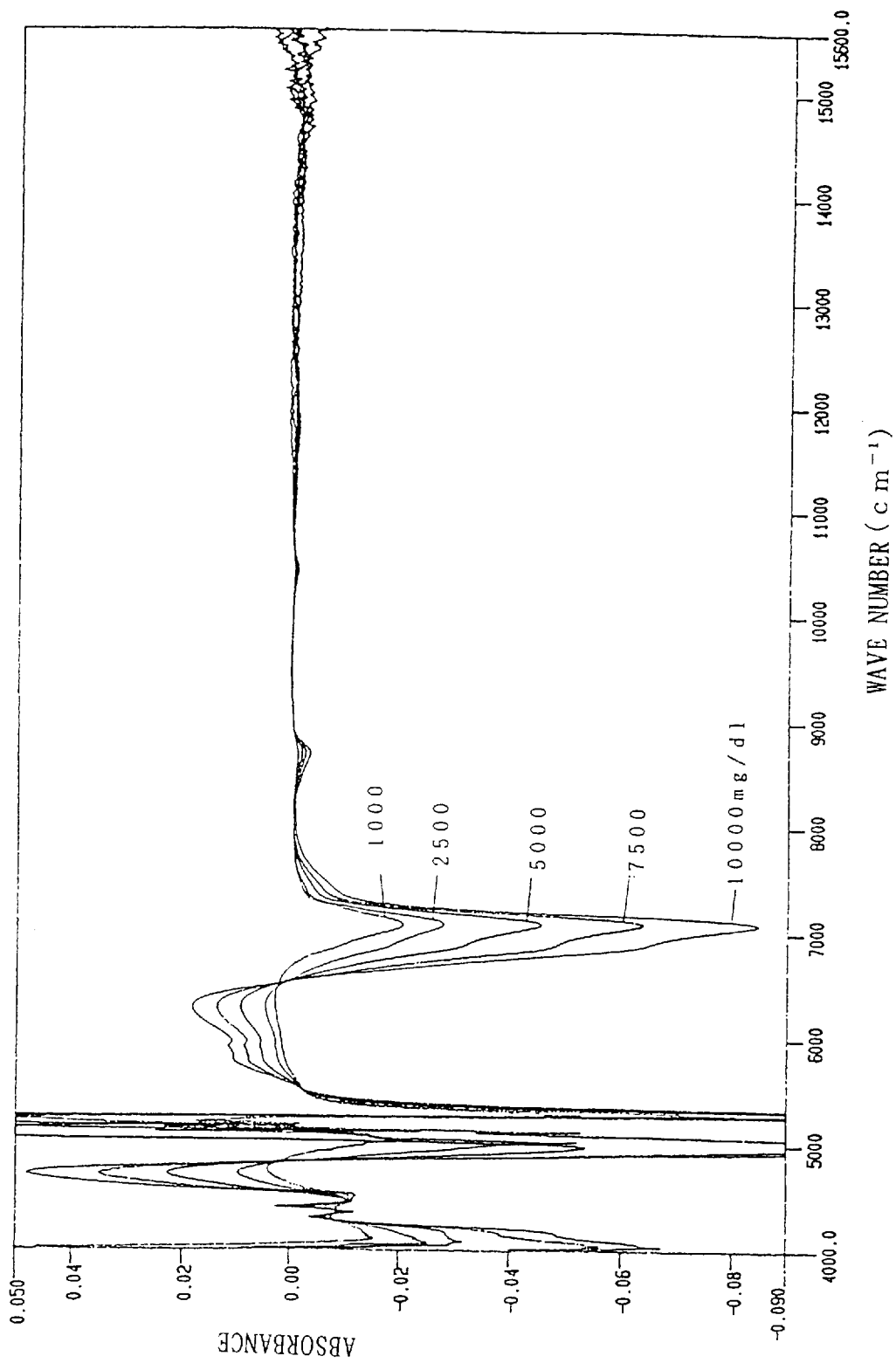
FIG. 20 illustrates spectra of a plurality of samples of aqueous glucose solutions having different concentrations.
Figure 21:
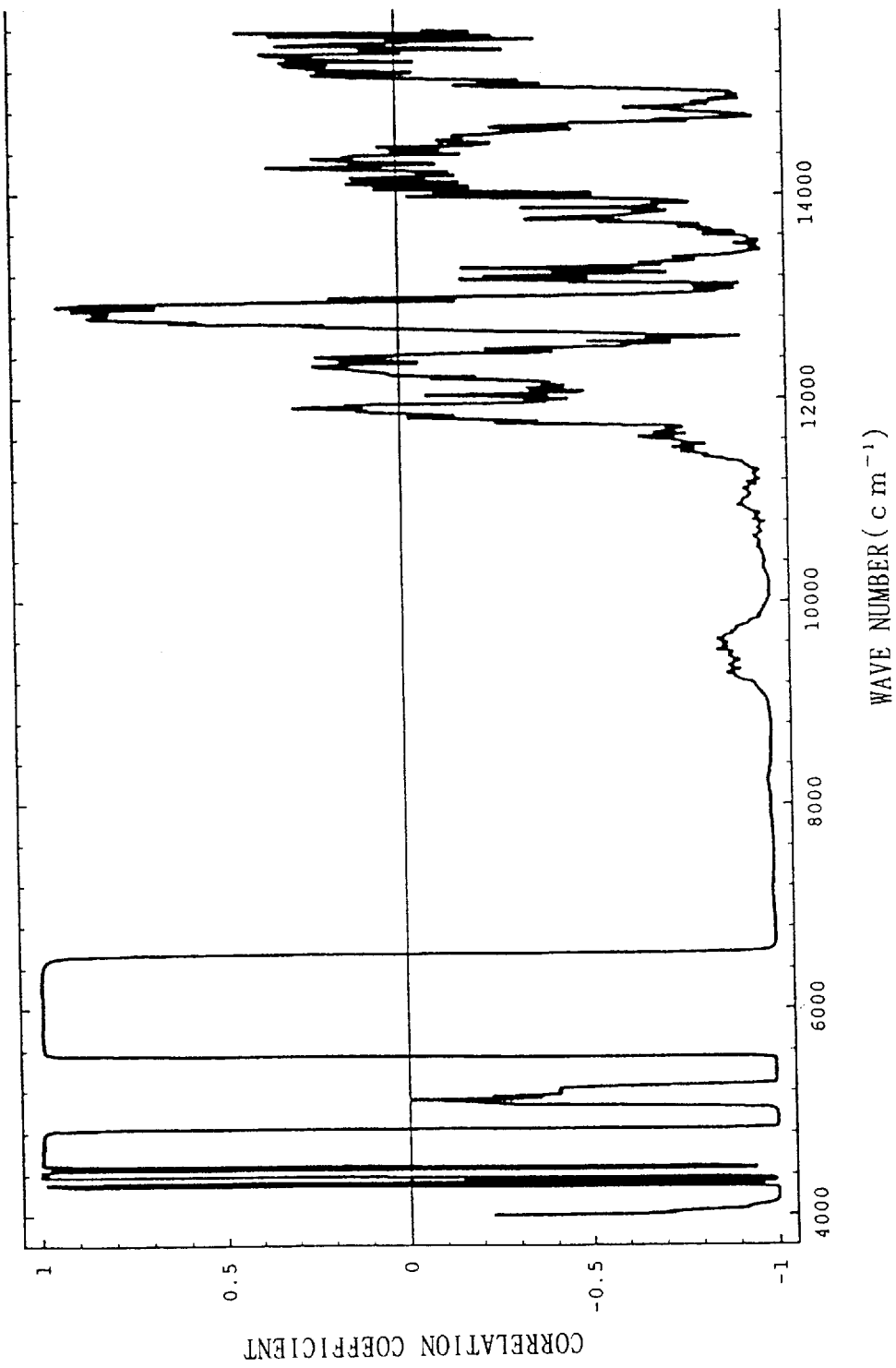
FIG. 21 illustrates wavelength distribution of correlation coefficients (absorbance-concentration) between absorbances and concentrations of an aqueous glucose solution.
Figure 22:
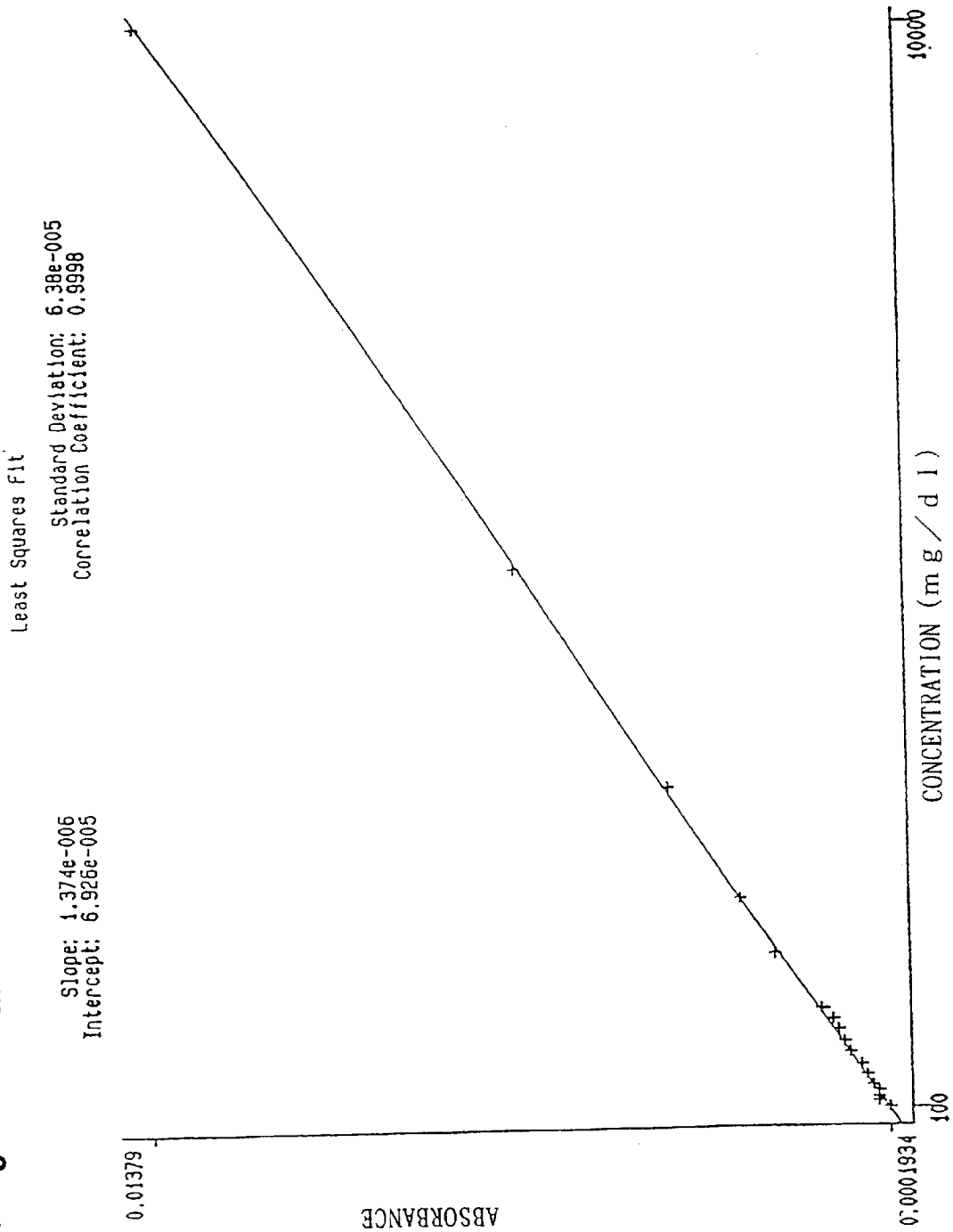
FIG. 22 illustrates a calibration curve showing relation between the concentration and the absorbance of an aqueous glucose solution at 4398 $cm^{-1}$.

FIGS. 20 to 22 show measurement results of aqueous glucose solutions. FIG. 20 illustrates spectra of a plurality of samples having different concentrations, and a region overranging indication around 5000 $cm^{-1}$ is a water absorbing region. Due to the measurement on the plurality of samples having different concentrations, a plurality of spectra are illustrated in an overlapped manner. FIG. 21 shows wavelength distribution of correlation coefficients (absorbance-concentration) obtained from these spectra. The spectra shown in FIG. 20 are corrected on the basis of absorbances in a region having correlation coefficients of not more than 0.1 regarded as a reference wavelength region.

Wavelength regions having absolute values of correlation coefficients of at least 0.5 are regarded as measuring wavelength regions. When glucose is included in components to be measured in a urine sample, referring to FIG. 21, the measuring wavelength is preferably selected from 11380 to 9720 $cm^{-1}$, 9430 to 9400 $cm^{-1}$, 9340 to 9320 $cm^{-1}$, 9260 to 6560 $cm^{-1}$, 6510 to 5540 $cm^{-1}$, 5530 to 5280 $cm^{-1}$, 4980 to 4850 $cm^{-1}$, 4830 to 4480 $cm^{-1}$, 4440 to 4330 $cm^{-1}$ or 4300 to 4010 $cm^{-1}$.

FIG. 22 illustrates a calibration curve showing the relation between concentrations and absorbances of glucose measured at 4398 $cm^{-1}$. It is understood from FIG. 22 that it is possible to carry out quantitative analysis by using a wavelength region having large correlation coefficients. The inclination of the straight line shown in FIG. 22 is obtained by least square fitting, and this inclination of the straight line is the absorbance coefficient $\alpha kj$ in the expression (1).

Figure 23:
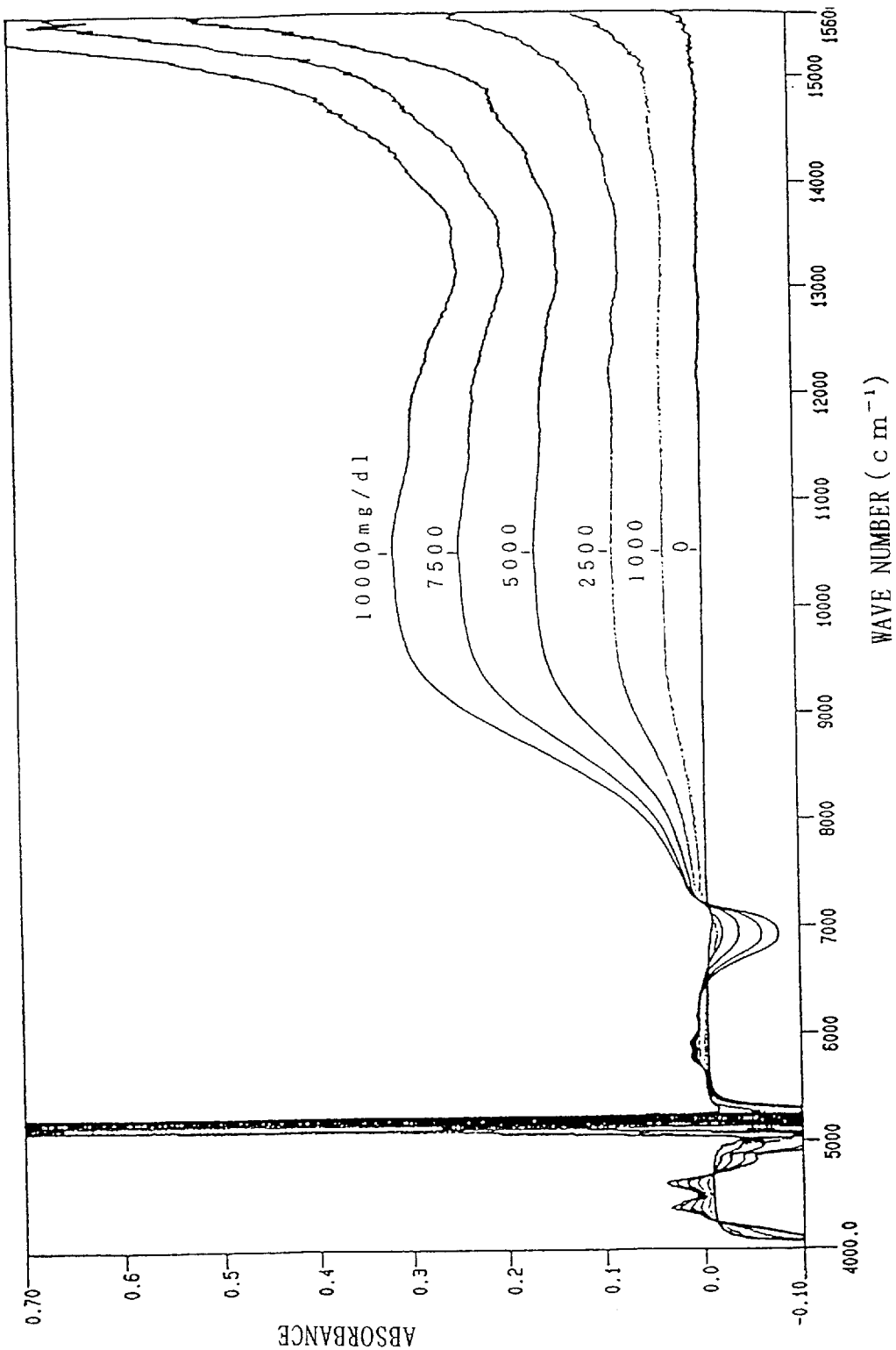
FIG. 23 illustrates spectra of a plurality of samples of aqueous hemoglobin solutions having different concentrations.
Figure 24:
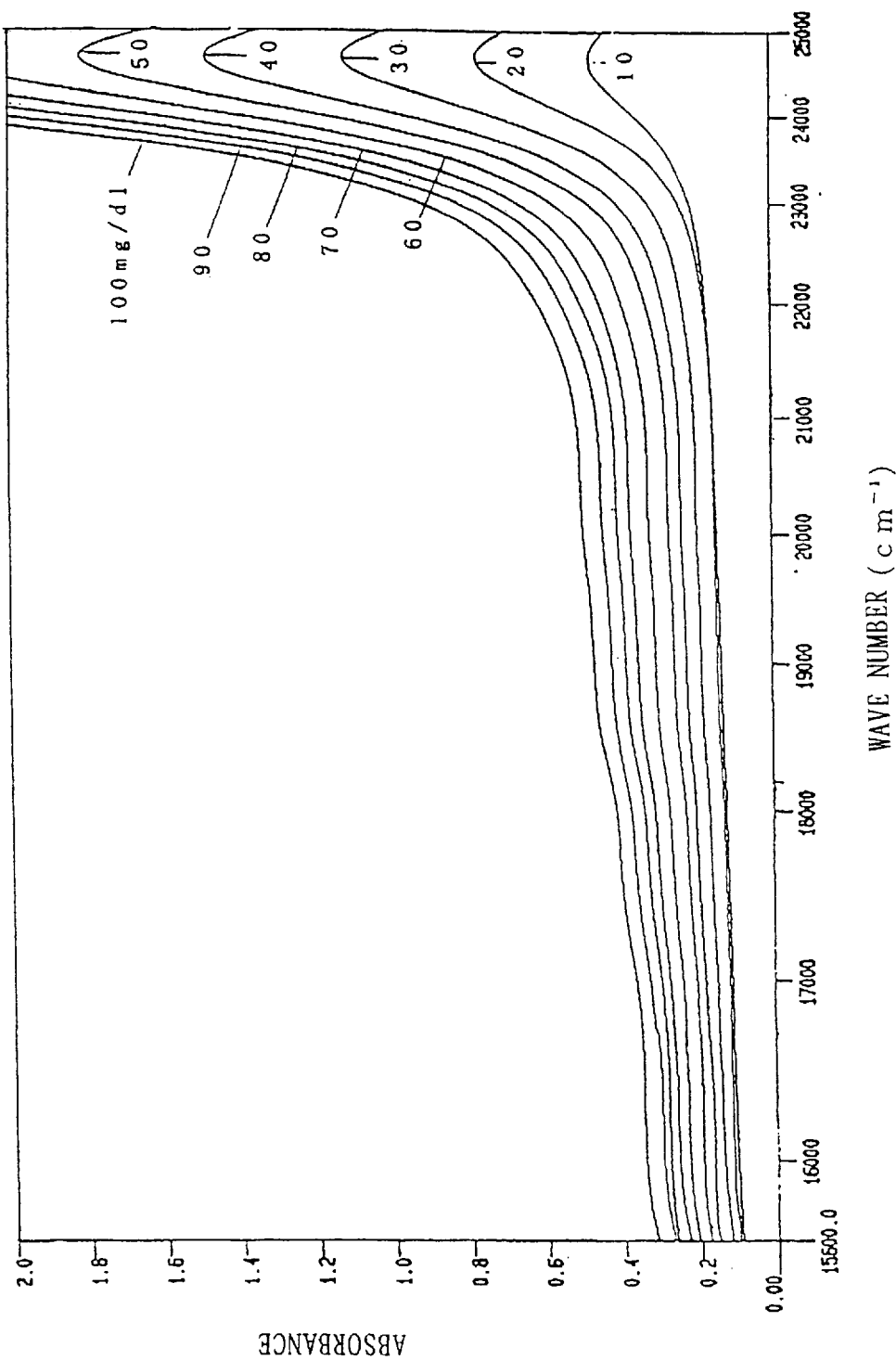
FIG. 24 illustrates spectra of a plurality of other samples of aqueous hemoglobin solutions having different concentrations.
Figure 25:
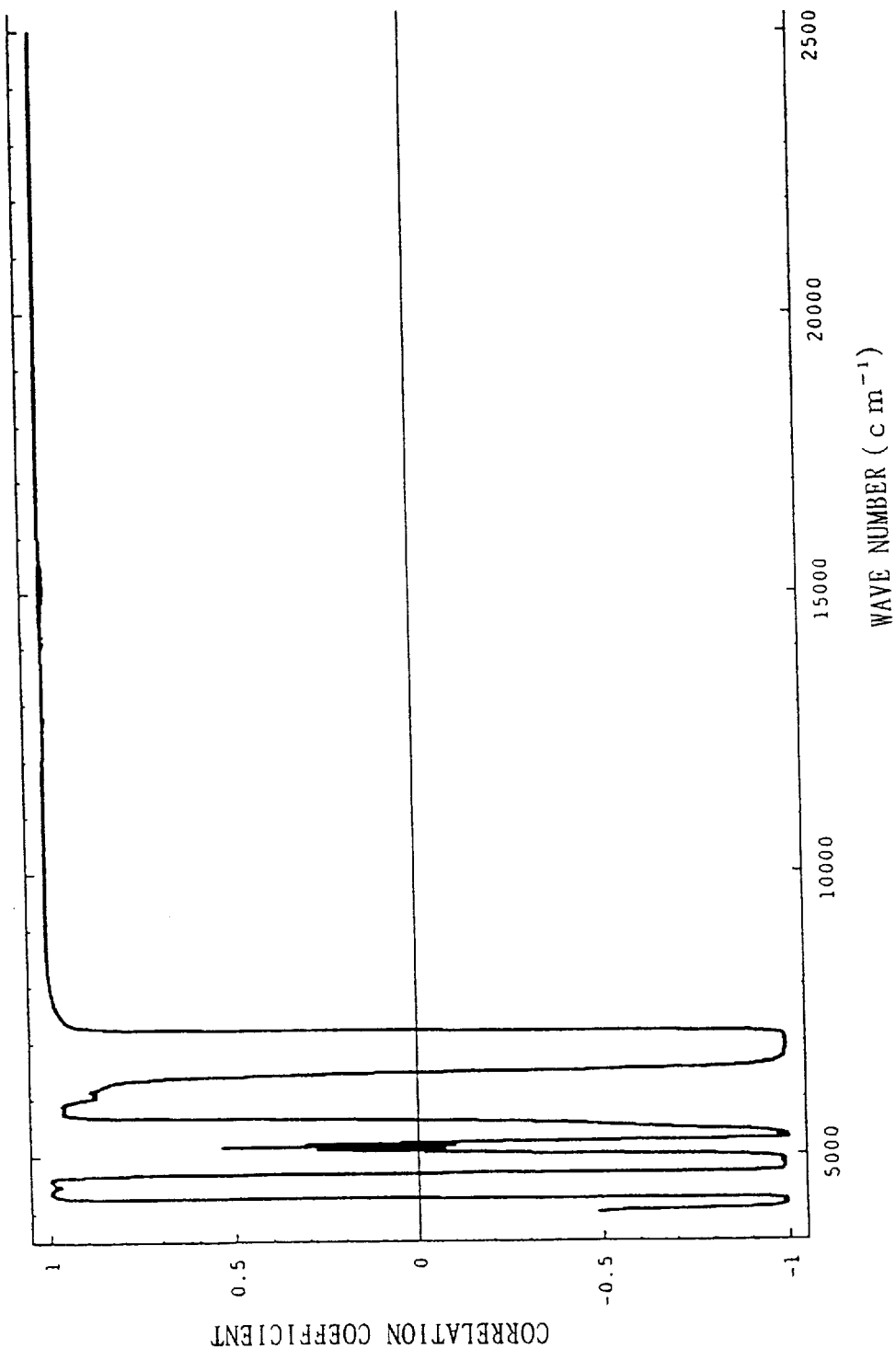
FIG. 25 illustrates wavelength distribution of correlation coefficients (absorbance-concentration) of an aqueous hemoglobin solution.
Figure 26:
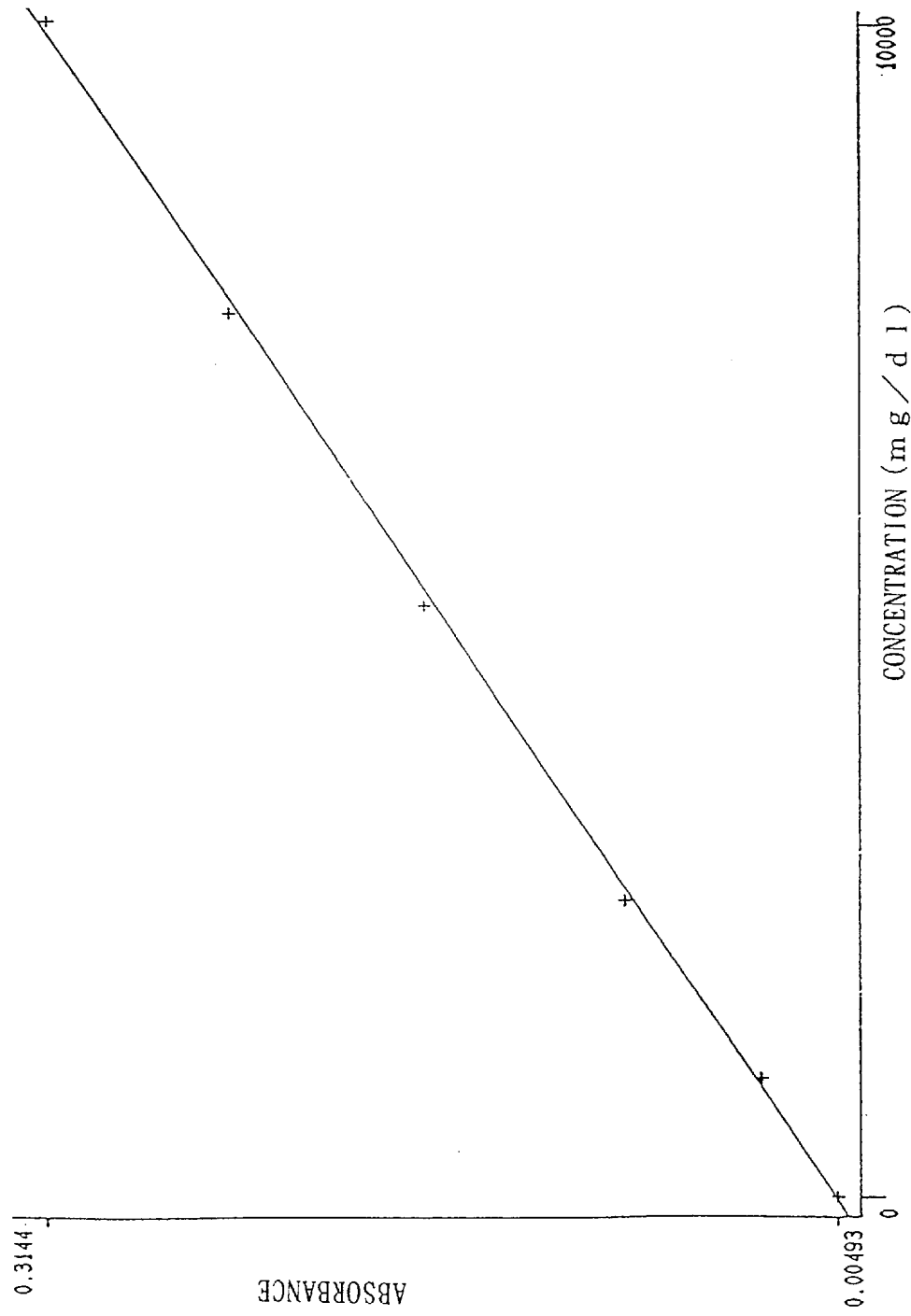
FIG. 26 illustrates a calibration curve showing relation between concentrations and absorbances of an aqueous hemoglobin solution at 10500 cm$^{-1}$.

FIGS. 23 to 26 show results of similar measurement on hemoglobin. FIGS. 23 and 24 illustrate spectra of aqueous hemoglobin solutions at various concentrations, FIG. 25 shows wavelength distribution of correlation coefficients (absorbance-concentration) thereof, and FIG. 26 shows a calibration curve at 10500 $cm^{-1}$.

From FIG. 25, the measuring wavelength for hemoglobin is preferably selected from 25000 to 7250 $cm^{-1}$, 7220 to 6430 $cm^{-1}$, 6190 to 5690 $cm^{-1}$, 5660 to 5280 $cm^{-1}$ or 4900 to 4080 $cm^{-1}$.

Figure 27:
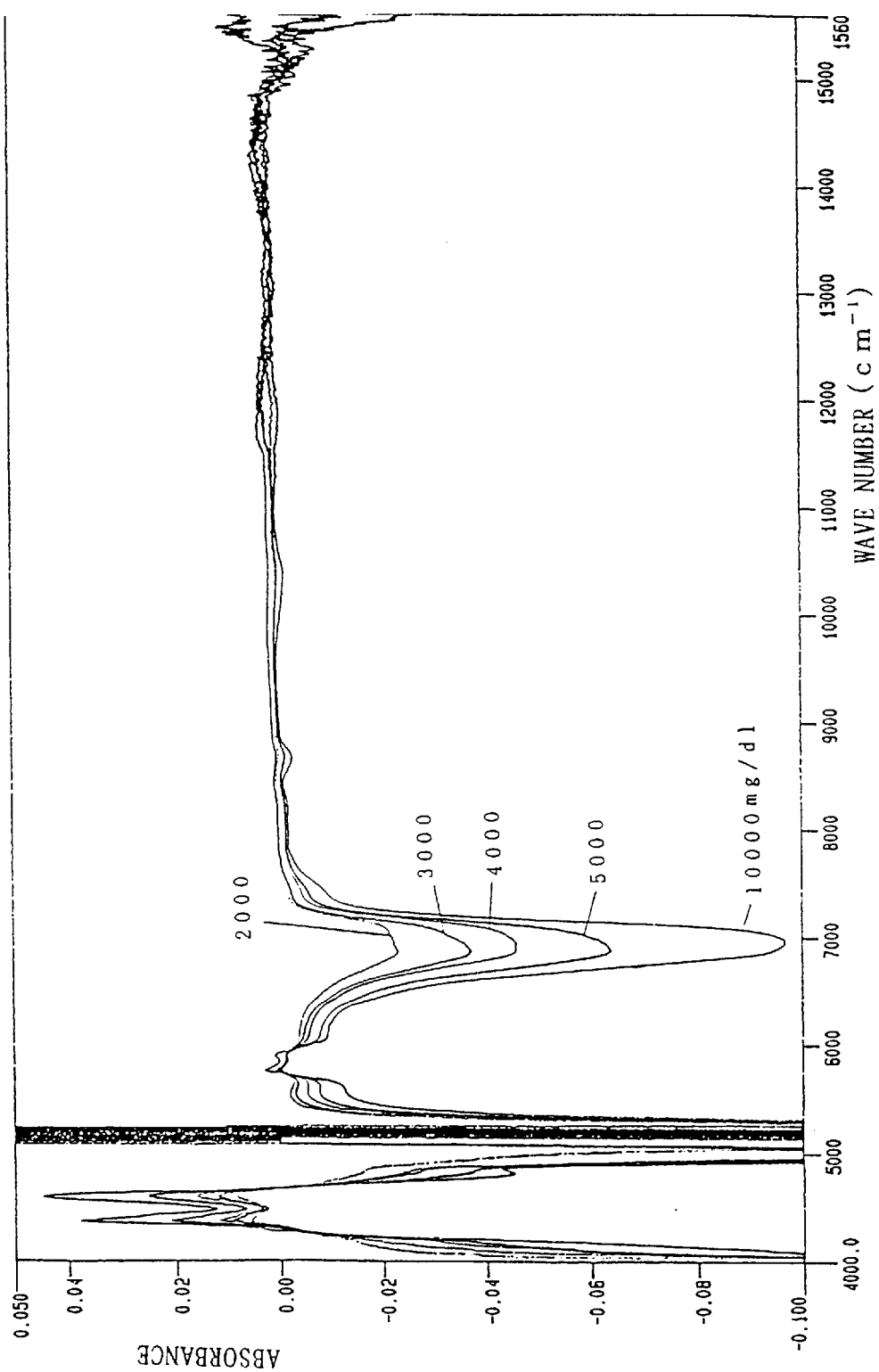
FIG. 27 illustrates spectra of a plurality of samples of aqueous albumin solutions having different concentrations.
Figure 28:
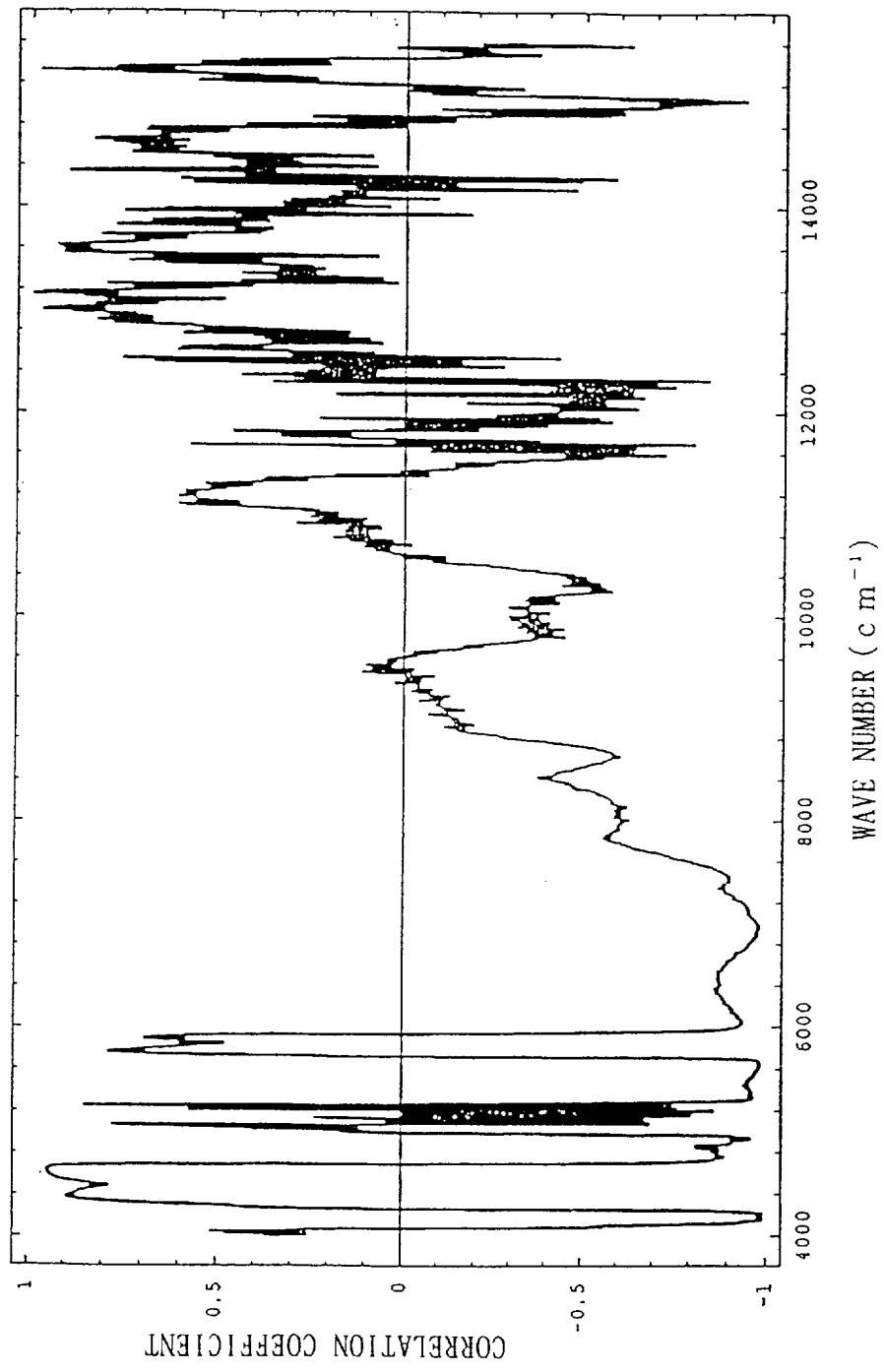
FIG. 28 illustrates wavelength distribution of correlation coefficients (absorbance-concentration) of an aqueous albumin solution.
Figure 29:
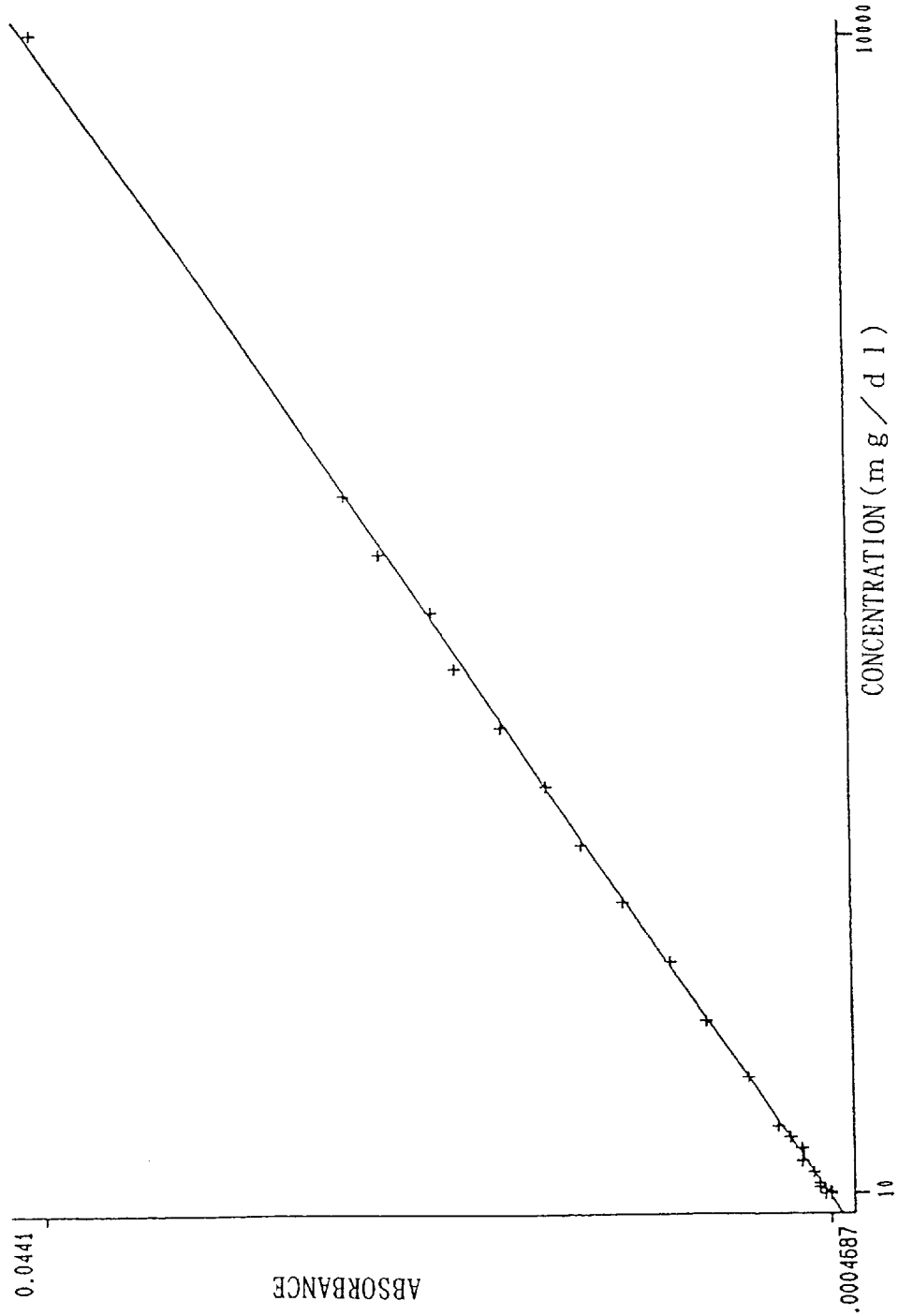
FIG. 29 illustrates a calibration curve showing relation between concentrations and absorbances of an aqueous albumin solution at 4371 cm$^{-1}$.

FIGS. 27 to 29 show results of similar measurement on albumin. FIG. 27 illustrates spectra of aqueous albumin solutions at various concentrations, FIG. 28 shows wavelength distribution of correlation coefficients (absorbance-concentration) thereof, and FIG. 29 shows a calibration curve at 4371 $cm^{-1}$.

From FIG. 28, the measuring beam for albumin is preferably selected from 7280 to 6350 $cm^{-1}$, 5910 to 5880 $cm^{-1}$, 5790 to 5740 $cm^{-1}$, 5630 to 5300 $cm^{-1}$, 4900 to 4720 $cm^{-1}$, 4670 to 4280 $cm^{-1}$ or 4230 to 4070 $cm^{-1}$.

Figure 30:
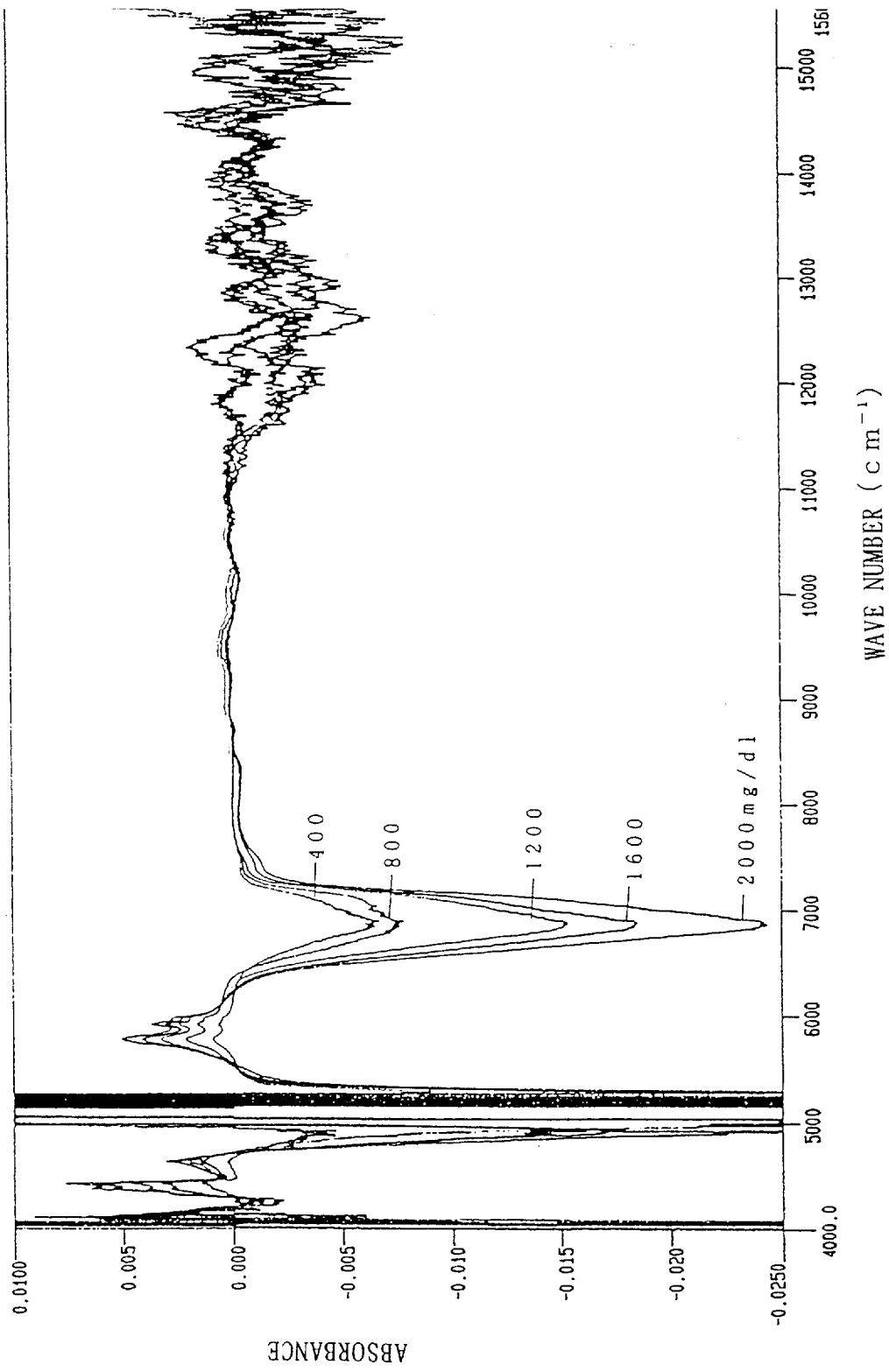
FIG. 30 illustrates spectra of a plurality of samples of aqueous lithium acetoacetate solutions having different concentrations.
Figure 31:
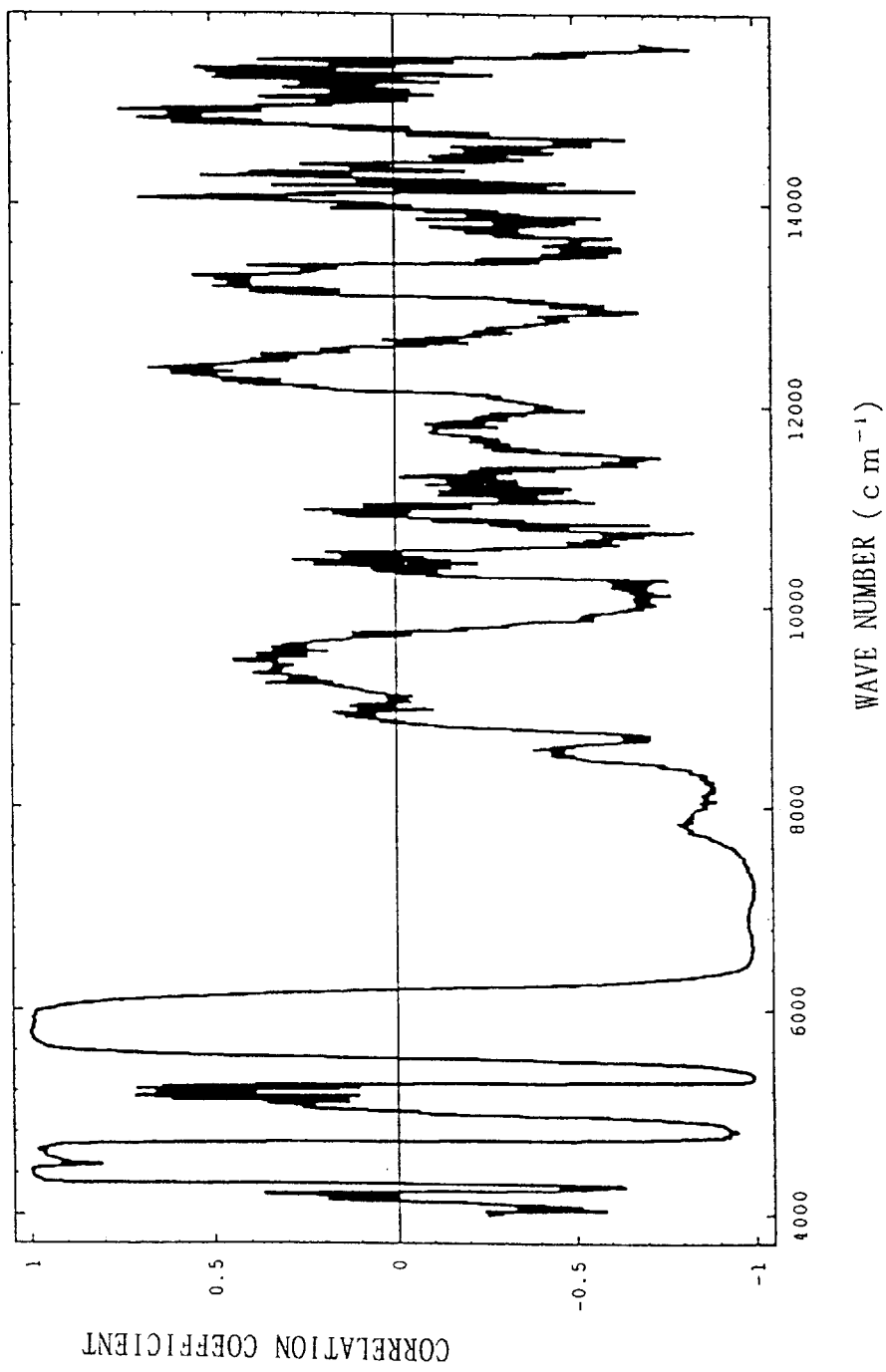
FIG. 31 illustrates wavelength distribution of correlation coefficients (absorbance-concentration) of an aqueous lithium acetoacetate solution.
Figure 32:
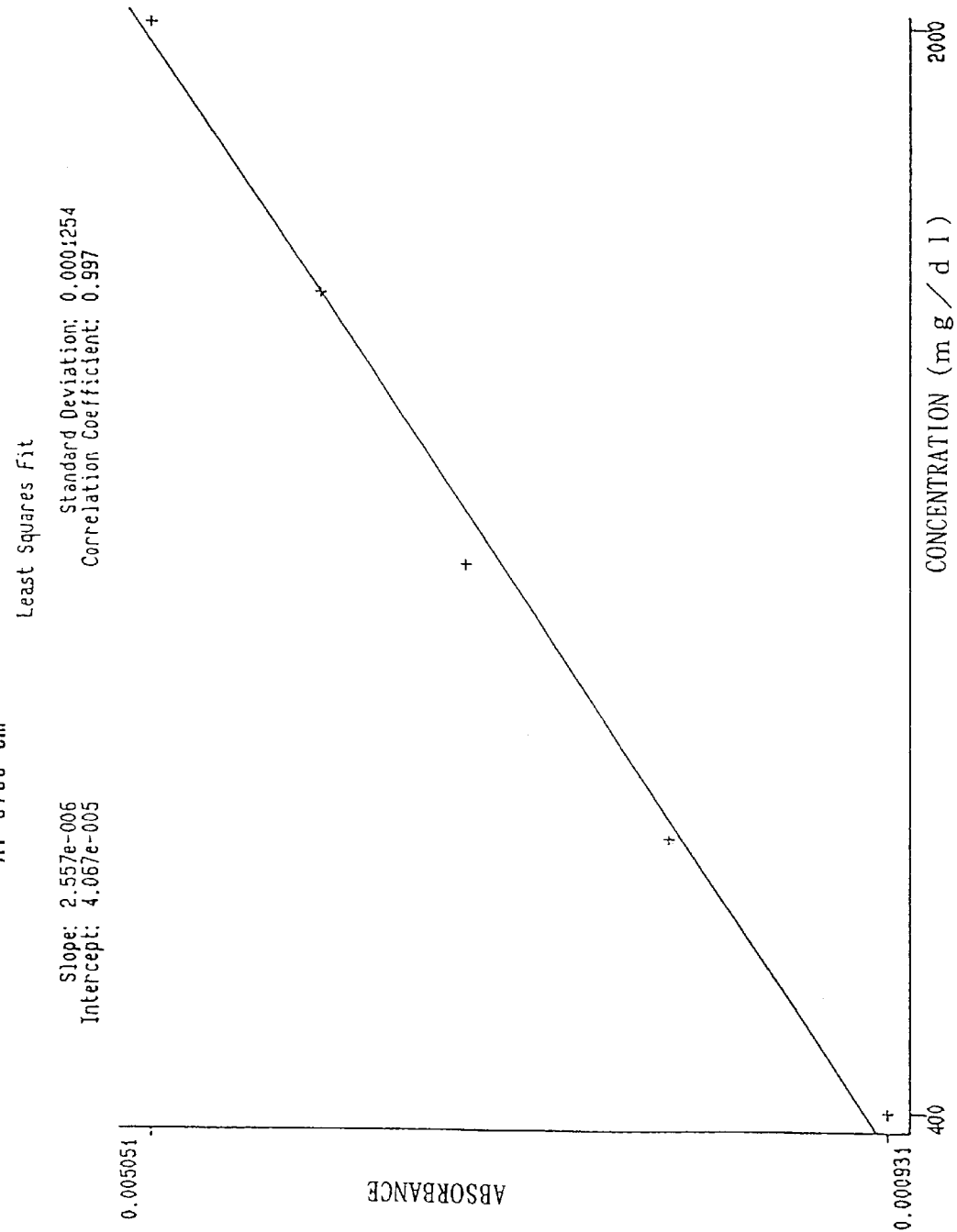
FIG. 32 illustrates a calibration curve showing relation between concentrations and absorbances of an aqueous lithium acetoacetate solution at 5780 cm$^{-1}$.

FIGS. 30 to 32 show results of similar measurement on lithium acetoacetate. FIG. 30 illustrates spectra of aqueous lithium acetoacetate solutions at various concentrations, FIG. 31 shows wavelength distribution of correlation coefficients (absorbance-concentration) thereof, and FIG. 32 shows a calibration curve at 5780 $cm^{-1}$.

From FIG. 31, the measuring wavelength for lithium acetoacetate is preferably selected from 8490 to 6360 $cm^{-1}$, 6040 to 5610 $cm^{-1}$, 5430 to 5300 $cm^{-1}$, 4900 to 4760 $cm^{-1}$, 4680 to 4510 $cm^{-1}$ or 4470 to 4320 $cm^{-1}$.

Figure 33:
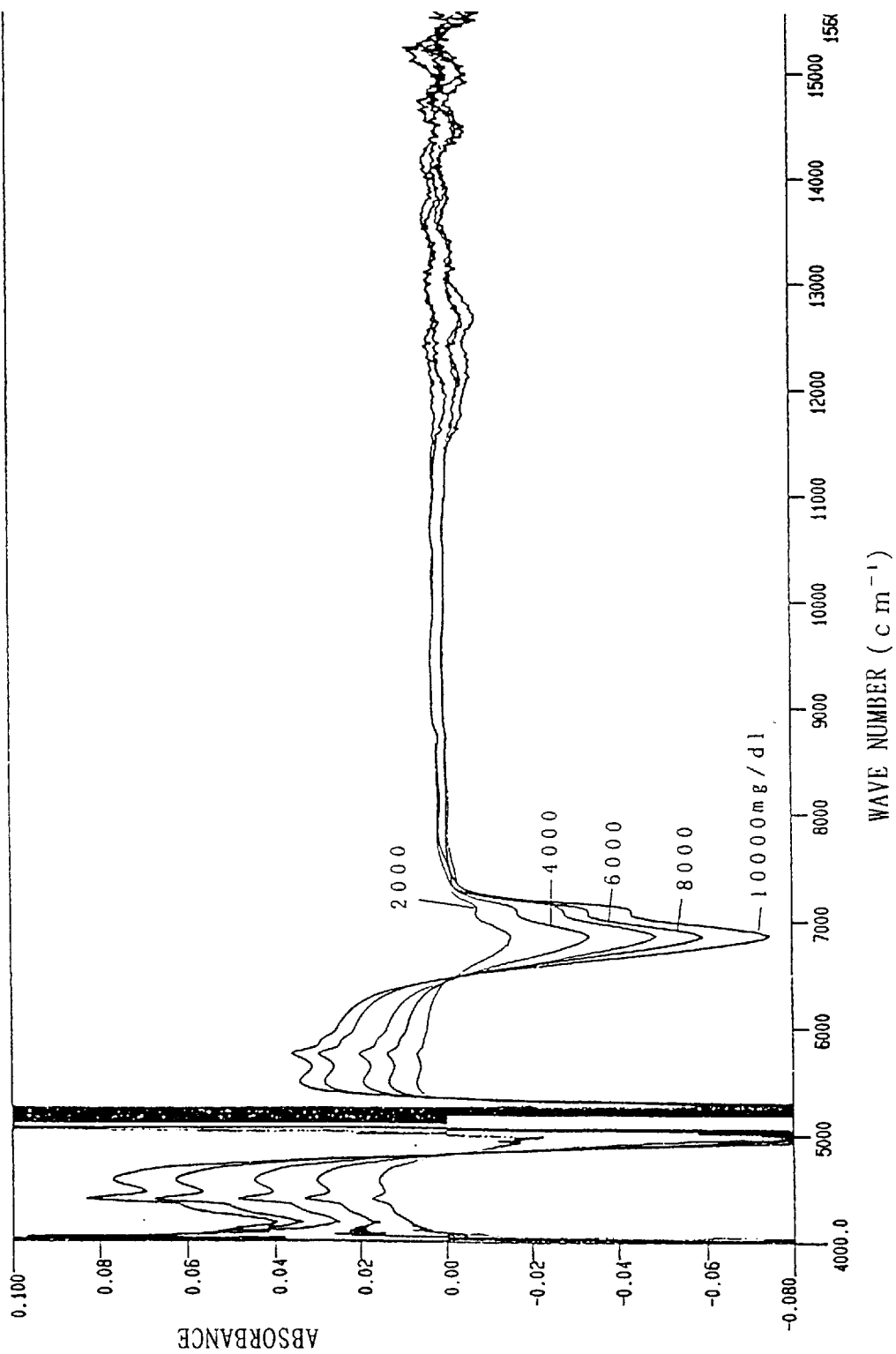
FIG. 33 illustrates spectra of a plurality of samples of aqueous ascorbic acid solutions having different concentrations.
Figure 34:
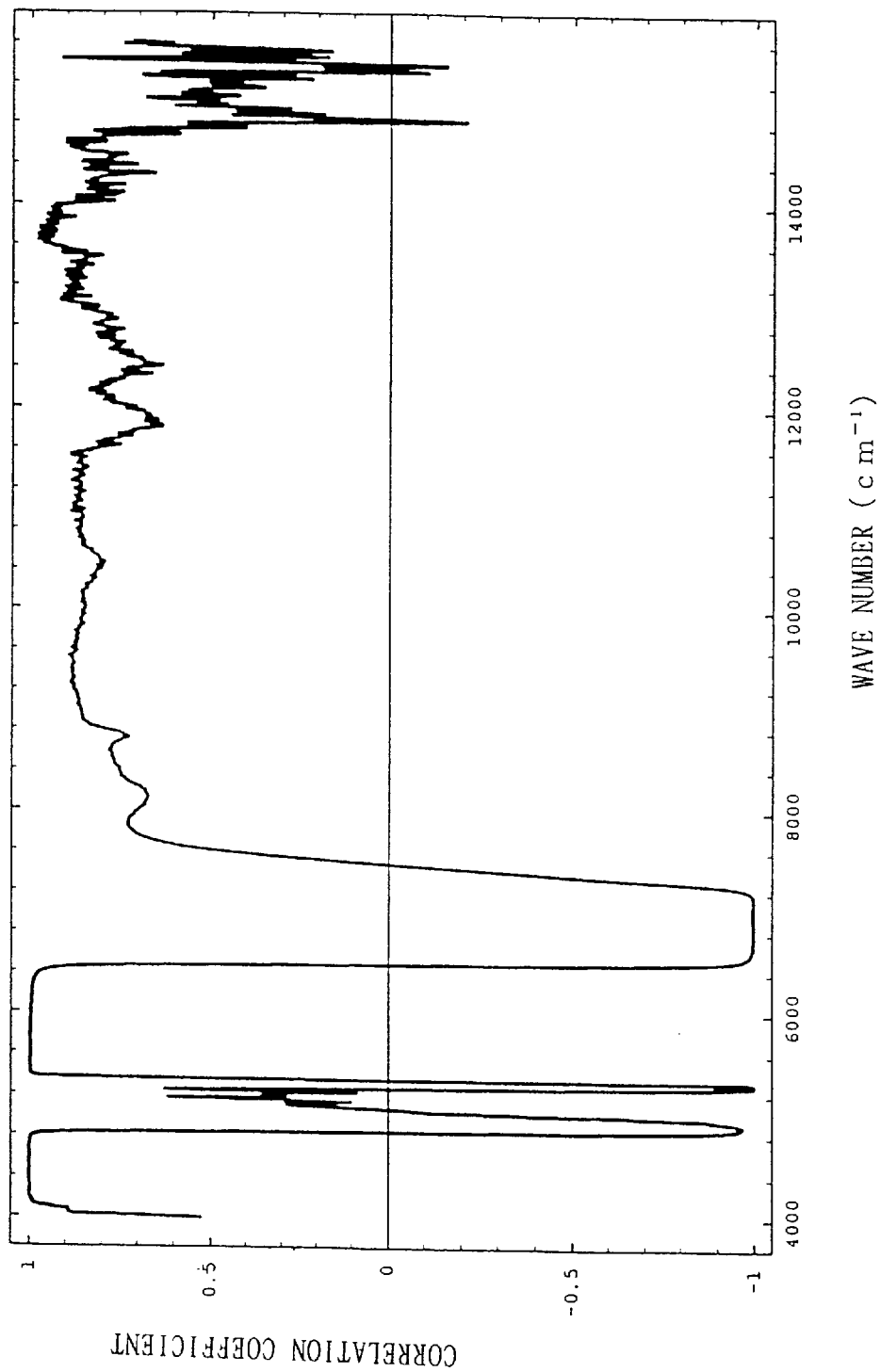
FIG. 34 illustrates wavelength distribution of correlation coefficients (absorbance-concentration) of an aqueous ascorbic acid solution.
Figure 35:
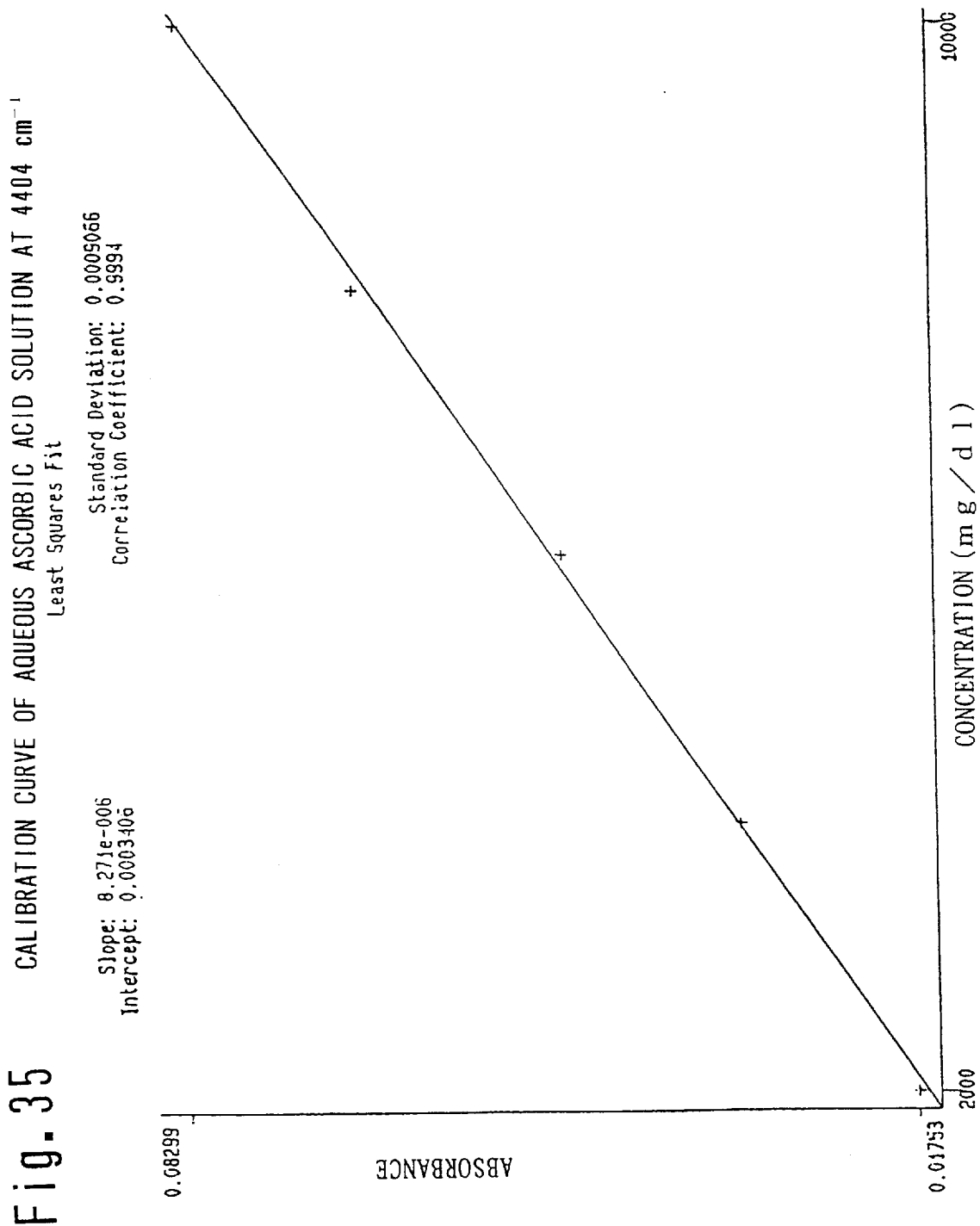
FIG. 35 illustrates a calibration curve showing relation between concentrations and absorbances of an aqueous ascorbic acid solution at 4404 cm$^{-1}$.

FIGS. 33 to 35 show results of similar measurement on ascorbic acid. FIG. 33 illustrates spectra of aqueous ascorbic acid solutions at various concentrations, FIG. 34 shows wavelength distribution of correlation coefficients (absorbance-concentration) thereof, and FIG. 35 shows a calibration curve at 4404 $cm^{-1}$.

From FIG. 34, the wavelength for ascorbic acid is preferably selected from 7270 to 6520 $cm^{-1}$, 6430 to 5290 $cm^{-1}$, 4950 to 4860 $cm^{-1}$ or 4810 to 4090 $cm^{-1}$.

Figure 36:
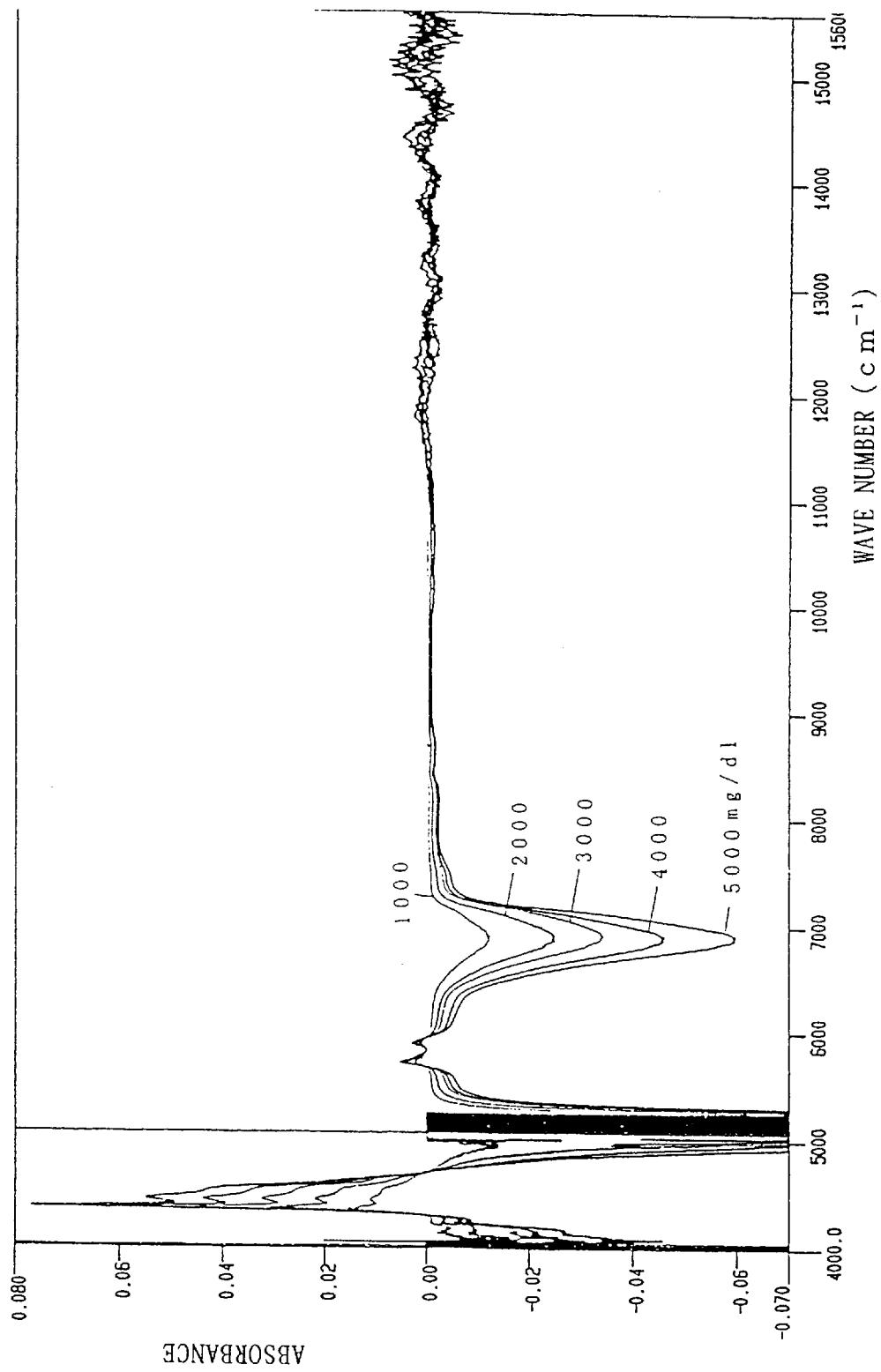
FIG. 36 illustrates spectra of a plurality of samples of aqueous creatinine solutions having different concentrations.
Figure 37:
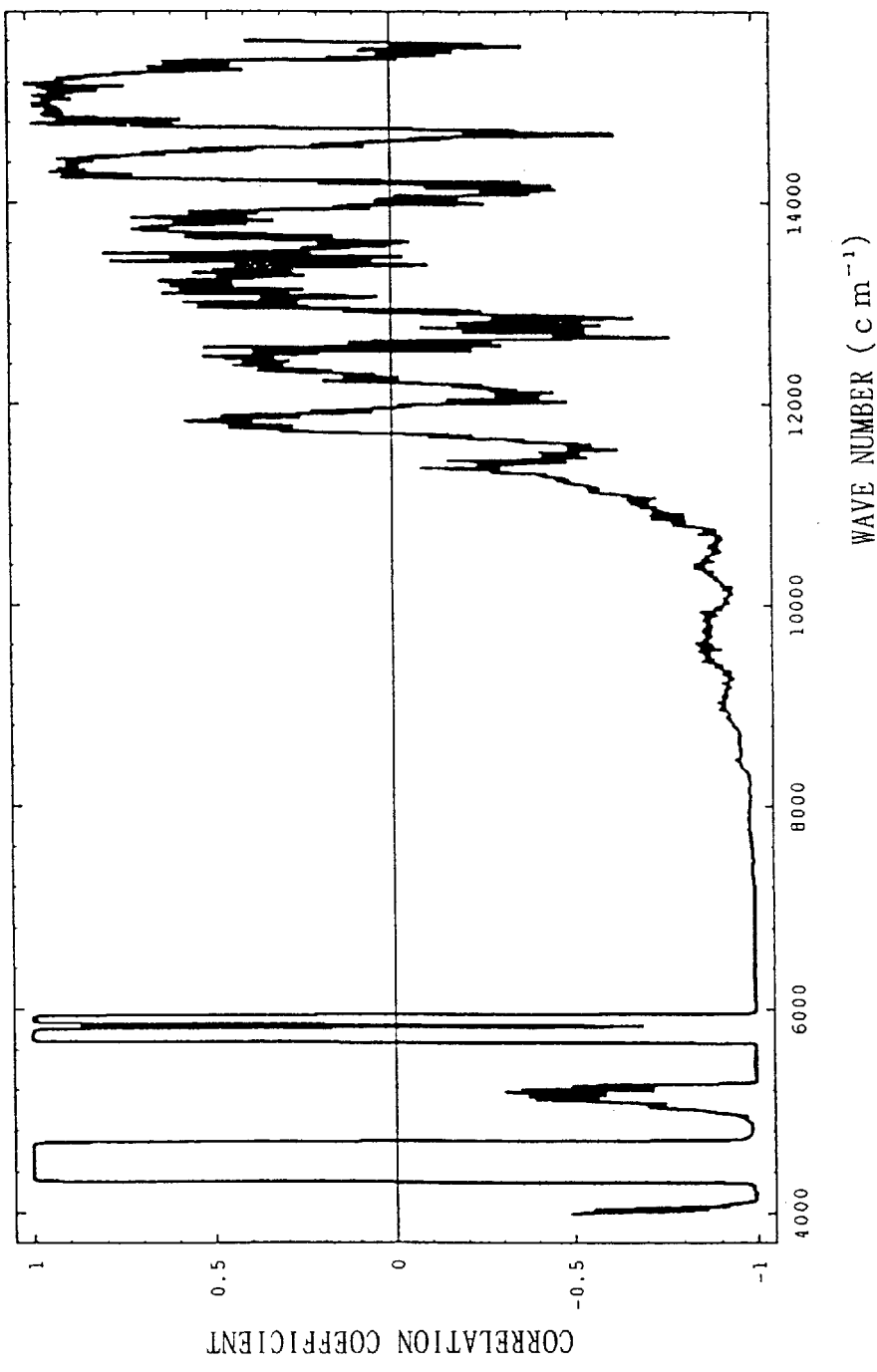
FIG. 37 illustrates wavelength distribution of correlation coefficients (absorbance-concentration) of an aqueous creatinine solution.
Figure 38:
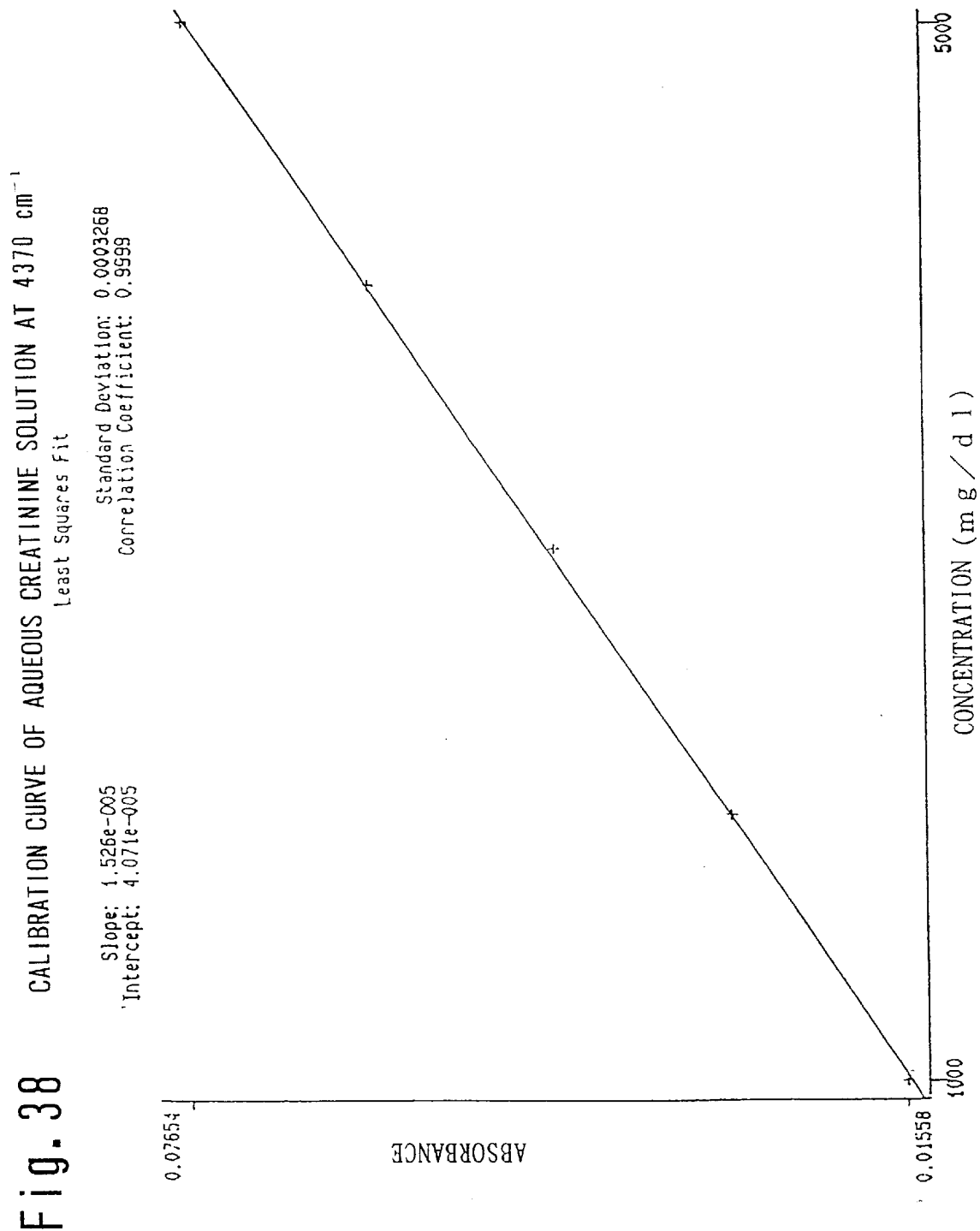
FIG. 38 illustrates a calibration curve showing relation between concentrations and absorbances of an aqueous creatinine solution at 4370 cm$^{-1}$.

FIGS. 36 to 38 show results of similar measurement on creatinine. FIG. 36 illustrates spectra of aqueous creatinine solutions at various concentrations, FIG. 37 shows wavelength distribution of correlation coefficients (absorbance-concentration) thereof, and FIG. 38 shows a calibration curve at 4370 $cm^{-1}$.

From FIG. 37, the measuring wavelength for creatinine is preferably selected from 9370 to 5870 $cm^{-1}$, 5810 to 5280 $cm^{-1}$, 4980 to 4730 $cm^{-1}$, 4690 to 4320 $cm^{-1}$ or 4290 to 4090 $cm^{-1}$.

Figure 39:
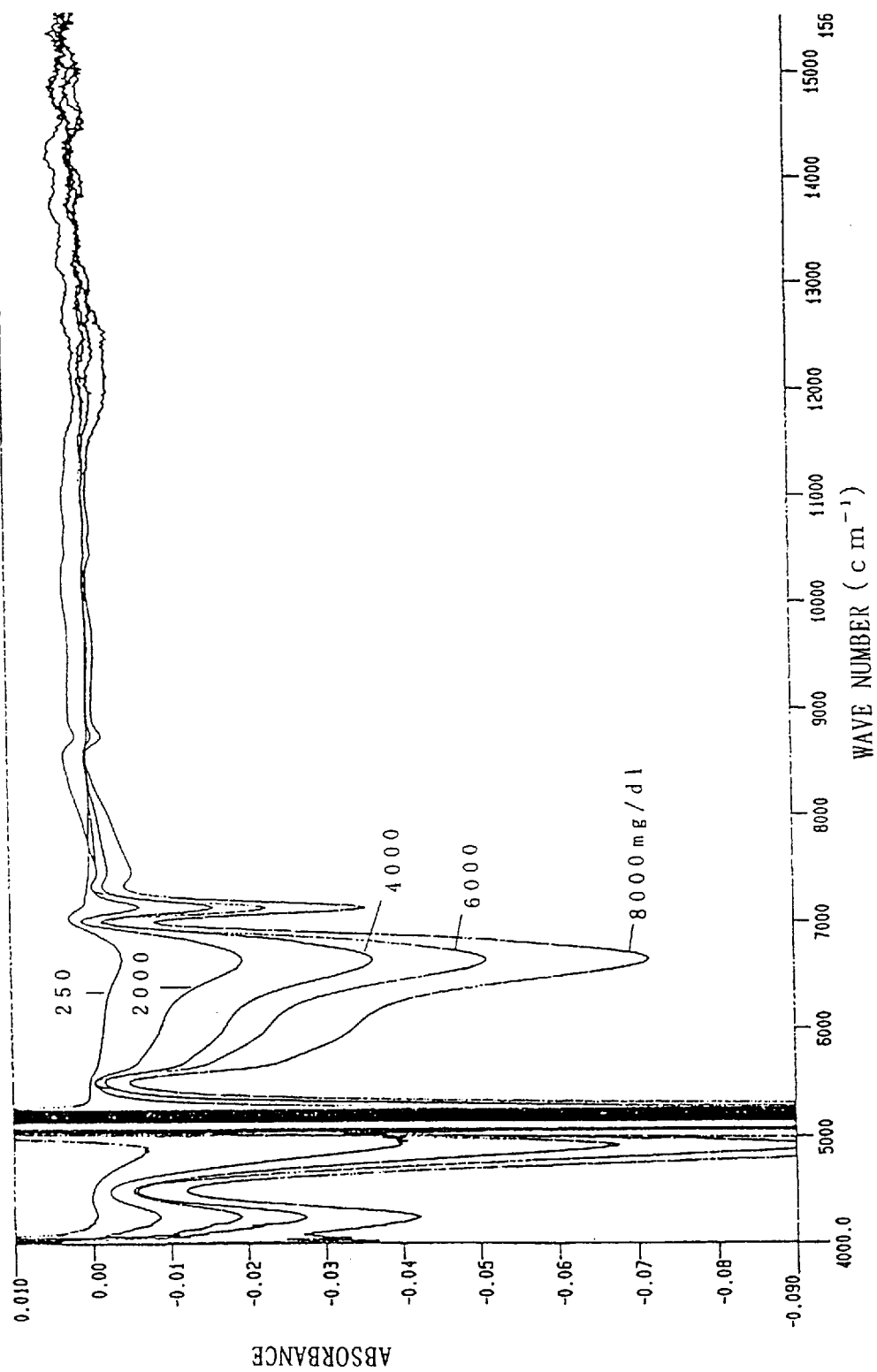
FIG. 39 illustrates spectra of a plurality of samples of aqueous sodium chloride solutions having different concentrations.
Figure 40:
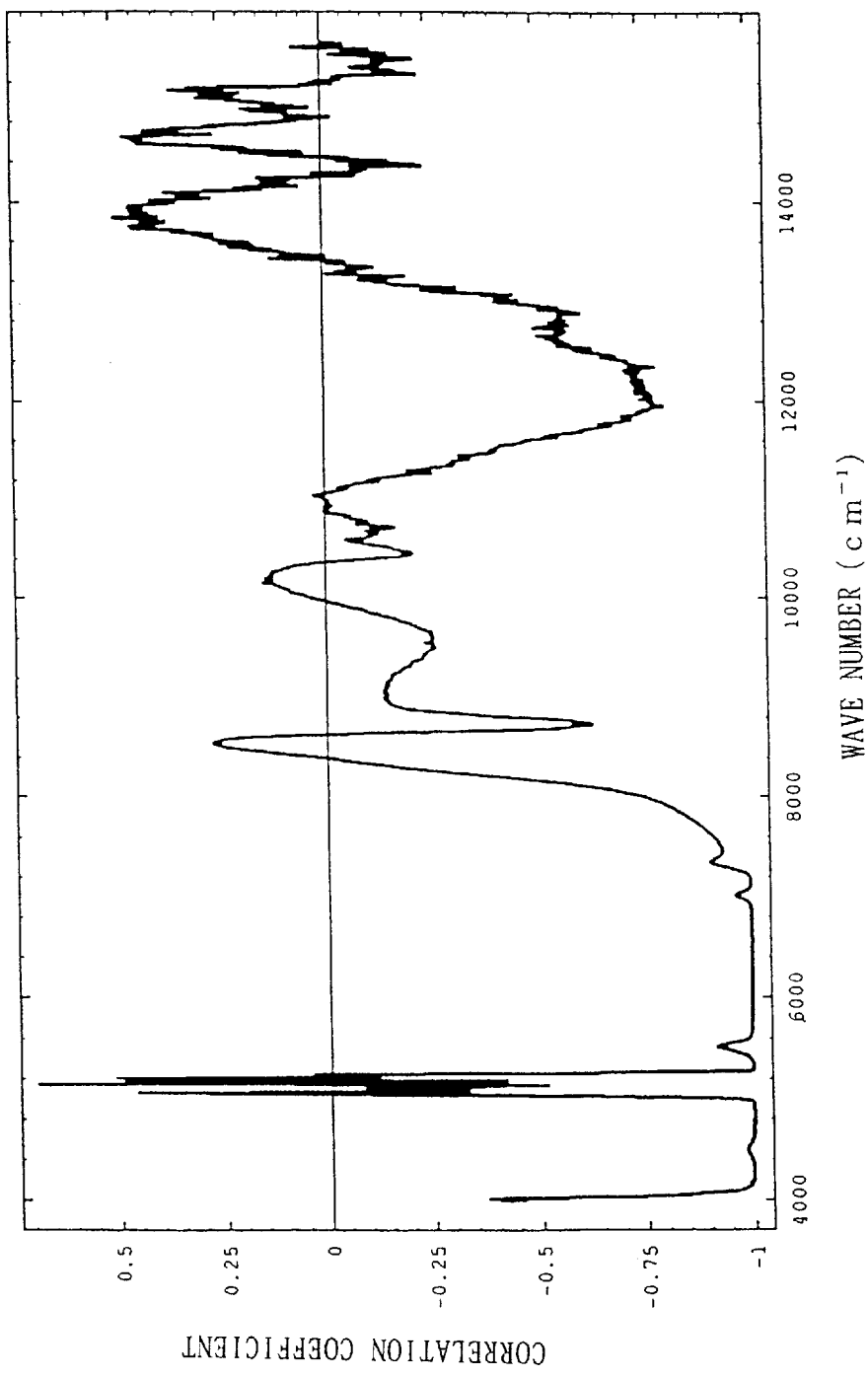
FIG. 40 illustrates wavelength distribution of correlation coefficients (absorbance-concentration) of an aqueous sodium chloride solution.
Figure 41:
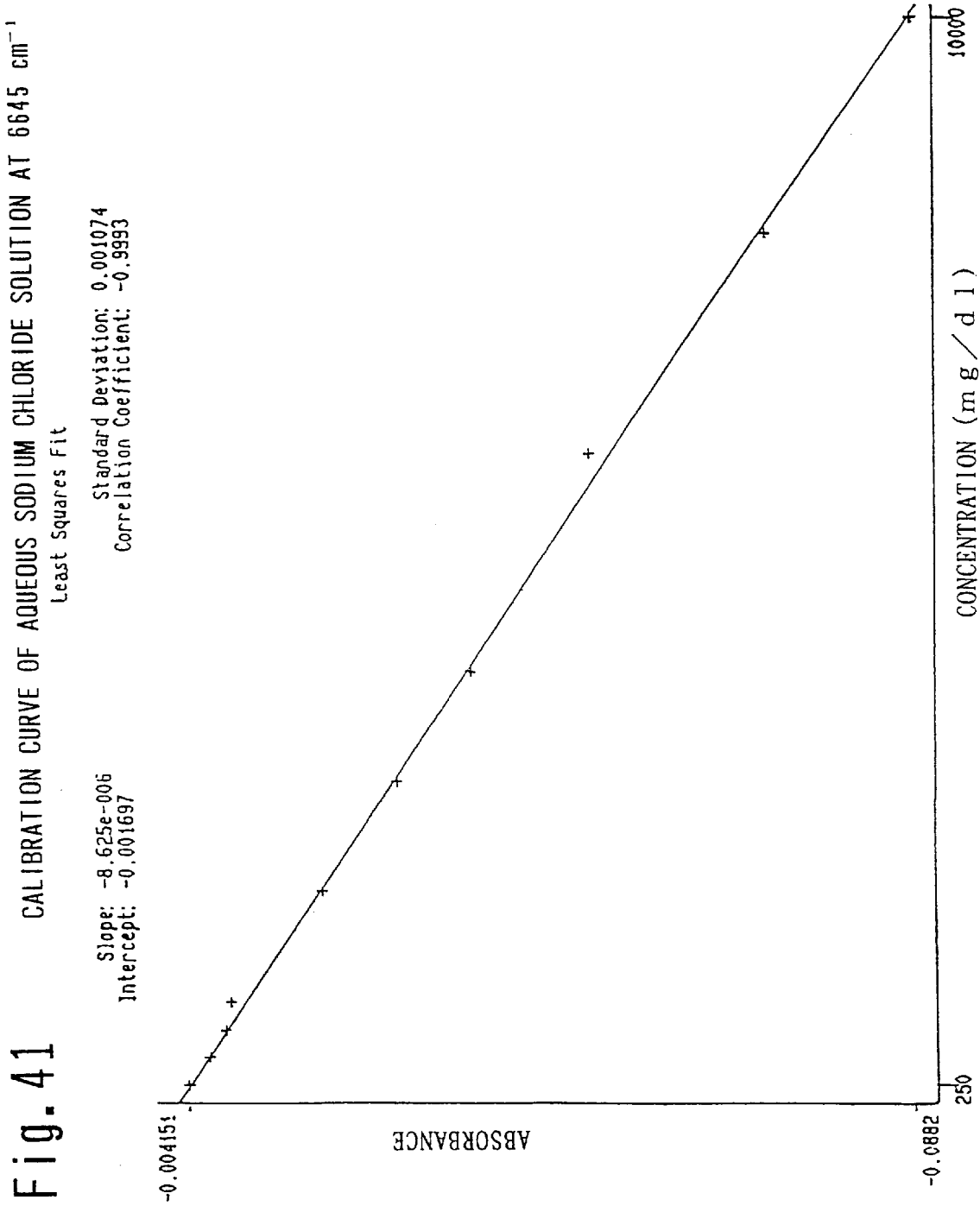
FIG. 41 illustrates a calibration curve showing relation between concentrations and absorbances of an aqueous sodium chloride solution at 6645 cm$^{-1}$.

FIGS. 39 to 41 show results of similar measurement on sodium chloride. FIG. 39 illustrates spectra of aqueous sodium chloride solutions at various concentrations, FIG. 40 shows wavelength distribution of correlation coefficients (absorbance-concentration) thereof, and FIG. 41 shows a calibration curve at 6645 $cm^{-1}$.

From FIG. 40, the measuring wavelength for sodium chloride is preferably from 7640 to 5280 $cm^{-1}$ or 4980 to 4080 $cm^{-1}$.

Figure 42:
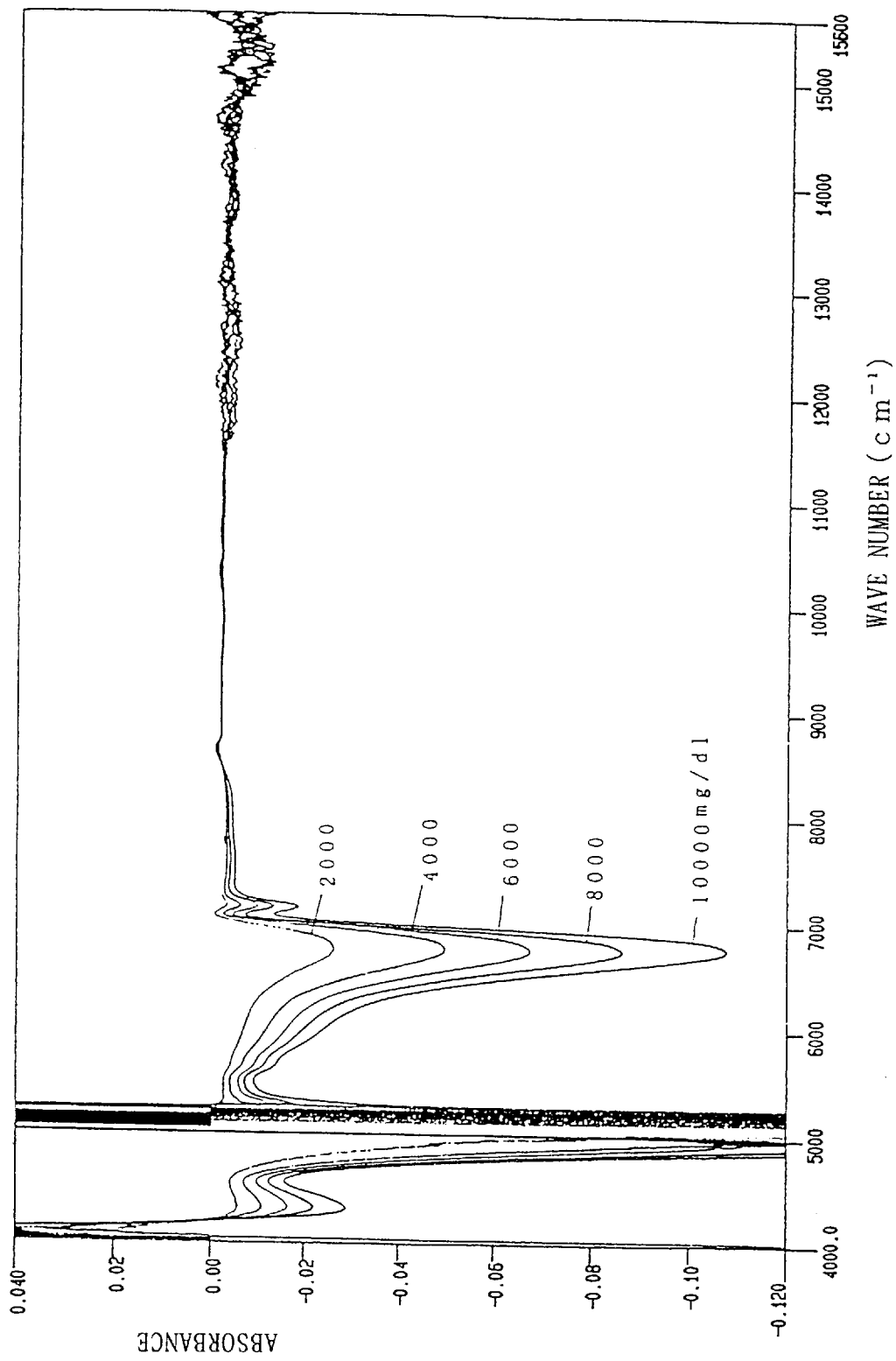
FIG. 42 illustrates spectra of a plurality of samples of aqueous sodium nitrite solutions having different concentrations.
Figure 43:
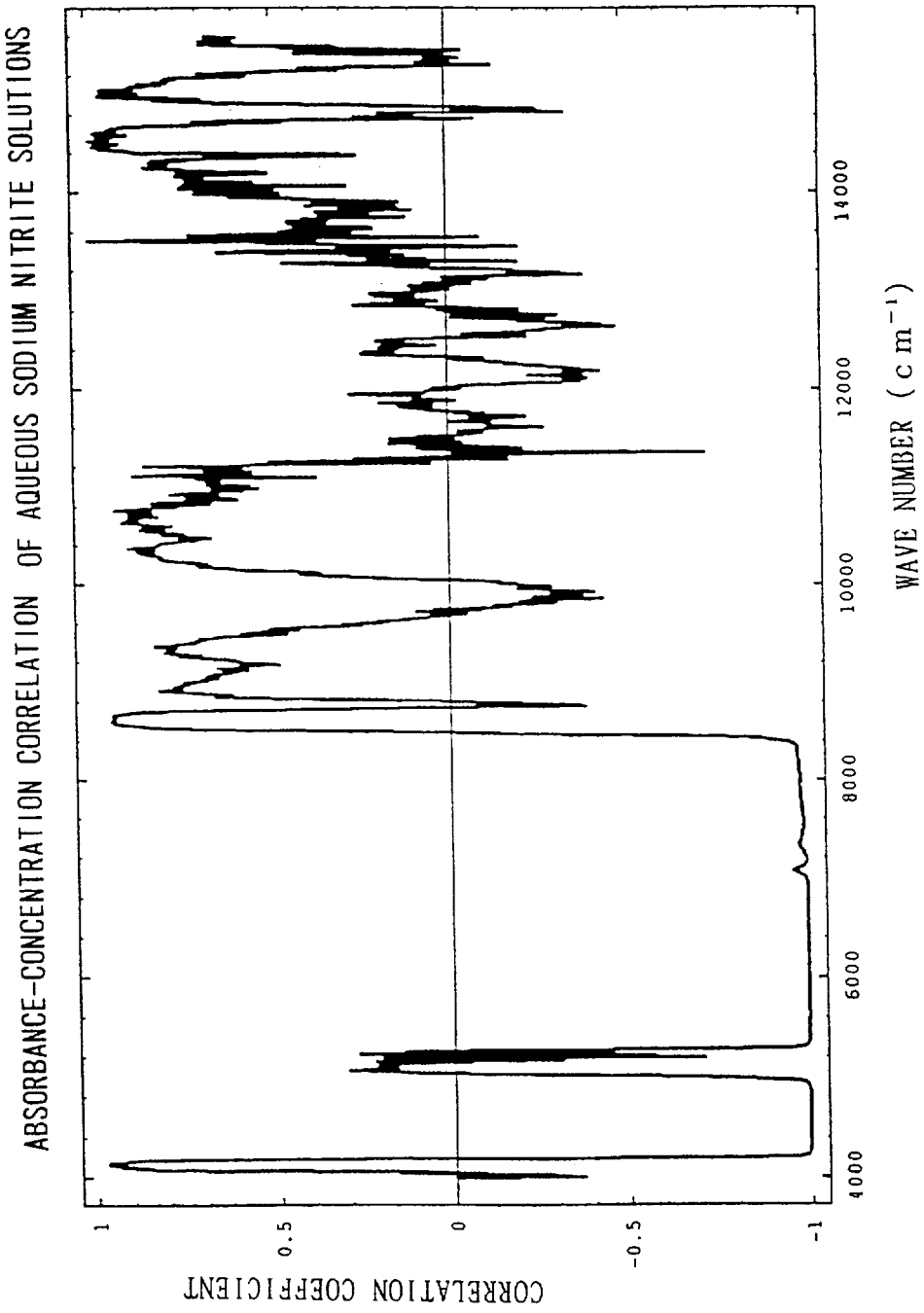
FIG. 43 illustrates wavelength distribution of correlation coefficients (absorbance-concentration) of an aqueous sodium nitrite solution.

FIGS. 42 to 44 show results of similar measurement on sodium nitrite. FIG. 42 illustrates spectra of aqueous sodium nitrite solutions at various concentrations, FIG. 43 shows wavelength distribution of correlation coefficients (absorbance-concentration) thereof, and FIG. 44 shows a calibration curve at 6766 $cm^{-1}$.

From FIG. 43, the measuring wavelength for sodium nitrite is preferably selected from 8680 to 5300 $cm^{-1}$, 4980 to 4210 $cm^{-1}$ or 4160 to 4100 $cm^{-1}$.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method of measuring uric components for quantitatively analyzing a plurality of uric components at the same time, comprising the steps of:

irradiating a urine sample with light of wavenumber not higher than about 25,000 cm$^{-1}$ and not lower than about 4,000 cm$^{-1}$;

measuring absorbances of said uric components to be measured at measuring wavelengths selected from wavelengths having correlation coefficients which have absolute values of at least 0.5 and not greater than 1.0, said correlation coefficients being defined as coefficients between concentrations and absorbances of aqueous solutions containing respective single components in the visible or near infrared wavelength region according to the formula:

$$Rj = \frac{(m-1) \sum_{i=1}^{m} (Aij - \overline{Aj})(Ci - \overline{C})}{\sum_{i=1}^{m} (Aij - \overline{Aj}) \cdot \sum_{i=1}^{m} (Ci - \overline{C})}$$

where:

$$\overline{Aj} = \frac{1}{m} \sum_{i=1}^{m} Aij$$

$$\overline{C} = \frac{1}{m} \sum_{i=1}^{m} Ci$$

where:
m: the number of samples
Aij: absorbance of the component in i th sample at wavelength $\lambda j$
Ci: concentration of the component in i th sample, said measuring wavelengths being specific to respective said uric components; and
determining concentrations of each of said plurality of uric components at the same time from said absorbances being measured at said measuring wavelengths by multivariate regression analysis.

2. The method in accordance with claim 1, wherein said measuring wavelengths for respective said components are selected from wavelengths having absolute values of at least 0.9 of said correlation coefficients between said concentrations and said absorbances as to respective said components.

3. The method in accordance with claim 1, wherein said measuring wavelengths are selected from a wavenumber region of 25000 to 5280 cm$^{-1}$ or 4980 to 4000 cm$^{-1}$ having high transmittance with respect to water while avoiding a wavelength region having strong absorption with respect to water.

4. The method in accordance with claim 3, wherein said uric components to be measured include a plurality of components selected from among glucose, hemoglobin, albumin, lithium acetoacetate, ascorbic acid, creatinine, sodium chloride and sodium nitrite, said measuring wavelengths for said components, expressed in wavenumbers, being selected:

from 11380 to 9720 cm$^{-1}$, 9430 to 9400 cm$^{-1}$, 9340 to 9320 cm$^{-1}$, 9260 to 6560 cm$^{-1}$, 6510 to 5540 cm$^{-1}$, 5530 to 5280 cm$^{-1}$, 4980 to 4850 cm$^{-1}$, 4830 to 4480 cm$^{-1}$, 4440 to 4330 cm$^{-1}$ or 4300 to 4010 cm$^{-1}$ for glucose, from 25000 to 7250 cm$^{-1}$, 7220 to 6430 cm$^{-1}$, 6190 to 5690 cm$^{-1}$, 5660 to 5280 cm$^{-1}$ or 4900 to 4080 cm$^{-1}$ for hemoglobin, from 7280 to 6350 cm$^{-1}$, 5910 to 5880 cm$^{-1}$, 5790 to 5740 cm$^{-1}$, 5630 to 5300 cm$^{-1}$, 4900 to 4720 cm$^{-1}$, 4670 to 4280 cm$^{-1}$ or 4230 to 4070 cm$^{-1}$ for albumin, from 8490 to 6360 cm$^{-1}$, 6040 to 5610 cm$^{-1}$, 5430 to 5300 cm$^{-1}$, 4900 to 4760 cm$^{-1}$, 4680 to 4510 cm$^{-1}$ or 4470 to 4320 cm$^{-1}$ for lithium acetoacetate;

from 7270 to 6520 cm$^{-1}$, 6430 to 5290 cm$^{-1}$, 4950 to 4860 cm$^{-1}$ or 4810 to 4090 cm$^{-1}$ for ascorbic acid, from 9370 to 5870 cm$^{-1}$, 5810 to 5280 cm$^{-1}$, 4980 to 4730 cm$^{-1}$, 4690 to 4320 cm$^{-1}$ or 4290 to 4090 cm$^{-1}$ for creatinine, from 7640 to 5280 cm$^{-1}$ or 4980 to 4080 cm$^{-1}$ for sodium chloride, and from 8680 to 5300 cm$^{-1}$, 4980 to 4210 cm$^{-1}$, or 4160 to 4100 cm$^{-1}$ for sodium nitrite.

5. A uric component measuring apparatus, comprising:
a urine collecting part for collecting urine;
a measuring part comprising a light source part for introducing a measuring beam of wavenumber not higher than about 25,000 cm$^{-1}$ and not lower than about 4,000 cm$^{-1}$ into said urine being collected in said urine collecting part and a light receiving part for receiving and detecting said measuring beam being transmitted through said urine, for measuring absorbances of uric components to be measured at measuring wavelengths being selected therefor respectively; and
an arithmetic processing part for calculating a plurality of uric component concentrations on the basis of said absorbances being measured by said measuring part at said plurality of measuring wavelengths.

6. The uric component measuring apparatus in accordance with claim 5, further comprising a probe being provided on its forward end with a light transmission end and a light receiving end being opposed to each other at a prescribed space and comprising a light transmission side guide path for guiding a measuring beam to said light transmission end and a light receiving side guide path for guiding incident said measuring beam to said light receiving end, said forward end being dipped in urine being stored in said urine collecting part, base end portions of said guide paths being positioned outside said urine collecting part, wherein
said light source part is so arranged in said measuring part as to introduce said measuring beam into said base end portion of said light transmission side guide path of said probe, said light receiving part being so arranged as to receive said measuring beam being guided by said light receiving side guide path of said probe.

7. The uric component measuring apparatus in accordance with claim 5, wherein
said urine collecting part comprises a cell internally communicating with said urine collecting part and projecting from said urine collecting part to have a prescribed optical length,
said measuring part having a cell setting portion for setting said cell, said light source part being so arranged as to irradiate said cell being set in said cell setting part with said measuring beam, said light receiving part being so arranged as to receive said measuring beam being transmitted through said cell.

8. The uric component measuring apparatus in accordance with claim 7, wherein
said cell is so mounted on said urine collecting part as to project toward the forward end of said urinal body in a horizontal plane on said forward end of said urine collecting part being opposed to its urine inlet when said urine collecting part is placed to upwardly direct said urine inlet.

9. The uric component measuring apparatus in accordance with claim 7, wherein said measuring part further comprises a sensor part for optically or mechanically detecting that said cell is set in said cell setting part, an operation of said measuring part being started on the basis of a signal indicating that said sensor part detects said cell.

10. The uric component measuring apparatus in accordance with claim 5, wherein said urine collecting part comprises an openable/closable urine discharge nozzle projecting from said urine collecting part, said measuring part having a cell in a position for receiving said urine being discharged from said nozzle, said light source part being so arranged as to irradiate said cell with said measuring beam, said light receiving part being so arranged as to receive said measuring beam being transmitted through said cell.

11. The uric component measuring apparatus in accordance with claim 10, wherein said nozzle is an electromagnetic nozzle being opened/closed by an electromagnetic valve, said measuring part further comprising a sensor part for optically or mechanically detecting that said nozzle is set on a prescribed position of said measuring part, said electromagnetic valve being opened for a constant time on the basis of a signal indicating that said sensor part detects said nozzle.

12. The uric component measuring apparatus in accordance with claim 10, wherein said nozzle is so mounted on said urine collecting part as to project toward the forward end of said urinal body in a horizontal plane on said forward end of said urine collecting part being opposed to its urine inlet when said urine collecting part is placed to upwardly direct said urine inlet.

13. The uric component measuring apparatus in accordance with claim 5, wherein said measuring wavelengths of said measuring part are selected from wavelengths having correlation coefficients which have absolute values of at least 0.5 and not greater than 1.0, said correlation coefficients being defined as coefficients between concentrations and absorbances of aqueous solutions containing respective single components in the visible or near infrared wavelength region according to the formula:

$$Rj = \frac{(m-1) \sum_{i=1}^{m} (Aij - \overline{Aj})(Ci - \overline{C})}{\sum_{i=1}^{m} (Aij - \overline{Aj}) \cdot \sum_{i=1}^{m} (Ci - \overline{C})}$$

where:

$$\overline{Aj} = \frac{1}{m} \sum_{i=1}^{m} Aij$$

$$\overline{C} = \frac{1}{m} \sum_{i=1}^{m} Ci$$

where:

m: the number of samples

Aij: absorbance of the component in i th sample at wavelength λj

Ci: concentration of the component in i th sample, said measuring wavelengths being specific to respective said uric components, and said arithmetic processing part calculates a plurality of uric component concentrations by multivariate regression analysis.

14. The uric component measuring apparatus in accordance with claim 13, wherein said uric components to be measured include a plurality of components selected from the group consisting of glucose, hemoglobin, albumin, lithium acetoacetate, ascorbic acid, creatinine, sodium chloride and sodium nitrite, said measuring wavelengths for said components, expressed in wavenumbers, being selected:

from 11380 to 9720 $cm^{-1}$, 9430 to 9400 $cm^{-1}$, 9340 to 9320 $cm^{-1}$, 9260 to 6560 $cm^{-1}$, 6510 to 5540 $cm^{-1}$, 5530 to 5280 $cm^{-1}$, 4980 to 4850 $cm^{-1}$, 4830 to 4480 $cm^{-1}$, 4440 to 4330 $cm^{-1}$ or 4300 to 4010 $cm^{-1}$ for glucose, from 25000 to 7250 $cm^{-1}$, 7220 to 6430 $cm^{-1}$, 6190 to 5690 $cm^{-1}$, 5660 to 5280 $cm^{-1}$, or 4900 to 4080 $cm^{-1}$ for hemoglobin, from 7280 to 6350 $cm^{-1}$, 5910 to 5880 $cm^{-1}$, 5790 to 5740 $cm^{-1}$, 5630 to 5300 $cm^{-1}$, 4900 to 4720 $cm^{-1}$, 4670 to 4280 $cm^{-1}$ or 4230 to 4070 $cm^{-1}$ for albumin, from 8490 to 6360 $cm^{-1}$, 6040 to 5610 $cm^{-1}$, 5430 to 5300 $cm^{-1}$, 4900 to 4760 $cm^{-1}$, 4680 to 4510 $cm^{-1}$ or 4470 to 4320 $cm^{-1}$ for lithium acetoacetate;

from 7270 to 6520 $cm^{-1}$, 6430 to 5290 $cm^{-1}$, 4950 to 4860 $cm^{-1}$ or 4810 to 4090 $cm^{-1}$ for ascorbic acid, from 9370 to 5870 $cm^{-1}$, 5810 to 5280 $cm^{-1}$, 4980 to 4730 $cm^{-1}$, 4690 to 4320 $cm^{-1}$ or 4290 to 4090 $cm^{-1}$ for creatinine, from 7640 to 5280 $cm^{-1}$ or 4980 to 4080 $cm^{-1}$ for sodium chloride, and from 8680 to 5300 $cm^{-1}$, 4980 to 4210 $cm^{-1}$ or 4160 to 4100 $cm^{-1}$ for sodium nitrite.

15. A stool comprising:

a stool body;

a urine collecting part being provided in said stool body in a position for receiving urine;

a measuring part comprising a cell receiving said urine being collected in said urine collecting part, a light source part for irradiating said cell with a measuring beam of wavenumber not higher than about 25,000 $cm^{-1}$ and not lower than about 4,000 $cm^{-1}$, and a light receiving part for receiving and detecting said measuring beam being transmitted through said cell, for measuring absorbances of respective uric components to be measured at measuring wavelengths being selected therefor respectively;

a data analysis part for calculating a plurality of uric component concentrations on the basis of said absorbances being measured by said measuring part at a plurality of said measuring wavelengths; and an input/output part comprising a data input part for inputting data required for a measuring operation and a test result output part for outputting results of data analysis being obtained by said data analysis part.

16. The stool in accordance with claim 15, wherein said data analysis part is mounted on said stool body.

17. The stool in accordance with claim 15, wherein said data analysis part is a computer being independent of said stool body, a data transmission part being mounted on said stool body for transferring data between said measuring part and said data analysis part.

18. The stool in accordance with claim 15, wherein said urine collecting part is provided with a washing mechanism.

19. The stool in accordance with claim 18, wherein said urine collecting part is provided with a sensor part for testing the degree of soiling, said washing mechanism being started upon a determination that said urine collecting part is soiled in excess of a set value.

20. The stool in accordance with claim 15, wherein said cell is provided with a washing mechanism.

21. The stool in accordance with claim 20, wherein said cell is provided with a sensor part for testing the degree of soiling, said washing mechanism being started upon a determination that said cell is soiled in excess of a set value.

22. The stool in accordance with claim 15, wherein said measuring wavelengths of said measuring part are selected from wavelengths having correlation coefficients which have absolute values of at least 0.5 and not greater than 1.0, said correlation coefficients being defined as coefficients between concentrations and absorbances of aqueous solutions containing respective single components in the visible or near infrared wavelength region according to the formula:

$$Rj = \frac{(m-1)\sum_{i=1}^{m}(Aij - \overline{Aj})(Ci - \overline{C})}{\sum_{i=1}^{m}(Aij - \overline{Aj}) \cdot \sum_{i=1}^{m}(Ci - \overline{C})}$$

where:

$$\overline{Aj} = \frac{1}{m}\sum_{i=1}^{m} Aij$$

$$\overline{C} = \frac{1}{m}\sum_{i=1}^{m} Ci$$

where:
- m: the number of samples
- Aij: absorbance of the component in th sample at wavelength $\lambda j$
- Ci: concentration of the component in i th sample, said measuring wavelengths being specific to respective said uric components, and said data analysis part calculates a plurality of uric component concentrations by multivariate regression analysis.

23. The stool in accordance with claim 15, wherein said uric components to be measured include a plurality of components selected from the group consisting of glucose, hemoglobin, albumin, lithium acetoacetate, ascorbic acid, creatinine, sodium chloride and sodium nitrite, said measuring wavelengths for said components, expressed in wavelengths, being selected:

from 11380 to 9720 $cm^{-1}$, 9430 to 9400 $cm^{-1}$, 9340 to 9320 $cm^{-1}$, 9260 to 6560 $cm^{-1}$, 6510 to 5540 $cm^{-1}$, 5530 to 5280 $cm^{-1}$, 4980 to 4850 $cm^{-1}$, 4830 to 4480 $cm^{-1}$, 4440 to 4330 $cm^{-1}$ or 4300 to 4010 $cm^{-1}$ for glucose, from 25000 to 7250 $cm^{-1}$, 7220 to 6430 $cm^{-1}$, 6190 to 5690 $cm^{-1}$, 5660 to 5280 $cm^{-1}$, or 4900 to 4080 $cm^{-1}$ for hemoglobin, from 7280 to 6350 $cm^{-1}$, 5910 to 5880 $cm^{-1}$, 5790 to 5740 $cm^{-1}$, 5630 to 5300 $cm^{-1}$, 4900 to 4720 $cm^{-1}$, 4670 to 4280 $cm^{-1}$ or 4230 to 4070 $cm^{-1}$ for albumin, from 8490 to 6360 $cm^{-1}$, 6040 to 5610 $cm^{-1}$, 5430 to 5300 $cm^{-1}$, 4900 to 4760 $cm^{-1}$, 4680 to 4510 $cm^{-1}$ or 4470 to 4320 $cm^{-1}$ for lithium acetoacetate;

from 7270 to 6520 $cm^{-1}$, 6430 to 5290 $cm^{-1}$, 4950 to 4860 $cm^{-1}$ or 4810 to 4090 $cm^{-1}$ for ascorbic acid, from 9370 to 5870 $cm^{-1}$, 5810 to 5280 $cm^{-1}$, 4980 to 4730 $cm^{-1}$, 4690 to 4320 $cm^{-1}$ or 4290 to 4090 $cm^{-1}$ for creatinine, from 7640 to 5280 $cm^{-1}$ or 4980 to 4080 $cm^{-1}$ for sodium chloride, and from 8680 to 5300 $cm^{-1}$, 4980 to 4210 $cm^{-1}$ or 4160 to 4100 $cm^{-1}$ for sodium nitrite.

* * * * *